United States Patent [19]
Kato et al.

[11] Patent Number: 5,804,601
[45] Date of Patent: Sep. 8, 1998

[54] AROMATIC HYDROXAMIC ACID COMPOUNDS, THEIR PRODUCTION AND USE

[75] Inventors: Kaneyoshi Kato, Kawanishi; Shokyo Miki, Ibaraki; Ken-ichi Naruo, Sanda; Hideki Takahashi, Ikeda, all of Japan

[73] Assignee: Takeda Chemical Industries, Ltd., Osaka, Japan

[21] Appl. No.: 629,623

[22] Filed: Apr. 9, 1996

[30] Foreign Application Priority Data

Apr. 10, 1995 [JP] Japan .................................. 7-084342
Aug. 24, 1995 [JP] Japan .................................. 7-215932

[51] Int. Cl.$^6$ ...................... C07C 259/06; A61K 31/165
[52] U.S. Cl. ......................... 514/563; 546/136; 546/147; 548/171; 548/217; 552/299; 552/310; 562/874
[58] Field of Search ............................ 562/874; 548/171, 548/217; 552/229, 310; 540/136, 147; 514/563

[56] References Cited

U.S. PATENT DOCUMENTS

| | | | |
|---|---|---|---|
| 3,577,458 | 5/1971 | Brownstein et al. | 260/545 |
| 4,188,338 | 2/1980 | Bruins et al. | 260/500.5 |
| 4,564,476 | 1/1986 | Ho | 260/404 |
| 4,608,390 | 8/1986 | Summers, Jr. | 514/575 |
| 4,731,382 | 3/1988 | Zusi et al. | 514/575 |
| 5,180,742 | 1/1993 | Terao et al. | 514/558 |
| 5,272,180 | 12/1993 | Hashimoto et al. | 514/575 |

FOREIGN PATENT DOCUMENTS

| | | |
|---|---|---|
| 0199151 | 10/1986 | European Pat. Off. . |
| 0199153 | 10/1986 | European Pat. Off. . |
| 0377896 | 7/1990 | European Pat. Off. . |
| 59-46244 | 3/1984 | Japan . |

OTHER PUBLICATIONS

Journal of Orgsinc Chemistry, vol. 26 (1961) pp. 782–784.

Kayumov Khim. Geterosikl. Soedin. 1973 (6) 756 Abstract Only.

Rajendra, Tetrahedron Letters 28 (50) 6257, 1987.

*Primary Examiner*—Robert Gerstl
*Attorney, Agent, or Firm*—Fitzpatrick, Cella, Harper & Scinto

[57] ABSTRACT

The present invention relates to a compound of the formula:

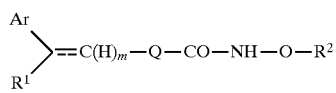

wherein Ar represents an optionally substituted aromatic group; Q represents a divalent aliphatic hydrocarbon group; $R_1$ represents hydrogen, cyano, an optionally substituted hydrocarbon group, a group of the formula:

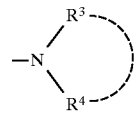

wherein $R^3$ and $R_4$ independently represent hydrogen, acyl or an optionally substituted hydrocarbon group, or $R^3$ and $R^4$ jointly form a ring, or acyl; $R^2$ represents acyl; ......... represents a single bond or a double bond; m represents 1 or 2 or a salt, a process of producing thereof and an anti-neurodegenerative composition.

16 Claims, No Drawings

AROMATIC HYDROXAMIC ACID COMPOUNDS, THEIR PRODUCTION AND USE

BACKGROUND OF THE INVENTION

1. Field of the Invention

The present invention relates to novel aromatic hydroxamic acid derivatives and anti-neurodegenerative compositions. More particularly, the invention relates to an aromatic hydroxamic acid derivative and a pharmaceutical composition which are effective for the therapy and prophylaxis of encephalopathies, for example neurodegenerative diseases such as Alzheimer's disease, Down's syndrome, etc. and diseases typically mediated by viral infections, such as viral meningitis, multiple sclerosis, and so forth.

2. Description of Related Art

The cerebral nerve tissue represented by the cerebral cortex is made up of neurons governing sensory and perceptive functions and glial cells (astrocytes, oligodendrocytes, microglia) supporting the neurons, with the glial cells accounting for 90 percent of the whole tissue.

It was generally thought once that the central nervous system (CNS) is static and the immune system in this area is in a special environment (the so-called immunologically privilege site). However, recent advances in molecular biological analysis have revealed that a variety of cytokines are intracerebrally produced and secreted and that the cellular or humoral immune system is playing a pivotal role to maintain homeostasis in the brain. At the same time, it has been suggested that excessive or abnormal activation of the immune system in CNS leads to the onset, progression and aggravation of various central diseases in the similar way as peripheral immune diseases.

Meanwhile, Alzheimer's disease (AD) is gathering attention as a type of dementia accompanied by degeneration and loss of neurons which is primarily found in aged people. With the increasing population of AD patients, the research and development work on drugs for the prevention and treatment of this disease is energetically pursued but the drugs so far developed are still providing only symptomatic relief at most and no fundamental drug therapy has been developed as yet.

In the intracerebral tissues of patients with Alzheimer's disease, accumulation of senile plaques and neurofibrillary tangles (NFT) are found and mentioned as a cause for the onset and progression of AD. Since deposits of β-amyloid protein (β-AP) are observed in senile plaques, it become convincing that the β-AP deposition, followed by aggregation, and formation of senile plaques is a chief etiologic factor in Alzheimer's disease. Moreover, the finding of microglial cells accumulated in activated state around senile plaques has led to the theory that the aggregation gains momentum as microglial cells attempt to phagocytize and eliminate β-AP and other deposits as foreign bodies and the formation of senile plaques is encouraged as a consequence. In senile plaques, complement deposits have also been found, and activation of the immune system has been pointed out as a cause for progression of AD morbidity and accompanying neuronal degeneration and loss. As it has, thus, been found that AD shares much with peripheral autoimmune diseases, it came to be regarded as an autoimmune disease of the brain. P. L. McGeer and co-workers who paid attention to the epidemiologically low incidence of AD in patients with rheumatoid arthritis who received long-term anti-inflammatory drug therapy with an anti-inflammatory agent (indomethacin) to AD patients and reported that the progression of AD could be suppressed (WO 93/24115). Moreover, WO 93/08819 describes that lycoportine, an endogenous IL-1 antagonist, is useful for neurodegenerative diseases but it is easy to imagine that being a macromolecular protein, lycoportine is not satisfactory enough in stability as well as the absorption and transfer to the brain after oral administration.

Glial cells; the principal cellular constituent of the central nervous system; are known to be associated with the differentiation and synapse formation of the brain and maintenance of its plasticy through an active homeostatic interaction with the neurons. On the other hand, it has been demonstrated that microglial cells among glial cells release a variety of immune factors in response to external stimuli such as derangements of the brain tissues due to infection or trauma (see V. H, Perry, P-B. Andersson, S. Gordon, Trends in Neurochemical Research 16, 268–273, 1993 etc). It is known that activated microglial cells, resident macrophages in brains, produce and release cytokines such as IL-1, IL-6 and TNFα. These cytokines are known to play an important role as messengers between immune cells (e.g. lymphocytes and macrophages). However, it has come to be understood that the activation of immune cells as triggered by excess production of such cytokines induces acute or chronic inflammatory diseases centrally and peripherally. For example, it is known that the cerebrospinal fluid levels of IL-1 β and IL-6 are high in patients with acute bacterial or viral meningitis. It has also been reported that interferon γ (IFNγ) and Tumor Necrosis Factor α (TNFα) levels are also elevated. Furthermore, it has been suggested that these cytokines are also involved in multiple sclerosis (MS) which is known to be a delayed intracerebral inflammatory disease mediated by immunological abnormality or viral infection. In Alzheimer's and Parkinson's diseases which are defined as neurodegenerative disorders, activated macrophages and microglial cells are observed in the brains of the afflicted patients, and particularly their accumulations at sites of nerve injury and around senile plaques have been demonstrated. Moreover, it has also been shown that in acute encephalopathies such as cerebral infarction, cerebral hemorrhage, subarachnoid hemorrhage and trauma, exacervation of the lesions may occur due to abnormal activation of microglial cells, macrophages, neutrophils, etc. For example, it has been suggested that drugs effective in inhibiting the neurodegeneration caused by activated microglia, abnormal production of IL-1 β and TNFα, or neuro-degeneration associated with β-amyloid are useful for the treatment, prevention and improved prognosis of neurodegenerative diseases such as Alzheimer's disease, Parkinson's disease, Down's syndrome, Pick's disease, multiple sclerosis, bacterial or viral meningitis such as Borna's disease, postvaccination encephalitis, and AIDS-associated encephalopathy, etc., and brain dysfunctions such as cerebral infarction, cerebral hemorrhage, subarachnoid hemorrhage, and trauma, etc. [Trends in Neuroscience, 16, 7, 268 (1993)].

Nitric oxide also plays crucial roles in the cardiovascular system, immune system, and central nervous system but it has been shown that excess nitric oxide acts as a potent cytotoxic factor in the biological systems. Moreover, abnormal release of nitric oxide due to enhanced excitement of the immune system may trigger septic shock and atherosclerosis, among other disorders [Annual Report in Medicinal Chemistry, 29, 83 (1994)].

As hydroxamic acid derivatives, the following compounds are known.

1) It is disclosed in JP-A-63 264442 and U.S. Pat. No. 4,731,382 that a compound of the general formula:

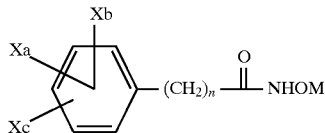

wherein n represents an integer of 6 to 11; M represents hydrogen or a pharmaceutically acceptable cation; Xa, Xb and Xc independently represent hydrogen, (lower)alkyl, (lower)alkenyl, $C_1$–$C_4$alkoxy, halo, nitro, hydroxy, amino, cyano, thio, aryl that may be substituted, aryl(lower)alkyl that may be substituted, (lower)alkylthio, acyl, acyloxy, acylamino, $C_{3-6}$ cycloalkyl, $C_{3-6}$ cycloalkyloxy, (lower) alkylamino, or di(lower)alkylamino; provided, however, that all of Xa, Xb and Xc are not hydrogen, has 5-lipoxygenase inhibitory activity and is useful for the prevention and treatment of inflammatory diseases in mammalian animals.

2) JP-A-59 46244 discloses that a hydroxamic acid derivative of the general formula:

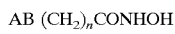

wherein A represents RXm (R represents phenyl, pyrrolyl, thienyl, imidazolyl or thiazolyl; X represents halogen, lower alkyl, lower acyloxy, or nitro; m represents 0, 1 or 2; X occuring m times may be the same or different); B represents —CHOH—, —$CH_2$—, —O— or —CO—; n represents an integer of 2–10 which is of value as an antiprotozoal drug or an antiprotozoal intermediate compound.

3) It is disclosed in U.S. Pat. No. 4,564,476 that a compound of the general formula:

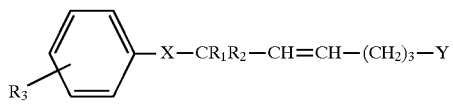

wherein $R_1$, $R_2$ and $R_3$ independently represent hydrogen, among others; X represents CH=CH, among others; Y represents —$CONHR^4$ ($R^4$ means alkyl or hydroxy), among others) has lipoxygenase inhibitory activity.

4) JP-A-53 84938 and U.S. Pat. No. 4,188,338 disclose that a compound of the general formula:

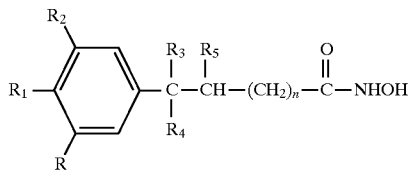

wherein R represents $C_{1-6}$alkoxy, among others; $R_1$ and $R_2$ independently represent hydrogen or $C_{1-6}$alkoxy, among others; $R_3$ and $R_4$ independently represent hydrogen or $C_{1-6}$alkyl; $R_5$ represents hydrogen or, taken together with $R_3$ or $R_4$, represents methylene; n represents 0 or 1, is useful for preventing platelet aggregation.

5) JP-A-61 251640 and U.S. Pat. No. 4,608,390 disclose that a compound of the formula:

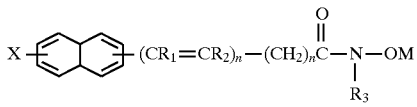

wherein X represents hydrogen, $C_{1-22}$alkyl, alkenyl or an electron-withdrawing group; n represents 0 or 1; m represents 0, 1, 2 or 3; provided, however, that both n and m are not concurrently equal to 0; $R_1$ and $R_2$ independently represent hydrogen, $C_{1-6}$alkyl, an electron-withdrawing group or $R_4$; $R_3$ represents hydrogen, $C_{1-6}$alkyl, cycloalkyl or $R_4$; $R_4$ represents a group of the formula:

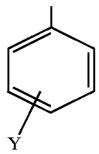

wherein Y represents hydrogen or an electron-withdrawing group; M represents a pharmacologically acceptable cation which is an inhibitor of lipoxygenase.

6) It is disclosed in EP-199,151A2 that a compound of the formula

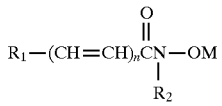

($R_1$ represents a tricyclic aromatic or biaryl group; $R_2$ represents hydrogen, $C_{1-6}$alkyl, or cycloalkyl; n represents 0 or 1; M represents a medicinally acceptable cation) has lipoxygenase-inhibitory activity.

7) JP-A-1 104033 and JP-A-1 110624 describe compounds of the formula:

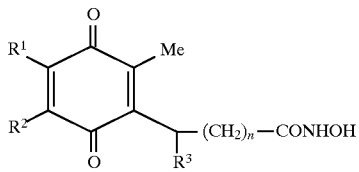

wherein $R_1$ and $R_2$ may be the same or different and each represents methyl or methoxy, or $R^1$ and $R^2$ jointly represent —CH=CH—CH=CH—; $R^3$ represents an aromatic or heterocyclic group that may be substituted; n represents an integer of 2–8 (JP-A-1 110624) or an integer of 5 or 6 (JP-A-1 104033) and which possesses cell proliferation-inhibitory, neovascularization-inhibitory and autoimmune disease-ameliorating actions.

8) JP-A-61 44840 discloses that a compound of the general formula:

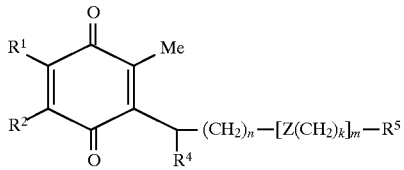

wherein $R^1$, $R^2$ and $R^3$ each represents hydrogen or methyl, among others; $R^4$ represents an aliphatic, aromatic or heterocyclic group that may be substituted; $R^5$ represents a carboxyl group that may be esterified or amidated, among others; Z represents —CH=CH—, among others; n represents an integer of 0–10; m represents an integer of 0–3; k represents an integer of 0–5] has 5-lipoxygenase inhibitory activity and is of value as an antiasthmatic, antiallergic or ameliorating cerebral circulation agent.

Furthermore, as compounds having thromboxane synthase-inhibitory activity, JP-A-58 92677 discloses, among N-substituted-2-pyridylindole compounds, 1-(7-hydroxycarbamoyl-heptyl)-3-methyl-2-(3-pyridyl)indole hydrochloride, and JP-A-59 118784 discloses, as a typical substituted imidazo[1,5-a]pyridine derivative, 5-[5-(hydroxycarbamoyl)pentyl]-imidazo[1,5-a]pyridine, both referring to their therapeutic efficacy in thromboembolism.

However, in none of those compounds, the OH group of hydroxamic acid has been substituted by an acyl group. The O-carbamoyl derivative of phenylacetohydroxamic acid is described in Journal of Organic Chemistry, 26, 782 (1961) but this literature is reticent about its pharmacological activity.

Not known is a drug substance that would significantly inhibit neurodegeneration by antagonizing activation of intracerebral immunity-related cells (e.g. microglial cells, astrocytes, etc.) and a strong need has been felt for the development of a new drug useful for the prophylaxis and therapy of encephalopathies.

SUMMARY OF THE INVENTION

The inventors of the present invention, after much research, synthesized aromatic hydroxamic acid derivatives having an acyl group on the oxygen atom of the hydroxamic acid moiety as represented by the formula:

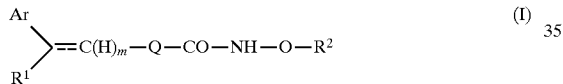

wherein Ar represents an optionally substituted aromatic group; Q represents a divalent aliphatic hydrocarbon group; $R^1$ represents i) hydrogen, ii) a cyano group, iii) an optionally substituted hydrocarbon group, iv) a group of the formula:

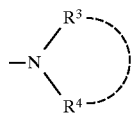

wherein $R^3$ and $R^4$ independently represent hydrogen, an acyl group or an optionally substituted hydrocarbon group, or $R^3$ and $R_4$, taken together with the adjacent nitrogen atom, may form a ring, or v) an acyl group;

$R_2$ represents an acyl group;

......... represents a single bond or a double bond;

m represents 1 or 2 or a salt thereof (hereinafter referred to as compound (I)) and discovered through a series of pharmacological experiments that a class of compounds inclusive of the thus-synthesized compounds and having the formula:

wherein $R^2$ represents hydrogen or an acyl group; the other symbols have the same meanings as defined above, and a salt thereof (hereinafter referred to as compound (II)) have excellent antineuropathic activity with a low toxic potential and are, therefore, of great potential value as a therapeutic and prophylactic drug for encephalopathies. The finding was followed by further research, which has resulted in the perfection of the present invention.

DETAILED DESCRIPTION OF THE PREFERRED EMBODIMENTS

The present invention is, therefore, directed to:
(1) the compound (I),
(2) the compound of above (1) wherein $R^1$ is i) hydrogen, ii) a cyano group, iii) an optionally substituted hydrocarbon group or iv) a group the formula:

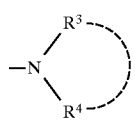

wherein $R^3$ and $R^4$ are independently hydrogen, an acyl group or an optionally substituted hydrocarbon group, or $R^3$ and $R^4$, taken together with the adjacent nitrogen atom, may form a ring,
(3) the compound of above (1) wherein Ar is a i) $C_{6-14}$aryl, ii) 5- to 11-membered heteroaromatic group containing, besides carbon atoms, 1 to 4 hetero atoms selected from nitrogen, oxygen and sulfur or iii) quinone group, each of which may be substituted by 1 to 5 substituents selected from the group consisting of halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, hydroxyl, amino, mono-$C_{1-6}$alkylamino, di-$C_{1-6}$alkylamino, $C_{1-6}$alkylcarbonyl, carboxyl, $C_{1-6}$alkoxycarbonyl, carbamoyl, mono-$C_{1-6}$alkylcarbamoyl, di-$C_{1-6}$alkylcarbamoyl, $C_{6-10}$arylcarbamoyl, sulfo, $C_{1-6}$alkylsulfonyl, $C_{6-10}$aryl, $C_{6-10}$aryloxy, optionally halogenated $C_{1-6}$alkylsulfonylamino and optionally substituted $C_{6-10}$arylsulfonylamino, Q is a divalent $C_{2-8}$ aliphatic hydrocarbon group, $R^1$ is i) hydrogen, ii) a cyano group, iii) a $C_{1-6}$alkyl, $C_{2-6}$alkenyl, $C_{2-6}$alkynyl, $C_{3-6}$cycloalkyl or $C_{6-14}$ aryl group, each of which may be substituted by 1 to 5 substituents selected from the group consisting of halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group, iv) a group of the formula:

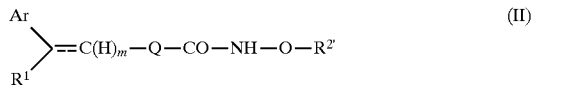

wherein $R^3$ and $R^4$ are independently a) hydrogen, b) an acyl group represented by the formula:

—CO—R, —SO$_2$—R, —SO—R, —CONH—R, —CO—O—R, —CS—NH—R or —CS—O—R wherein R is (1) hydrogen, (2) a C$_{1-6}$alkyl, C$_{2-6}$alkenyl, C$_{2-6}$alkynyl, C$_{3-6}$cycloalkyl or C$_{6-14}$aryl group, each of which may be substituted by 1 to 5 substituents selected from the group consisting of halogen, C$_{1-3}$alkylenedioxy, nitro, cyano, optionally halogenated C$_{1-6}$alkyl, optionally halogenated C$_{3-6}$cycloalkyl, optionally halogenated C$_{1-6}$alkoxy, optionally halogenated C$_{1-6}$alkylthio, amino, mono-C$_{1-6}$alkylamino, di-C$_{1-6}$alkylamino, hydroxyl, C$_{1-6}$alkylcarbonyl, carboxyl, C$_{1-6}$alkoxycarbonyl, C$_{1-6}$alkylcarbonyloxy, carbamoyl, mono-C$_{1-6}$alkylcarbamoyl, di-C$_{1-6}$alkylcarbamoyl, sulfo, C$_{1-6}$alkylsulfonyl, C$_{6-10}$aryl, C$_{6-10}$aryloxy and 5- or 6-membered heterocyclic group or (3) 5- to 10-membered heterocyclic group containing, besides carbon atoms, 1 to 3 hetero atoms selected from nitrogen, oxygen and sulfur, which may be substituted by 1 to 5 substituents selected from the group consisting of halogen, C$_{1-3}$ alkylenedioxy, nitro, cyano, optionally halogenated C$_{1-6}$alkyl, optionally halogenated C$_{3-6}$cycloalkyl, optionally halogenated C$_{1-6}$alkoxy, optionally halogenated C$_{1-6}$alkylthio, amino, mono-C$_{1-6}$alkylamino, di-C$_{1-6}$alkylamino, hydroxyl, C$_{1-6}$alkylcarbonyl, carboxyl, C$_{1-6}$alkoxycarbonyl, C$_{1-6}$alkylcarbonyloxy, carbamoyl, mono-C$_{1-6}$alkylcarbamoyl, di-C$_{1-6}$alkylcarbamoyl, sulfo, C$_{1-6}$alkylsulfonyl, C$_6$-loaryll C$_6$-loaryloxy and 5- or 6-membered heterocyclic group or c) a C$_{1-6}$alkyl, C$_{2-6}$alkenyl, C$_{2-6}$alkynyl, C$_{3-6}$cycloalkyl or C$_{6-14}$aryl group, each of which may be substituted by 1 to 5 substituents selected from the group consisting of halogen, C$_{1-3}$alkylenedioxy, nitro, cyano, optionally halogenated C$_{1-6}$alkyl, optionally halogenated C$_{3-6}$cycloalkyl, optionally halogenated C$_{1-6}$alkoxy, optionally halogenated C$_{1-6}$alkylthio, amino, mono-C$_{1-6}$alkylamino, di-C$_{1-6}$alkylamino, hydroxyl, C$_{1-6}$alkylcarbonyl, carboxyl, C$_{1-6}$alkoxycarbonyl, C$_{1-6}$alkylcarbonyloxy, carbamoyl, mono-C$_{1-6}$alkylcarbamoyl, di-C$_{1-6}$alkylcarbamoyl, sulfo, C$_{1-6}$alkylsulfonyl, C$_{6-10}$aryl, C$_{6-10}$aryloxy and 5- or 6-membered heterocyclic group, or R$^3$ and R$^4$ taken together with the adjacent nitrogen atom, form a 5- to 7-membered nitrogen-containing ring having, besides carbon atoms and one nitrogen atom, 1 to 3 hetero atoms selected from nitrogen, oxygen and sulfur or v) an acyl group represented by the formula: —CO—R, —SO$_2$—R, —SO—R, —CONH—R, —CO—O—R, —CS—NH—R or —CS—O—R wherein R is (1) hydrogen, (2) a C$_{1-6}$alkyl, C$_{2-6}$alkenyl, C$_{2-6}$alkynyl, C$_{3-6}$cycloalkyl or C$_{6-14}$aryl group, each of which may be substituted by 1 to 5 substituents selected from the group consisting of halogen, C$_{1-3}$alkylenedioxy, nitro, cyano, optionally halogenated C$_{1-6}$alkyl, optionally halogenated C$_{3-6}$cycloalkyl, optionally halogenated C$_{1-6}$aikoxy, optionally halogenated C$_{1-6}$alkylthio, amino, mono-C$_{1-6}$alkylamino, di-C$_{1-6}$alkylamino, hydroxyl, C$_{1-6}$alkylcarbonyl, carboxyl, C$_{1-6}$alkoxycarbonyl, C$_{1-6}$alkylcarbonyloxy, carbamoyl, mono-C$_{1-6}$alkylcarbamoyl, di-C$_{1-6}$alkylcarbamoyl, sulfo, C$_{1-6}$alkylsulfonyl, C$_{6-10}$aryl, C$_{6-10}$aryloxy and 5- or 6-membered heterocyclic group or (3) 5- to 10-membered heterocyclic group containing, besides carbon atoms, 1 to 3 hetero atoms selected from nitrogen, oxygen and sulfur, which group may be substituted by 1 to 5 substituents selected from the group consisting of halogen, C$_{1-3}$alkylenedioxy, nitro, cyano, optionally halogenated C$_{1-6}$alkyl, optionally halogenated C$_{3-6}$cycloalkyl, optionally halogenated C$_{1-6}$alkoxy, optionally halogenated C$_{1-6}$alkylthio, amino, mono-C$_{1-6}$alkylamino, di-C$_{1-6}$alkylamino, hydroxyl, C$_{1-6}$alkylcarbonyl, carboxyl, C$_{1-6}$alkoxycarbonyl, C$_{1-6}$alkylcarbonyloxy, carbamoyl, mono-C$_{1-6}$alkylcarbamoyl, di-C$_{1-6}$alkylcarbamoyl, sulfo, C$_{1-6}$alkylsulfonyl, C$_{6-10}$aryl, C$_{6-10}$aryloxy and 5- or 6-membered heterocyclic group, and R2 is an acyl group represented by the formula: —CO—R, —SO$_2$—R, —SO—R, —CONH—R, —CO—O—R, —CS—NH—R or —CS—O—R wherein R is i) hydrogen, ii) a C$_{1-6}$alkyl, C$_{2-6}$alkenyl, C$_{2-6}$alkynyl, C$_{3-6}$cycloalkyl or C$_{6-14}$aryl group, each of which may be substituted by 1 to 5 substituents selected from the group consisting of halogen, C$_{1-3}$alkylenedioxy, nitro, cyano, optionally halogenated C$_{1-6}$alkyl, optionally halogenated C$_{3-6}$cycloalkyl, optionally halogenated C$_{1-6}$alkoxy, optionally halogenated C$_{1-6}$alkylthio, amino, mono-C$_{1-6}$alkylamino, di-C$_{1-6}$alkylamino, hydroxyl, C$_{1-6}$alkylcarbonyl, carboxyl, C$_{1-6}$alkoxycarbonyl, C$_{1-6}$alkylcarbonyloxy, carbamoyl, mono-C$_{1-6}$alkylcarbamoyl, di-C$_{1-6}$alkylcarbamoyl, sulfo, C$_{1-6}$alkylsulfonyl, C$_{6-10}$aryl, C$_{6-10}$aryloxy and 5- or 6-membered heterocyclic group or iii) 5- to 10-membered heterocyclic group containing, besides carbon atoms, 1 to 3 hetero atoms selected from nitrogen, oxygen and sulfur, which group may be substituted by 1 to 5 substituents selected from the group consisting of halogen, C$_{1-3}$alkylenedioxy, nitro, cyano, optionally halogenated C$_{1-6}$alkyl, optionally halogenated C$_{3-6}$cycloalkyl, optionally halogenated C$_{1-6}$alkoxy, optionally halogenated C$_{1-6}$alkylthio, amino, mono-C$_{1-6}$alkylamino, di-C$_{1-6}$alkylamino, hydroxyl, C$_{1-6}$alkylcarbonyl, carboxyl, C$_{1-6}$ alkoxycarbonyl, C$_{1-6}$alkylcarbonyloxy, carbamoyl, mono- C$_{1-6}$ alkylcarbamoyl, di-C$_1$l$_6$alkylcarbamoyl, sulfo, C$_{1-6}$ alkylsulfonyl, C$_{6-10}$oaryl, C$_{6-10}$aryloxy and 5- or 6-membered heterocyclic group, (4) the compound of above (3) wherein Ar is a i) p-benzoquinon-2-yl, ii) 1,4-naphthoquinon-2-yl, iii) anthraquinonyl, iv) 5,6-chrysenequinonyl or v) 5,8-dioxo-5,8-dihydroquinolin-6-yl group, each of which may be substituted by 1 to 5 substituents selected from the group consisting of halogen, C$_{13}$alkylenedioxy, nitro, cyano, optionally halogenated C$_{1-6}$alkyl, optionally halogenated C$_{3-6}$cycloalkyl, optionally halogenated C$_{1-6}$alkoxy, optionally halogenated C$_{1-6}$alkylthio, hydroxyl, amino, mono-C$_{1-6}$alkylamino, di-C$_{1-6}$alkylamino, C$_{1-6}$ alkylcarbonyl, carboxyl, C$_{1-6}$ alkoxycarbonyl, carbamoyl, mono-C$_{1-6}$ alkylcarbamoyl, di-C$_{1-6}$alkylcarbamoyl, C$_{6-10}$arylcarbamoyl, sulfo, C$_{1-6}$alkylsulfonyl, C$_{6-10}$aryl, C$_{6-10}$aryloxy, optionally halogenated C$_{1-6}$alkylsulfonylamino and optionally substituted C$_{6-10}$arylsulfonylamino, R$^1$ is a phenyl or naphthyl group which may be substituted by 1 to 5 substituents selected from the group consisting of halogen, C$_{1-3}$alkylendioxy, nitro, cyano, optionally halogenated C$_{1-6}$alkyl, optionally halogenated C$_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group, and $R^2$ is an acyl group of the formula: —CO—R or —CO—NH—R wherein R is as defined in above (3), (5) the compound of above (3) wherein $R^1$ is a cyano group and R2 is an acyl group of the formula: —CO—R or —CO—NH—R wherein R is as defined in above (3), (6) the compound of above (1) wherein Ar is a phenyl, 1-naphthyl, 2-naphthyl, 2-quinolyl, 3-quinolyl, 4-quinolyl, 1-isoquinolyl, 4-isoquinolyl, 2-benzothiazolyl, 2-benzoxazolyl, 2-benzimidazolyl, 2-pyridothiazolyl, p-benzoquinon-2-yl, 1,4-naphthoquinon-2-yl or 5,8-dioxo-5,8-dihydroquinolin-6-yl group, each of which may be substituted by 1 to 4 substituents selected from the group consisting of i) halogen, ii) nitro, iii) optionally halogenated $C_{1-6}$alkyl, iv) optionally halogenated $C_{1-6}$alkoxy, v) hydroxyl, vi) amino, vii) mono-$C_{1-6}$alkylamino, viii) di-$C_{1-6}$alkylamino, ix) optionally halogenated $C_{1-6}$alkylsulfonylamino and x) $C_{6-10}$arylsulfonylamino optionally substituted by 1 to 3 halogen atoms or optionally halogenated $C_{1-6}$alkyl, Q is a divalent $C_{2-5}$alkylene, $R^1$ is i) hydrogen, ii) a cyano group, iii) a phenyl group which may be substituted by 1 to 3 substituents selected from the group consisting of halogen, optionally halogenated $C_{1-6}$alkyl and optionally halogenated $C_{1-6}$alkoxy, iv) a group of the formula:

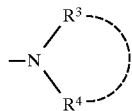

wherein $R^3$ is hydrogen and $R^4$ is an acyl group of the formula: —CO—R' or —SO$_2$—R' wherein R' is a $C_{1-6}$alkyl or $C_{6-14}$ aryl group which may be substituted by 1 to 3 substituents selected from the group consisting of halogen and $C_{1-6}$alkyl, or v) an acyl group of the formula: —CO—O—R'' wherein R'' is a $C_{1-6}$alkyl group, $R^2$ is an acyl group of the formula: —CO—R''' or —CONH—R''' wherein R''' is i) hydrogen or ii) a $C_{1-6}$alkyl, $C_{3-6}$cycloalkyl or $C_{6-14}$aryl group which may be substituted by 1 to 3 substituents selected from the group consisting of a) halogen, b) optionally halogenated $C_{1-6}$ alkyl, c) optionally halogenated $C_{1-6}$alkoxy, d) $C_{1-6}$alkylcarbonyloxy and e) $C_{6-14}$aryl optionally substituted by 1 to 3 substituents selected from the group consisting of $C_{1-6}$alkyl and $C_{1-6}$alkoxy, ......... is a single bond, and m is 2, (7) the compound of above (6) wherein Ar is a p-benzoquinon-2-yl or 1,4-naphthoquinon-2-yl group which may be substituted by 1 to 4 substituents selected from the group consisting of i) halogen, ii) optionally halogenated $C_{1-6}$alkyl and iii) optionally halogenated $C_{1-6}$alkoxy, $R^1$ is a phenyl group which may be substituted by 1 to 3 substituents selected from the group consisting of halogen, optionally halogenated $C_{1-6}$alkyl and optionally halogenated $C_{1-6}$alkoxy, and $R^2$ is an acyl group of the formula: —CO—R'''' wherein R''''– is a $C_{1-6}$alkyl, $C_{3-6}$cycloalkyl or phenyl group which may be substituted by 1 to 3 halogens, (8) the compound of above (3) wherein Q is trimethylene or tetramethylene, (9) the compound of above (1) which is
O-acetyl-6-(4-methoxyphenyl)-6-(3-methyl-1,4-naphthoquinon-2-yl)hexanohydroxamic acid,
O-propionyl-6-(4-methoxyphenyl)-6-(3-methyl- 1,4-naphthoquinon-2-yl)hexanohydroxamic acid,
O-isobutyryl-6-(4-methoxyphenyl)-6-(3-methyl-1,4-naphthoquinon-2-yl)hexanohydroxamic acid,
O-benzoyl-6-(4-methoxyphenyl)-6-(3-methyl-1,4-naphthoquinon-2-yl)hexanohydroxamic acid,
O-propionyl-7-(4-methoxyphenyl)-7-(3-methyl-1,4-naphthoquinon-2-yl)heptanohydroxamic acid,
O-propionyl-7-(4-fluorophenyl)-7-(3-methyl-1,4-naphthoquinon-2-yl)heptanohydroxamic acid, or a salt thereof,

(10) a process for producing the compound of above (1), which comprises reacting a compound of the formula:

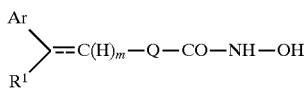

wherein all symbols are as defined above, or a salt thereof with a compound of the formula:

$$Y—R^2$$

wherein Y represents a leaving group and $R^2$ is as defined above, or a salt thereof,

(11) an anti-neurodegenerative composition which comprises the compound (II), if necessary with a pharmaceutically acceptable carrier,

(12) an anti-neurodegenerative composition which comprises the compound (I), if necessary with a pharmaceutically acceptable carrier,

(13) the composition of above (11) which comprises
O-propionyl-6-(4-methoxyphenyl)-6-(3-methyl-1,4-naphthoquinon-2-yl)hexanohydroxamic acid,
O-propionyl-7-(4-methoxyphenyl)-7-(3-methyl-1,4-naphthoquinon-2-yl)heptanohydroxamic acid,
7-(4-methoxyphenyl)-7-(3-methyl-1,4-naphthoquinon-2-yl)heptanohydroxamic acid,
6-(4-methoxyphenyl)-6-(3-methyl-1,4-naphthoquinon-2-yl)hexanohydroxamic acid, or a salt thereof,

(14) the composition of above (11) which is for preventing or treating neurodegenerative diseases, and

(15) the composition of above (14) which is for preventing or treating Alzheimer's disease or multiple sclerosis, among others.

Referring to the above formulas (I) and (II), the compounds wherein the bond  is a single bond can be written as follows.

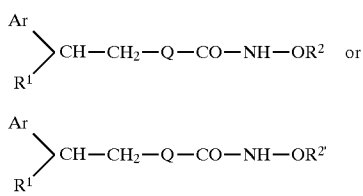

(I-1)

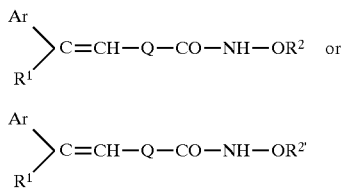

(II-1)

wherein each symbol has the same meaning as defined hereinbefore. The compounds wherein the bond ......... is a double bond can be written as follows.

$$\underset{R^1}{\overset{Ar}{>}}C=CH-Q-CO-NH-OR^2 \text{ or} \quad (I\text{-}2)$$

$$\underset{R^1}{\overset{Ar}{>}}C=CH-Q-CO-NH-OR^{2'} \quad (II\text{-}2)$$

wherein each symbol has the same meaning as defined hereinbefore.

Referring to the above formulas (I) and (II), the aromatic group for the "optionally substituted aromatic group" of Ar includes, for example, aromatic hydrocarbon groups, heteroaromatic groups and quinone groups.

The "aromatic hydrocarbon group" mentioned above includes, for example, monocyclic and fused polycyclic aromatic hydrocarbon groups each containing 6 to 14 carbon atoms. Among them are $C_{6-14}$aryl groups such as phenyl, 1-naphthyl, 2-naphthyl, indenyl, anthryl, and so forth. Of these aryl groups, phenyl, 1-naphthyl, and 2-naphthyl are preferred and 1-naphthyl and 2-naphthyl are particularly preferred.

The "heteroaromatic group" mentioned above includes, for example, 5- to 11-membered monocyclic heterocyclic groups each containing one or more (e.g. 1–4) hetero-atoms selected from nitrogen, sulfur and oxygen in addition to carbon as ring members and the corresponding fused heteroaromatic groups (e.g. one of the above defined monocyclic heterocyclic groups fused to one or more (preferably 1 or 2, more preferably 1) aromatic rings selected from the above defined aromatic hydrocarbon groups and monocyclic heterocyclic groups, etc.). More particularly, there can be mentioned a variety of monovalent groups available on elimination of one hydrogen atom each from various monocyclic heteroaromatic rings or fused heterocyclic rings which are formed by fusing any of such monocyclic heteroaromatic rings to one or more (preferably 1 or 2) aromatic rings (e.g. benzene ring, pyridine ring, etc.). Thus, thiophene, benzo[b]thiophene, benzo[b]furan, benzimidazole, benzoxazole, benzothiazole, benzisothiazole, naphtho[2,3-b]thiophene, thianthrene, furan, isoindolizine, xanthene, phenoxathiin, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, isothiazole, phenothiazine, isoxazole, furazan, phenoxazine, isochroman, etc. can be specifically mentioned. The preferred "heteroaromatic group" includes 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinol-yl, 1-indolyl, 2-indolyl, 3-indolyl, 2-benzothiazolyl, 2-benzo[b]thienyl, benzo[b]furanyl, 2-thienyl, 3-thienyl, 2-benzoxazolyl, 2-benzimidazolyl, 2-pyridothiazolyl, and so forth. Among the more preferred species are 2-quinolyl, 3-quinolyl, 4-quinolyl, 1-isoquinolyl, 4-isoquinolyl, 2-benzothiazolyl, 2-benzoxazolyl, 2-benzimidazolyl, 2-pyridothiazolyl and so forth. Particularly preferred are 2-quinolyl, 4-quinolyl and 1-isoquinolyl.

The "quinone group" mentioned above means a group available on elimination of one hydrogen atom from a quinone ring and, includes, for example, p-benzoquinone, 1,4-naphthoquinone, anthraquinone, 5,6-chrysenequinone, 5,8-dioxo-5,8-dihydroquinoline, etc. Preferred are p-benzoquinone and 1,4-naphthoquinone.

The substituent for the "optionally substituted aromatic group" of Ar includes, for example, halogen (e.g. fluorine, chlorine, bromine, iodine), $C_{1-3}$alkylenedioxy (e.g. methylenedioxy, ethylenedioxy, etc.), nitro, cyano, optionally halogenated $C_{1-6}$alkyl, optionally halogenated $C_{3-6}$cycloalkyl (e.g. cyclopropyl, cyclobutyl, cyclopentyl, cyclohexyl, etc.), optionally halogenated $C_{1-6}$alkoxy, optionally halogenated $C_{1-6}$alkylthio, hydroxy, amino, mono-$C_{1-6}$alkylamino (e.g. methylamino, ethylamino, propylamino, isopropylamino, butylamino, etc.), di-$C_{1-6}$alkylamino (e.g. dimethylamino, diethylamino, dipropylamino, dibutylamino, etc.), $C_{1-6}$ alkylcarbonyl (e.g. acetyl, propionyl, etc.), carboxy, $C_{1-6}$alkoxycarbonyl (e.g. methoxycarbonyl, ethoxycarbonyl, propoxycarbonyl, butoxycarbonyl, etc.), carbamoyl, mono-$C_{1-6}$ alkylcarbamoyl (e.g. methylcarbamoyl, ethylcarbamoyl, etc.), di-$C_{1-6}$ alkylcarbamoyl (e.g. dimethylcarbamoyl, diethylcarbamoyl, etc.), $C_{6-10}$arylcarbamoyl (e.g. phenylcarbamoyl, naphthylcarbamoyl, etc.), sulfo, $C_{1-6}$alkylsulfonyl (e.g. methylsulfonyl, ethylsulfonyl, etc.), $C_{6-10}$aryl (e.g. phenyl, naphthyl, etc.), $C_{6-10}$aryloxy (e.g. phenyloxy, naphthyloxy, etc.), optionally halogenated $C_{1-6}$alkylsulfonylamino, and optionally substituted $C_{6-10}$arylsulfonylamino, among others.

The "optionally halogenated $C_{1-6}$alkyl" as mentioned above includes, for example, $C_{1-6}$alkyl groups (e.g. methyl, ethyl, propyl, isopropyl, butyl, isobutyl, sec-butyl, tert-butyl, pentyl, hexyl, etc.) optionally having 1 to 3 halogen atoms (e.g. F, Cl, Br, I). Thus, for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. can be mentioned.

The "optionally halogenated $C_{3-6}$ cycloalkyl" as mentioned above includes, for example $C_{3-6}$cycloalkyl groups optionally having 1 to 3 halogen atoms (e.g. F, Cl, Br, I) such as cyclopropyl, cyclobutyl, cyclopentyl, cyclohexyl, 2,2,3,3-tetrafluorocyclopentyl, 4-chlorocyclohexyl, etc.

The "optionally halogenated $C_{1-6}$alkoxy" as mentioned above includes, for example, $C_{1-6}$alkoxy groups optionally having 1 to 3 halogen atoms (e.g. F, Cl, Br, I). Thus, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and so on can be mentioned.

The "optionally halogenated $C_{1-6}$alkylthio" includes, for example, $C_{1-6}$alkylthio groups (e.g. methylthio, ethylthio, propylthio, isopropylthio, n-butylthio, sec-butylthio, tert-butylthio, etc.) optionally having 1 to 3 halogen atoms (e.g. F, Cl, Br, I), typically methylthio, difluoromethylthio, trifluoromethylthio, ethylthio, propylthio, isopropylthio, butylthio, 4,4,4-trifluorobutylthio, pentylthio, hexylthio, and so forth.

The "optionally halogenated $C_{1-6}$alkylsulfonylamino" as mentioned above includes, for example, $C_{1-6}$alkylsulfonylamino groups optionally having 1 to 3 halogen atoms (e.g. F, Cl, Br, I), typically methanesulfonylamino, trifluoromethanesulfonylamino, ethanesulfonylamino, and so forth.

The substituent for the "optionally substituted $C_{6-10}$arylsulfonylamino" includes, for example, 1 to 3 halogen atoms (e.g. fluorine, chlorine, bromine, iodine), optionally halogenated $C_{1-6}$alkyl groups, etc. The "optionally halogenated $C_{1-6}$ alkyl groups" may be those mentioned hereinbefore. To mention specific examples, the "optionally substituted $C_{6-10}$arylsulfonylamino" includes, for example, phenylsulfonylamino, tosylamino, p-fluorophenylsulfonylamino, 1-naphthylsulfonylamino and 2-naphthylsulfonylamino, among others.

The "aromatic group" for the "optionally substituted aromatic group" may have 1–5, preferably 1–3, substituents such as those mentioned above in substitutable positions of the ring and, where the number of substituents is not less than two, they may be similar or dissimilar to each other.

The preferred substituent for the "optionally substituted aromatic group" of Ar above includes, for example, halogen, nitro, optionally halogenated $C_{1-6}$alkyl, optionally halogenated $C_{1-6}$alkoxy, cyano, hydroxy, amino, $C_{6-10}$aryl, optionally halogenated $C_{1-6}$alkylsulfonylamino, and optionally substituted $C_{6-10}$arylsulfonylamino. Still more desirable are halogen and optionally halogenated $C_{1-6}$alkoxy groups.

When the "aromatic group" for the "optionally substituted aromatic group" of Ar is a quinone group, the preferred substituent for this quinone group are lower alkyl (e.g. $C_{1-6}$alkyl such as methyl, ethyl, etc.) and lower alkoxy (e.g. $C_{1-6}$alkoxy such as methoxy, ethoxy, etc.), among other substituent groups. Particularly preferred species of the "optionally substituted quinone group" are 3-methyl-1,4-naphthoquinon-2-yl, 3,5,6-trimethyl-1,4-benzoquinon-2-yl, 5,6-dimethoxy-3-methyl-1,4-benzoquino'n-2-yl, and 2-naphthoquinonyl.

The "divalent aliphatic hydrocarbon group" of Q means a divalent group which is available, for example, upon elimination of one hydrogen atom from each of the two carbon atoms of a saturated or unsaturated aliphatic hydrocarbon. The preferred is a group containing 2 to 8 carbon atoms. Specific examples of such group are shown below.

(i) $C_{2-8}$alkylene [e.g. —CH$_2$—, —(CH$_2$)$_2$—, —(CH$_2$)$_3$—, —(CH$_2$)$_4$—,

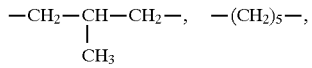

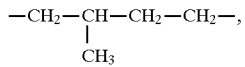

—(CH$_2$)$_6$—, —(CH$_2$)$_7$—, —(CH$_2$)$_8$—, etc.];

(ii) $C_{2-8}$alkenylene [e.g. —CH$_2$—CH=CH—, —CH$_2$—CH=CH—CH$_2$—, —CH$_2$—CH$_2$—CH=CH—, —CH=CH—CH$_2$—CH$_2$—CH$_2$—, —CH$_2$—CH$_2$—CH$_2$—CH=CH—, etc.]

(iii) $C_{2-8}$alkynylene [e.g. —C≡C—, —CH$_2$—C≡C—, —CH$_2$—C≡C—CH$_2$—CH$_2$—, etc.].

Among these groups, straight-chain groups are preferred.

Particularly preferred are $C_{2-8}$alkylene (e.g. ethylene, propylene, trimethylene, tetramethylene, pentamethylene, hexamethylene, etc.), $C_{2-6}$alkenylene (e.g. vinylene, propenylene, butenylene, pentenylene, hexenylene, etc.), and $C_{2-6}$alkynylene (e.g. propynylene, butynylene, pentynylene, etc.). Particularly preferred, among them, are $C_{2-6}$alkylene groups and, above all else, $C_{3-6}$alkylene groups.

The "hydrocarbon group" for the "optionally substituted hydrocarbon group" of $R^1$, $R^3$ or $R^4$ is a group available on elimination of one hydrogen atom from the corresponding hydrocarbon compound and includes both acyclic and cyclic hydrocarbon groups such as alkyl, alkenyl, alkynyl, cycloalkyl and aryl. Among them, acyclic or cyclic hydrocarbon groups containing 1 to 16 carbon atoms, such as the following, are preferred.

a) $C_{1-6}$alkyl (e.g. methyl, ethyl, propyl, isopropyl, butyl, isobutyl, sec-butyl, tert-butyl, pentyl, hexyl, etc.);

b) $C_{2-6}$alkenyl (e.g. vinyl, allyl, isopropenyl, butenyl, isobutenyl, sec-butenyl, etc.);

c) $C_{2-6}$alkynyl (e.g. propargyl, ethynyl, butynyl, 1-hexynyl, etc.);

d) $C_{3-6}$cycloalkyl (e.g. cyclopropyl, cyclobutyl, cyclopentyl, cyclohexyl which may be fused to a benzene ring optionally having 1–3 $C_{1-6}$alkoxy (e.g. methoxy) groups, etc.);

e) $C_{6-14}$aryl (e.g. phenyl, 1-naphthyl, 2-naphthyl, biphenyl, 2-indenyl, 2-anthryl, etc.), preferably phenyl.

Among the above groups, $C_{1-6}$alkyl, $C_{3-6}$cycloalkyl and $C_{6-14}$aryl are preferred.

The "substituent" for the "optionally substituted hydrocarbon group" of $R^1$, $R^3$ or $R^4$ includes, for example, halogen (e.g. fluorine, chlorine, bromine, iodine), $C_{1-3}$alkylenedioxy (e.g. methylenedioxy, ethylenedioxy, etc.), nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$ alkylamino (e.g. methylamino, ethylamino, etc.), di-$C_{1-6}$alkylamino (e.g. dimethylamino, diethylamino, etc.), hydroxy, $C_{1-6}$alkylcarbonyl (e.g. acetyl, ethylcarbonyl, etc.), carboxy, $C_{1-6}$alkoxycarbonyl (e.g. methoxycarbonyl, ethoxycarbonyl, propoxycarbonyl, butoxycarbonyl, etc.), $C_{1-6}$alkylcarbonyloxy (e.g. acetoxy, propionyloxy, etc.), carbamoyl, mono-$C_{1-6}$alkylcarbamoyl (e.g. methylcarbamoyl, ethylcarbamoyl, etc.), di-$C_{1-6}$alkylcarbamoyl (e.g. dimethylcarbamoyl, diethylcarbamoyl, etc.), sulfo, $C_{1-6}$alkylsulfonyl (e.g. methylsulfonyl, ethylsulfonyl, etc.), $C_{6-10}$aryl (e.g. phenyl, naphthyl, etc.), $C_{6-10}$aryloxy (e.g. phenyloxy, naphthyloxy, etc.), and 5- or 6-membered heterocyclic groups.

The above-mentioned "optionally halogenated $C_{1-6}$alkyl", "optionally halogenated $C_{3-6}$cycloalkyl", "optionally halogenated $C_{1-6}$alkoxy" and "optionally halogenated $C_{1-6}$alkylthio" include the groups mentioned for substituents on the aromatic group for Ar.

The "5- or 6-membered heterocyclic groups" mentioned above includes, for example, 5- or 6-membered heterocyclic groups each containing 1 to 3 hetero-atoms selected from nitrogen, oxygen and sulfur in addition to carbon as ring members. Specifically, 1-, 2- or 3-pyrrolidinyl, 2- or 4-imidazolinyl, 2, 3- or 4-pyrazolidinyl, piperidino, 2-, 3- or 4-piperidyl, 1- or 2-piperazinyl, morpholino, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl, etc. can be mentioned.

The above-mentioned "$C_{6-10}$aryl", or "$C_{6-10}$aryloxy" may, in turn, have 1–3 substituent groups such as halogen, $C_{1-6}$alkyl and $C_{1-6}$alkoxy.

The "hydrocarbon group" for the "optionally substituted hydrocarbon group" may have 1–5, preferably 1–3, substituent groups such as those mentioned above in substitutable positions and where two or more substituents are present, they may be similar or dissimilar to each other.

The "acyl" represented by $R^1$, $R^2$, $R^{2'}$, $R^3$ or $R^4$ includes, for example, acyl groups which can be represented by —CO—R, —SO$_2$—R, —SO—R, —CONH—R, —CO—O—R, —CS—NH—R, —CS—O—R, etc. (In these formulas, R represents hydrogen, an optionally substituted hydrocarbon group, or an optionally substituted heterocyclic group). Preferred, among them, are the acyl groups represented by —CO—R, —SO$_2$—R, —CONH—R and —CO—O—R, respectively.

The "optionally substituted hydrocarbon group" as represented by R includes, for example, those mentioned above for the "optionally substituted hydrocarbon group" for R$^1$, R$^3$ or R$^4$.

The "heterocyclic group" for the "optionally substituted heterocyclic group" for R typically includes 5- to 10-membered (monocyclic or bicyclic) heterocyclic groups each containing 1–3 hetero-atoms of 1 or 2 species selected from nitrogen, oxygen and sulfur in addition to carbon as ring members. Thus included are non-aromatic heterocyclic groups such as 1-, 2- or 3-pyrrolidinyl, 2- or 4-imidazolinyl, 2-, 3-or 4-pyrazolidinyl, piperidino, 2-, 3- or 4-piperidyl, 1- or 2-piperazinyl, morpholinyl, etc. and aromatic heterocyclic (heteroaromatic) groups such as 2-thienyl, 3-thienyl, 2-pyridyl, 3-pyridyl, 4-pyridyl, 2-furyl, 3-furyl, 4-quinolyl, 8-quinolyl, 4-isoquinolyl, pyrazinyl, 2-pyrimidinyl, 3-pyrrolyl, 2-imidazolyl, 3-pyridazinyl, 3-isothiazolyl, 3-isoxazolyl, 1-indolyl, 2-isoindolyl, and so on. Among these groups, heteroaromatic groups are preferred. Still more preferred are 5- or 6-membered heteroaromatic groups each containing 1–3 hetero-atoms selected from nitrogen, oxygen and sulfur in addition to carbon as ring members (e.g. 2-thienyl, 3-thienyl, 2-pyridyl, 4-pyridyl, etc.).

The substituent which may be optionally present on the "heterocyclic group" for the "optionally substituted heterocyclic group" may be similar, in kind and number, to the substituent optionally present on the "optionally substituted hydrocarbon group" for R$^1$, R$^3$ or R$^4$.

The "ring" which may be formed by R$^3$ and R$^4$ taken together with the adjacent nitrogen atom includes 5- to 7-membered nitrogen-containing ring having at least one nitrogen atom, optionally together with 1–3 heteroatoms selected from nitrogen, oxygen and sulfur, in addition to carbon as ring members. Specifically, piperidine, morpholine, thiomorpholine, piperazine, N-methylpiperazine, azetidine, 2-oxoazetidine, 2-oxopyrrolidine, 2-oxopiperidine, etc. can be mentioned.

In the above formulas (I) and (II), Ar is preferably selected from among (i) C$_{6-14}$aryl groups, (ii) 5- to 11-membered monocyclic or fused heteroaromatic groups each containing 1 or more heteroatoms selected from nitrogen, sulfur and oxygen in addition to carbon as ring members, and (iii) quinone groups, each unsubstituted or optionally substituted. More preferred are phenyl, 1-naphthyl, 2-naphthyl, 2-quinolyl, 3-quinolyl, 4-quinolyl, 1-isoquinolyl, 4-isoquinolyl, 2-benzothiazolyl, 2-benzoxazolyl, 2-benzimidazolyl, 2-pyridothiazolyl, p-benzoquinon-2-yl, 1,4-naphthoquinon-2-yl, anthraquinolyl, 5,6-chrysenequinolyl and 5,8-dioxo-5,8-dihydroquinolin-6-yl, each of which may be substituted by 1–4 substituents selected from among i) nitro, ii) optionally halogenated C$_{1-6}$alkyl, iii) optionally halogenated C$_{1-6}$ alkoxy, iv) hydroxy, v) amino, vi) mono-C$_{1-6}$alkylamino, vii) di-C$_{1-6}$alkylamino, viii) optionally halogenated C$_{1-6}$alkylsulfonylamino, ix) C$_{6-10}$arylsulfonylamino which may be substituted by 1–3 halogen atoms or optionally halogenated C$_{1-6}$alkyl groups, and x) halogen. Particularly preferred are i) 2-quinolyl, ii) 4-quinolyl, iii) 1-isoquinolyl, and iv) a) p-benzoquinonyl and b) 1,4-naphthoquinonyl, each of which may be substituted by optionally halogenated C$_{1-6}$alkyl.

Q is preferably a C$_{2-8}$alkylene group. Particularly preferred are C$_{2-5}$alkylene groups, more preferably trimethylene [—(CH$_2$)$_3$—] or tetramethylene [—(CH$_2$)$_4$—].

R$^1$ is preferably hydrogen, cyano, an optionally substituted C$_{6-14}$aryl group, a group of the formula

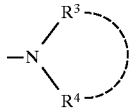

wherein each symbol has the same meaning as defined hereinbefore, or an acyl group of the formula —CO—O—R wherein R has the same meaning as defined hereinbefore (preferably C$_{1-6}$alkyl group). More preferred are cyano and optionally substituted C$_{6-14}$aryl group. Particularly preferred is cyano as well as (a) phenyl and (b) naphthyl each optionally having 1–3 substituents, preferably one substituent, as selected from among i) halogen, ii) optionally halogenated C$_{1-6}$alkyl, or iii) optionally halogenated C$_{1-6}$alkoxy. Most preferred are cyano and phenyl optionally having one i) halogen atom or ii) C$_{1-6}$alkoxy group.

R$^3$ is preferably hydrogen.

R$^4$ is preferably acyl. The acyl mentioned just above is preferably an acyl group which can be represented by either the formula —CO—R or the formula —SO$_2$—R (R is as defined hereinbefore). Particularly preferred are acyl groups in which R is C$_{1-6}$alkyl or C$_{6-14}$aryl which may be respectively substituted by halogen or C$_{1-6}$alkyl.

R$^2$ and R$^2$ each is preferably an acyl group which can be represented by —CO—R or —CO—NH—R wherein R is as defined hereinbefore. Particularly preferred are those groups in which R is hydrogen or any of (a) C$_{1-6}$alkyl, (b) C$_{3-6}$cycloalkyl and (c) C$_{6-14}$aryl which may respectively have 1–3 substituents selected from among i) halogen, ii) optionally halogenated C$_{1-6}$alkyl, iii) optionally halogenated C$_{1-6}$alkoxy, iv) C$_{1-6}$alkylcarbonyloxy and, v) C$_{6-14}$aryl which may be substituted by C$_{1-6}$alkyl or C$_{1-6}$alkoxy.

⋯⋯⋯preferably represents a single bond, and m is 2.

Preferred are compounds such that, in the above formula (I),

Ar represents phenyl, 1-naphthyl, 2-naphthyl, 2-quinolyl, 3-quinolyl, 4-quinolyl, 1-isoquinolyl, 4-isoquinolyl, 2-benzothiazolyl, 2-benzoxazolyl, 2-benz-imidazolyl, 2-pyridothiazolyl, p-benzoquinon-2-yl, 1,4-naphthoquinon-2-yl, anthraquinonyl, 5,6-chrysenequinonyl or 5,8-dioxo-5,8-dihydroquinolin-6-yl, which may have 1–4 substituents selected from among i) nitro, ii) optionally halogenated C$_{1-6}$alkyl, iii) optionally halogenated C$_{1-6}$alkoxy, iv) hydroxy, v) amino, vi) mono-C$_{1-6}$alkylamino, vii) di-C$_{1-6}$ alkylamino, viii) optionally halogenated C$_{1-6}$alkylsulfonylamino, ix) C$_{6-10}$ arylsulfonylamino optionally substituted by 1–3 halogen atoms or optionally halogenated C$_{1-6}$alkyl groups, and x) halogen, Q represents C$_{2-8}$alkylene, R$^1$ represents cyano or either (a) phenyl or (b) naphthyl which may have 1 to 3 substituents selected from among i) halogen, ii) optionally halogenated C$_{1-6}$alkyl, and iii) optionally halogenated C$_{1-6}$alkoxy, R$^3$ represents hydrogen, R represents an acyl group of the formula —CO—R or the formula —SO$_2$—R wherein R is as defined hereinbefore (preferably, R is a C$_{1-6}$alkyl or C$_{6-14}$aryl group which may be substituted by halogen or C$_{1-6}$alkyl), $R^2$ represents an acyl group of the formula —CO—R or —CO—NH—R wherein R is as defined hereinbefore (preferably R is hydrogen or a (a) $C_{1-6}$alkyl, (b) $C_{3-6}$cycloalkyl or (c) $C_{6-14}$aryl group which may have 1–3 substituents selected from among i) halogen, ii) optionally halogenated $C_{1-6}$alkyl, iii) optionally halogenated $C_{1-6}$alkoxy, iv) $C_{1-6}$alkylcarbonyloxy, and v) $C_{6-14}$aryl which may be substituted by $C_{1-6}$alkyl or $C_{1-6}$alkoxy, ......... represents a single bond, and m is 2.

Preferred among compounds of formula (II) are those in which $R^1$ is cyano, optionally substituted $C_{6-14}$aryl, a group of the formula:

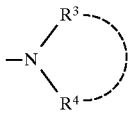

wherein each symbol has the same meaning as defined hereinbefore or acyl and $R^{2'}$ is acyl.

Still more preferred are compounds in which

Ar represents phenyl, 1-naphthyl, 2-naphthyl, 2-quinolyl, 3-quinolyl, 4-quinolyl, 1-isoquinolyl, 4-isoquinolyl, 2-benzothiazolyl, 2-benzoxazolyl, 2-benz-imidazolyl, 2-pyridothiazolyl, p-benzoquinon-2-yl, 1,4-naphthoquinon-2-yl, anthraquinolyl, 5,6-chrysenequinolyl or 5,8-dioxo-5,8-dihydroquinolin-6-yl, each of which may have 1–4 substituents selected from among i) nitro, ii) optionally halogenated $C_{1-6}$alkyl, iii) optionally halogenated $C_{1-6}$alkoxy, iv) hydroxy, v) amino, vi) mono-$C_{1-6}$alkylamino, vii) di-$C_{1-6}$alkylamino, viii) optionally halogenated $C_{1-6}$alkylsulfonylamino, ix) $C_{6-10}$arylsulfonylamino optionally substituted by 1–3 halogen atoms or optionally halogenated $C_{1-6}$alkyl groups, and x) halogen, Q represents $C_{2-8}$alkylene, $R^1$ represents cyano or either (a) phenyl or (b) naphthyl which may have 1 to 3 substituents selected from among i) halogen, ii) optionally halogenated $C_{1-6}$ alkyl, and iii) optionally halogenated $C_{1-6}$alkoxy, $R^3$ represents hydrogen, $R^4$ represents an acyl group of the formula —CO—R or the formula —SO$_2$—R wherein R is as defined hereinbefore (preferably, R is a $C_{1-6}$alkyl or $C_{6-14}$aryl group which may be substituted by halogen or $C_{1-6}$alkyl), $R^{2'}$ represents an acyl group of the formula —CO—R or —CO—NH—R wherein R is as defined hereinbefore (preferably R is hydrogen or a (a) $C_{1-6}$alkyl, (b) $C_{3-6}$cycloalkyl or (c) $C_{6-14}$aryl group which may have 1–3 substituents selected from among i) halogen, ii) optionally halogenated $C_{1-6}$alkyl, iii) optionally halogenated $C_{1-6}$ alkoxy, iv) $C_{1-6}$alkylcarbonyloxy, and v) $C_{6-4}$aryl which may be substituted by $C_{1-6}$alkyl or $C_{1-6}$alkoxy, ......... represents a single bond, and m is 2.

Also preferred are compounds in which

Ar represents p-benzoquinonyl, 1,4-naphthoquinon-2-yl, anthraquinonyl, 5,6-chrysenequinonyl or 5,8-dioxo-5, 8-dihydroquinolin-6-yl, each of which may have 1–4 substituents selected from among i) nitro, ii) optionally halogenated $C_{1-6}$alkyl, iii) optionally halogenated $C_{1-6}$alkoxy, iv) hydroxy, v) amino, vi) mono-$C_{1-6}$alkylamino, vii) di-$C_{1-6}$alkylamino, viii) optionally halogenated $C_{1-6}$alkylsulfonylamino, ix) $C_{6-10}$arylsulfonylamino optionally substituted by 1–3 halogen atoms or optionally halogenated $C_{1-6}$alkyl groups, and x) halogen, $R^1$ represents (a) phenyl or (b) naphthyl, which may have 1–3 substituents selected from among i) halogen, ii) optionally halogenated $C_{1-6}$alkyl, and iii) optionally halogenated $C_{1-6}$alkoxy, and $R^2$ or $R^{2'}$ represents an acyl group of the formula: —CO—R or —CO—NH—R wherein R is as defined hereinbefore.

Also preferred are the compounds in which $R^1$ represents cyano and $R^2$ and $R^{2'}$ represents an acyl group of the formula: —CO—R or —CO—NH—R wherein R is as defined hereinbefore.

It is also preferable that

Ar represents 2-quinolyl, 3-quinolyl, 4-quinolyl, 1-isoquinolyl or 4-isoquinolyl, each of which may have 1–4 substituents selected from among i) nitro, ii) optionally halogenated $C_{1-6}$alkyl, iii) optionally halogenated $C_{1-6}$alkoxy, iv) hydroxy, v) amino, vi) mono-$C_{1-6}$alkylamino, vii) di-$C_{1-6}$alkylamino, viii) optionally halogenated $C_{1-6}$alkylsulfonylamino, ix) $C_{6-10}$arylsulfonylamino which may be substituted by 1–3 halogen atoms or optionally halogenated $C_{1-6}$alkyl groups, and x) halogen and $R^1$ represents hydrogen.

Particularly preferred are compounds in which Ar is a p-benzoquinon-2-yl or 1,4-naphthoquinon-2-yl group which may be substituted by 1 to 4 substituents selected from the group consisting of i) halogen, ii) optionally halogenated $C_{1-6}$alkyl and iii) optionally halogenated $C_{1-6}$alkoxy, $R^1$ is a phenyl group which may be substituted by 1 to 3 substituents selected from the group consisting of halogen, optionally halogenated $C_{1-6}$alkyl and optionally halogenated $C_{1-6}$alkoxy, and $R^2$ is an acyl group of the formula: —CO—R wherein R is a $C_{1-6}$alkyl, $C_{3-6}$cycloalkyl or phenyl group which may be substituted by 1 to 3 halogen.

The following is a partial list of the preferred species of the above compound.

6-(1-Isoquinolyl)hexanohydroxamic acid, 7-(1-Isoquinolyl)heptanohydroxamic acid, 6-Phenyl-6-(2-quinolyl)hexanohydroxamic acid, 7-Phenyl-7-(2-quinolyl)heptanohydroxamic acid, 7-Cyano-7-(2-naphthyl)heptanohydroxamic acid, 7-(Benzothiazol-2-yl)-7-cyanoheptanohydroxamic acid, 7-(4-Methoxyphenyl)-7-(3-methyl-1,4-naphthoquinon-2-yl)heptanohydroxamic acid, 7-(3-Methyl-1,4-naphthoquinon-2-yl)-7-phenylheptanohydroxamic acid, O-Acetyl-6-(4-methoxyphenyl)-6-(3-methyl-1,4-naphthoquinon-2-yl)hexanohydroxamic acid, O-Propionyl-6-(4-methoxyphenyl)-6-(3-methyl-1,4-naphthoquinon-2-yl)hexanohydroxamic acid, O-Isobutyryl-6-(4-methoxyphenyl)-6-(3-methyl-1,4-naphthoquinon-2-yl)hexanohydroxamic acid, O-Benzoyl-6-(4-methoxyphenyl)-6-(3-methyl-1,4-naphthoquinon-2-yl)hexanohydroxamic acid, O-Ethylcarbamoyl-6-(4-methoxyphenyl)-6-(3-methyl-1, 4-naphthoquinon-2-yl)hexanohydroxamic acid, O-Acetyl-7-cyano-7(2-naphthyl)heptanohydroxamic acid, O-Propionyl-7-cyano-7(2-naphthyl)heptanohydroxamic acid, O-Benzoyl-7-cyano-7(2-naphthyl)heptanohydroxamic acid,
O-Benzoyl-6-(benzoxazol-2-yl)hexanohydroxamic acid,
O-Benzoyl-7-(benzothiazol-2-yl)heptanohydroxamic acid,
O-Propionyl-6-(benzoxazol-2-yl)hexanohydroxamic acid,
O-Acetyl-7-(2-quinolyl)heptanohydroxamic acid,
O-Propionyl-7-(2-quinolyl)heptanohydroxamic acid,
O-Propionyl-7-(4-methoxyphenyl)-7-(3-methyl-1,4-naphthoquinon-2-yl)heptanohydroxamic acid,
O-Benzoyl-7-(4-methoxyphenyl)-7-(3-methyl-1,4-naphthoquinon-2-yl)heptanohydroxamic acid,
O-Propionyl-7-(3-methyl-1,4-naphthoquinon-2-yl)-7-phenylheptanohydroxamic acid,
O-Propionyl-7-(4-fluorophenyl)-7-(3-methyl-1,4-naphthoquinon-2-yl)heptanohydroxamic acid.

More preferred are
O-propionyl-6-(4-methoxyphenyl)-6-(3-methyl-1,4-naphthoquinon-2-yl)hexanohydroxamic acid,
O-propionyl-7-(4-methoxyphenyl)-7-(3-methyl-1,4-naphthoquinon-2-yl)heptanohydroxamic acid,
O-acetyl-6-(4-methoxyphenyl)-6-(3-methyl-1,4-naphthoquinon-2-yl)hexanohydroxamic acid,
O-propionyl-7-(4-fluorophenyl)-7-(3-methyl-1,4-naphthoquinon-2-yl)heptanohydroxamic acid, and
O-benzoyl-6-(4-methoxyphenyl)-6-(3-methyl-1,4-naphthoquinon-2-yl)hexanohydroxamic acid, or a salt thereof.

As the salts of compound (I) and compound (II) of the present invention, the respective salts with inorganic bases, organic bases, inorganic acids, organic acids or basic or acidic amino acids can be mentioned. As preferred salts with inorganic bases, the corresponding salts with alkali metals such as sodium and potassium, salts with alkaline earth metals such as calcium and magnesium, aluminum salts and ammonium salts can be mentioned. As preferred salts with organic bases, the corresponding salts with trimethylamine, triethylamine, pyridine, picoline, ethanolamine, diethanolamine, triethanolamine, dicyclohexylamine, N,N'-dibenzylethylenediamine, etc. can be mentioned. As preferred salts with inorganic acids, there can be mentioned the corresponding salts with hydrochloric acid, hydrobromic acid, nitric acid, sulfuric acid, phosphoric acid, and so forth. As preferred salts with organic acids, the corresponding salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. can be mentioned. As preferred salts with basic amino acids, the corresponding salts with arginine, lysine, ornithine, etc. can be mentioned. As preferred salts with acidic amino acids, the corresponding salts with aspartic acid, glutamic acid, etc. can be mentioned.

Particularly preferred are pharmacologically acceptable salts. Thus, where the compound has a basic function, inorganic salts such as hydrochloride, sulfate, phosphate, hydrobromide, etc. and organic salts such as acetate, maleate, fumarate, succinate, methanesulfonate, p-toluenesulfonate, citrate, tartrate, etc. can be selected. Where an acidic function is available, inorganic salts such as salts with alkali metals (e.g. sodium, potassium, etc.) or alkaline earth metals (e.g. calcium, magnesium, etc.) and ammonium salts can be selected.

Processes for producing compound (I) and compound (II) are now described.

Compound (I) and compound (II) can be synthesized typically by the process shown in the following reaction schema or any process analogous therewith.

The symbols used for each compound in the reaction schema have the same meanings as defined hereinbefore.

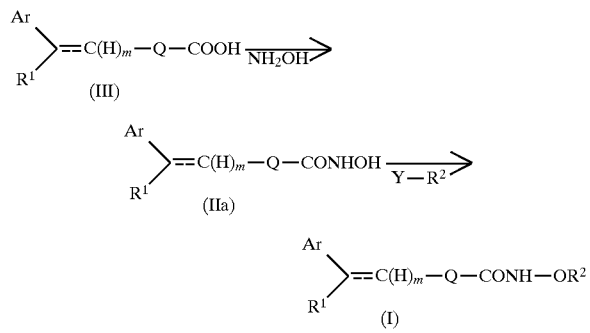

Compound (I) can be obtained by acylating compound (IIa) or a salt thereof in the per se known manner.

By way of illustration, compound (IIa) or a salt thereof is reacted with a compound of the formula Y—$R^2$ wherein Y represents a leaving group; $R^2$ is as defined hereinbefore, or a salt thereof to give compound (I).

The "leaving group" of Y above includes, for example, halogen (e.g. Cl, Br, I, etc.), $C_{1-4}$alkylsulfonyloxy which may be substituted by 1–3 halogen atoms (e.g. methanesulfonyloxy, trifluoromethanesulfonyloxy, etc.), $C_{6-10}$arylsulfonyloxy which may be substituted by 1–4 halogen atoms (e.g. p-toluenesulfonyloxy, benzenesulfonyloxy, p-bromobenzenesulfonyloxy, mesitylenesulfonyloxy, etc.), $C_{1-6}$alkoxy (e.g. methoxy, ethoxy, propoxy, isopropoxy, butoxy, etc.), and $C_{6-10}$aryloxy which may have 1–3 substituents selected from among halogen, nitro, etc. (e.g. phenoxy, p-chlorophenoxy, p-nitrophenoxy, etc.).

This acylation reaction can be carried out by per se known procedures, inter alia the procedures described in Journal of Organic Chemistry, 20, 782, 1961. For example, compound (IIa) or a salt thereof, or a reactive derivative thereof, is reacted with a compound of the formula Y—$R^2$ (both symbols are as defined hereinbefore) or a salt thereof in the presence of a base.

The reactive derivative mentioned above includes the corresponding acid anhydride, acid halide, activated ester, lower alkyl ester, and so forth.

The base mentioned above includes alkylamines such as triethylamine, diisopropylethylamine, etc. and nitrogen-containing heteroaromatic compounds such as pyridine, among others.

The proportion of the compound Y—$R^2$ or a salt thereof relative to compound (IIa) is about 1–1.2 equivalents.

The amount of the base relative to the compound Y—$R^2$ is about 1–3 equivalents.

The solvent for this reaction can be any solvent that does not interfere with the reaction, thus including nitrites (e.g. acetonitrile etc.), halogenated hydrocarbons (e.g. dichloromethane, chloroform, etc.), and ethers (e.g. diethyl ether, tetrahydrofuran, dioxane, isopropyl ether, 1,2-dimethoxyethane, etc.), among others.

The reaction temperature is about −20° C. to room temperature and is preferably room temperature. The reaction time can be tailored to the reactants or reagents and may for example be about 0.2–5 hours.

The reaction may also be conducted by dissolving both compound (IIa) and an approximately equimolar amount of the corresponding organic acid (compound of the formula $R^2$—OH) in an inert solvent (e.g. a halogenated hydrocarbon, acetonitrile or the like) and reacting then in the presence of about 1–1.5 equivalents of a dehydrative condensing agent such as dicyclohexylcarbodiimide. The reaction temperature is about −20° C. to room temperature and the reaction time is about 6–12 hours.

The carbamoylation reaction can be carried out substantially under the same conditions as the above acylation reaction. The base mentioned above is not essential.

Compound (IIa) can be synthesized from the corresponding carboxylic acid (III) or a salt thereof typically by the procedures described in JP-A-1 104033 and S. Patai (ed.): Supplement B, The Chemistry of Acid Derivatives, Vol. 2 (John Wiley & Sons), 849–873 (1992).

For example, compound (III) is converted to a reactive derivative of its carboxyl function, which is then reacted with hydroxylamine in the presence of a base at 0°–50° C., preferably room temperature (0°–30° C.), for about 10 minutes to about 2 hours to provide compound (IIa).

The reactive derivative mentioned above may for example be the acid anhydride, acid halide, or activated ester.

The base mentioned above includes alkali metal or alkaline earth metal salts of hydrogencarbonic acid, such as sodium hydrogen carbonate, potassium hydrogen carbonate, etc., alkali metal or alkaline earth metal salts of carbonic acid, such as sodium carbonate, potassium carbonate, etc., alkali metal or alkaline earth metal hydroxides such as sodium hydroxide, potassium hydroxide, calcium hydroxide, etc., and organic bases such as triethylamine, diisopropylethylamine, etc.

The proportion of hydroxylamine relative to compound (III) is at least 1 equivalent and preferably about 2–5 equivalents. The proportion of the base relative to hydroxylamine is not less than 2 equivalents and preferably about 4–10 equivalents.

The solvent for this reaction can be any solvent that does not interfere with the reaction, thus including water, alcohols (e.g. methanol, ethanol, n-propanol, isopropyl alcohol, etc.), nitrites (e.g. acetonitrile etc.), halogenated hydrocarbons (e.g. dichloromethane, chloroform, etc.), and ethers (e.g. diethyl ether, tetrahydrofuran, dioxane, etc.), among others. These solvents can be used each alone or in a suitable combination.

The reaction temperature may range from about 0° C. to about 50° C. and is preferably room temperature. The reaction time is about 10 minutes to about 2 hours.

Compound (IIa) can also be obtained by reacting a lower alkyl ester of compound (III) with hydroxylamine in the presence of a base. This reaction can be carried out by any of known procedures, typically in accordance with the procedures described in Shin Jikken Kagaku Koza (edited by The Chemical Society of Japan), Vol. 14, 1227.

The base that can be used for the above reaction includes strong bases such as alkali metal or alkaline earth metal hydrides (e.g. lithium hydride, sodium hydride, potassium hydride, calcium hydride, etc.), alkali metal or alkaline earth metal amides (e.g. lithium amide, sodium amide, lithium diisopropylamide, lithium dicyclohexylamide, lithium hexamethylsilazide, sodium hexamethylsilazide, potassium hexamethylsilazide, etc.) and alkali metal or alkaline earth metal (lower)alkoxides (e.g. sodium methoxide, sodium ethoxide, potassium t-butoxide, etc.); inorganic bases such as alkali metal or alkaline earth metal hydroxides (e.g. sodium hydroxide, potassium hydroxide, lithium hydroxide, barium hydroxide, etc.), alkali metal or alkaline earth metal carbonates (e.g. sodium carbonate, potassium carbonate, cesium carbonate, etc.), and alkali metal or alkaline earth metal hydrogen carbonates (e.g. sodium hydrogen carbonate, potassium hydrogen carbonate, etc.); and organic bases such as various amines, e.g. triethylamine, diisopropylethylamine, N-methylmorpholine, dimethylaminopyridine, 1,8-diazabicyclo[5.4.0]-7-undecene (DBU), 1,5-diazabicyclo[4.3.0]non-5-ene (DBN), etc. and basic heteroaromatic compounds such as pyridine, imidazole, 2,6-lutidine, and so on. Preferred among these bases are strong bases such as alkali metal or alkaline earth metal (lower)alkoxides (e.g. sodium methoxide, sodium ethoxide, potassium t-butoxide, etc.).

The proportion of hydroxylamine relative to the lower alkyl ester is not less than equimolar and preferably about 3–20 equivalents.

The proportion of the base should be a stoichiometric excess relative to hydroxylamine and may for example be about 1.2–2 equivalents on the same basis.

The solvent for this reaction can be any solvent that does not interfere with the reaction, thus including but being not limited to alcohols (e.g. methanol, ethanol, n-propanol, isopropyl alcohol, tert-butanol, ethylene glycol, sec-butanol, etc.) and ethers (e.g. diethyl ether, tetrahydrofuran, dioxane, etc.). These solvents can be used each alone or as a suitable mixture of two or more species.

The reaction temperature may range from about −20° C. to about 50° C. and is preferably room temperature. The reaction time is about 1–18 hours.

Compound (III) can be synthesized by any of per se known processes.

The compound (III) wherein $R^1$ is a quinone group can be synthesized typically by the process described in JP-A-61 44840 or any process analogous therewith.

The compound (III) wherein $R^1$ is an aromatic group other than a quinone group can be synthesized typically by any of the processes described in JP-A-63 47707 and JP-A-59 101465 or any process analogous therewith.

The compound (III) wherein $R^1$ is cyano or aryl and m is 1 can be synthesized typically by the process described in JP-A-59 101465 or any process analogous therewith.

The compound (III) wherein $R^1$ is cyano or aryl and m is 2 can be synthesized typically in accordance with the following reaction schema or any process analogous therewith.

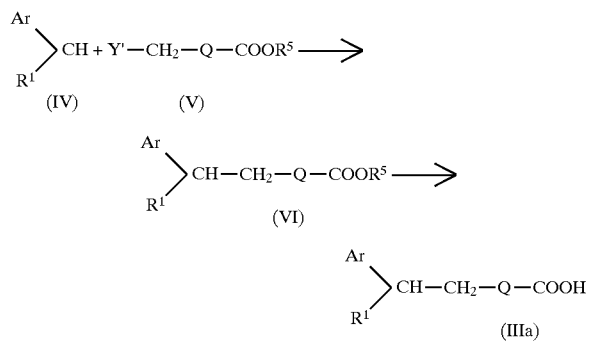

In the above formulas, $R^5$ represents lower alkyl, Y' represents a leaving group, and the other symbols are as defined hereinbefore.

The "lower alkyl" of $R^5$ above typically includes $C_{1-6}$ alkyl groups (e.g. methyl, ethyl, propyl, isopropyl, butyl, etc.). The "leaving group" of Y' may be any of the species mentioned for the "leaving group" designated by Y.

Compound (IIIa) can be obtained by reacting compound (IV) or a salt thereof with compound (V) or a salt thereof and hydrolyzing the resulting compound (VI) or salt thereof.

The above substitution reaction is carried out with advantage in the presence of a base.

The base mentioned just above may be any of the strong bases, inorganic bases and organic bases mentioned above.

The proportion of the base relative to compound (IV) is about 1–5 equivalents and preferably about 1–3 equivalents. The proportion of compound (V) relative to compound (IV) is about 1–3 equivalents.

The solvent for this reaction can be any solvent that does not interfere with the reaction, thus including alcohols (e.g. methanol, ethanol, etc.), ethers (e.g. diethyl ether, tetrahydrofuran (THF), dioxane, etc.), halogenated hydrocarbons (e.g. dichloromethane, 1,2-dichloroethane, chloroform, carbon tetrachloride, etc.), aromatic hydrocarbons (e.g. benzene, toluene, xylene, etc.), nitriles (e.g. acetonitrile etc.), acid amides (e.g. N,N-dimethylformamide etc.), ketones (e.g. acetone, methyl ethyl ketone, etc.), and sulfoxides (e.g. dimethyl sulfoxide etc.). These solvents can be used each alone or as a mixture of 2 or more species. Particularly preferred are ethers (e.g. THF, diethyl ether, etc.), nitriles (e.g. acetonitrile etc.), acid amides (e.g. N,N-dimethylformamide etc.) and ketones (e.g. acetone etc.).

The reaction temperature may range from about 0° C. to about 100° C. and is preferably about 10°–50° C. The reaction time may range from about 5 minutes to about 100 hours and is preferably about 1–5 hours.

The hydrolysis of compound (VI) can be carried out by any per se known method for hydrolysis using an acid or a base. This hydrolysis reaction process may include a deprotection step.

For hydrolysis with a base, compound (VI) is reacted with a base (e.g. a metal hydroxide such as lithium hydroxide, sodium hydroxide, potassium hydroxide, barium hydroxide, etc.) in a solvent (e.g. any or a mixture of water, alcohol and ether). The preferred solvent is a mixture of water and methanol. The preferred alkali is sodium hydroxide.

The proportion of the alkali relative to compound (VI) is about 2–100 equivalents and preferably about 5–10 equivalents.

The reaction temperature is about 10°–120° C. and preferably about 50°–120° C. The reaction time may range from about 5 minutes to about 100 hours and is preferably about 10–50 hours. The preferred reaction parameters are: solvent=water-methanol, reaction temperature about 50°–120° C., reaction time about 10–50 hours.

For acid hydrolysis, compound (VI) is treated with a stoichiometric excess of diluted hydrochloric acid or diluted HCl-acetic acid with stirring at room temperature to 120° C. for 0.5–18 hours.

Many species of compound (IV) are readily available from commercial sources.

The compound (III) wherein $R^1$ represents

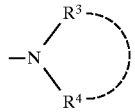

wherein the respective symbols are as defined herein-before, can be produced typically in accordance with the following reaction schema or any process analogous therewith.

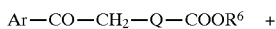

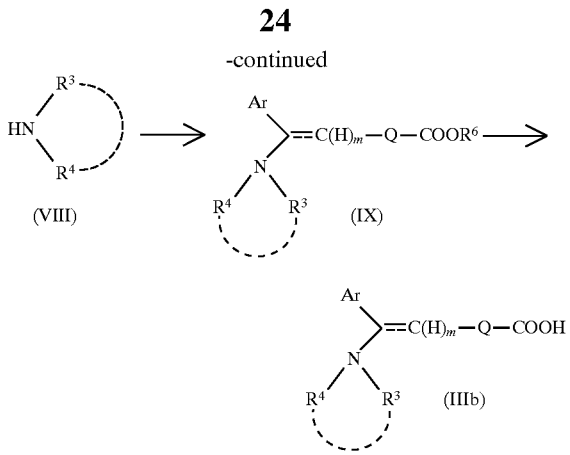

In the above formulas, $R^6$ represents lower alkyl; the other symbols are as defined hereinbefore.

The "lower alkyl" of $R^6$ above can be typically any of the $C_{1-6}$alkyl groups mentioned for $R^5$.

The compound (IIIb) in which m is 1 can be obtained by subjecting compound (VII) or a salt thereof to dehydrative condensation with compound (VIII) or a salt thereof and hydrolyzing the resulting compound (IX) or salt thereof. To obtain the compound (IIIb) in which m is 2, the reduction reaction is carried out in the same system or immediately following the dehydration reaction.

The above dehydration reaction can be carried out by a Der se known procedure, e.g. heating the reactants in an inert solvent in the presence of an acid catalyst (e.g. about 1–1.5 equivalents of p-toluenesulfonic acid or the like) at about 40°–100° C. for about 1–10 hours.

The reduction reaction mentioned above can be carried out by a per se known procedure, e.g. treating the substrate compound in an inert solvent in the presence of a metal catalyst (e.g. palladium-on-carbon) under a hydrogen pressure of about 1–10 atms. for about 1–10 hours. As an alternative, this reduction reaction can be carried out using a metal hydride (e.g. [sodium]cyanoborohydride). In this case, the reaction can be carried out in an alcoholic solvent (e.g. methanol, ethanol, etc.) using about 1–5 equivalents of the metal hydride at room temperature to 50° C. for 1–24 hours.

The hydrolysis reaction mentioned above can be carried out under the same conditions as mentioned for hydrolysis of compound (VI).

In the respective reactions according to the present invention and the respective reactions for synthesizing the starting compounds to be used, wherein any starting compound contains an amino group, a carboxyl group, or a hydroxyl group, such functional groups may be protected beforehand using protective groups which are conventionally used in peptide and other fields of chemistry, and the respective objective compounds can be obtained by removing the protective groups as necessary after the respective synthetic reactions.

The protective group that can be used for masking an amino group includes but is not limited to $C_{1-6}$ alkylcarbonyl (e.g. formyl, acetyl, ethylcarbonyl, etc.), $C_{1-6}$alkyloxy-carbonyl (e.g. methoxycarbonyl, ethoxycarbonyl, etc.), benzoyl, $C_{7-10}$aralkyl-carbonyl (e.g. benzylcarbonyl etc.), trityl, phthaloyl, and N,N-dimethylaminomethylene. Each of these groups may have 1–3 substituents selected from among halogen (e.g. F, Cl, Br, I), nitro, etc.

The protective group that can be used for masking a carboxyl group includes but is not limited to $C_{1-6}$alkyl (e.g.

methyl, ethyl, n-propyl, isopropyl, butyl, tert-butyl, etc.), phenyl, trityl, and silyl. Each of these groups may have 1–3 substituents such as halogen (e.g. F, Cl, Br, I), $C_{1-6}$alkylcarbonyl (e.g. formyl, acetyl, propionyl, butylcarbonyl, etc.), nitro, and other groups.

The protective group that can be used for masking a hydroxyl group includes, for example, $C_{1-6}$alkyl (e.g. methyl, ethyl, n-propyl, isopropyl, butyl, tert-butyl, etc.), phenyl, $C_{7-10}$aralkyl (e.g. benzyl etc.), $C_{1-6}$alkylcarbonyl (e.g. formyl, acetyl, propionyl, etc.), benzoyl, $C_{7-10}$aralkyl-carbonyl (e.g. benzylcarbonyl etc.), tetrahydropyranyl, tetrahydrofuranyl, and silyl. Each of these groups may have 1–3 substituents selected from among halogen (e.g. F, Cl, Br, I), $C_{1-6}$alkyl (e.g. methyl, ethyl, n-propyl, etc.), phenyl, $C_{7-10}$aralkyl (e.g. benzyl etc.), nitro, and other groups.

Removal of such protective groups can be carried out by per se known procedures or any other procedures analogous therewith. For example, the procedure using an acid or a base, the reductive deprotection method, or the method utilizing UV light or a chemical reagent such as hydrazine, phenylhydrazine, sodium N-methyldithiocarbamate, tetrabutylammonium fluoride or palladium acetate can be mentioned.

The compounds (I) and (II) of the present invention can respectively be isolated and purified by known procedures such as solvent extraction, pH adjustment, redistribution, crystallization or precipitation, recrystallization, chromatography, etc. The starting compounds and salts for the compounds (I) and (II) of the invention can also be isolated and purified by the same known procedures as above but the respective reaction mixtures containing them can be directly submitted to the contemplated reactions, omitting the purification procedures.

Where the compound (I) of the present invention includes optical isomers, stereoisomers, positional isomers, and/or rotational isomers, such isomers also fall within the scope of the present invention. Where compound (I) or compound (II) includes optical isomers, stereoisomers, positional isomers, or rotamers, the respective isomers can be obtained as simple substances by using the per se known synthetic or fractionation procedures. Where the compound of the invention exists as optical isomers for instance, the respective isomers obtainable by optical resolution also fall within the scope of the invention.

Optical isomers can be produced by per se known methods. Specifically, optically active synthetic intermediates are employed or the end-product racemic mixtures are respectively subjected to a routine optical resolution procedure to provide the optical isomers.

For optical resolution, the fractional recrystallization method, the method using a chiral column, or the diastereomer method can be employed.

1) Fractional recrystallization method

The racemic compound is reacted with an optically active compound to give the optically active salt which is then isolated by fractional recrystallization. If desired, it is neutralized to provide the free optical isomer.

2) The method utilizing a chiral column

The racemic compound or a salt thereof is fractionated by means of a chiral column. In the case of liquid column chromatography, a mixture of optical isomers is applied to a chiral column such as ENANTIOOVM (Tosoh Corporation) and developed with any or a mixture of solvents, e.g. water, buffers (e.g. phosphate buffer), and organic solvents (e.g. ethanol, methanol, acetonitrile, etc.), to isolate the optical isomers. In the case of gas chromatography, a chiral column for gas chromatography, such as CP-Chirasil-Dex CB (G. L. Science), is employed.

3) Diastereomer method

The racemic compound is reacted with an optically active reagent to give a mixture of diastereomers. This mixture is then subjected to a routine fractionation procedure (e.g. fractional recrystallization or chromatography) to give simple substances. Then, the optically active reagent moiety is cleaved off by hydrolysis or other chemical treatment to provide the desired optical isomers. For example, where the compound of the invention contains a hydroxyl group or a primary or secondary amino group, the compound is subjected to condensation reaction with an optically active organic acid (e.g. MPTA [α-methoxy-α-(trifluoromethyl) phenylacetic acid], (−)-menthoxyacetic acid, etc) to give the ester or amide diastereomers. Where the compound of the invention has a carboxyl group, the compound is subjected to condensation reaction with an optically active amine or alcohol reagent to give the amide or ester diastereomers. The diastereomers thus obtained can be subjected to acid or basic hydrolysis to give the optical isomers of the original compound.

The compounds (I) and (II) of the present invention have several meritorious activities such as cerebral neuronal degeneration neutralizing activity, brain tissue injury neutralizing activity, and inhibitory activity against production of cytokines (e.g. IL-1β, TNFα, etc.) from human macrophages and cerebral cells. Therefore, these compounds are of value as an anti-neurodegenerative agent for mammalian animals (e.g. man, equine, bovine, dog, cat, rat, mouse, monkey, etc.) and can find application in the treatment, prevention or improved prognosis of neurodegradation-associated functional disorders such as neurodegenerative diseases (e.g. Alzheimer's disease, Parkinson's disease, Down's syndrome, Pick's disease, Creutzfeldt-Jakob disease, multiple sclerosis and bacterial or viral meningitis such as Borna disease, postvaccination encephalitis, AIDS-associated encephalopathy, etc.), and brain dysfunctions (e.g. cerebral infarction, cerebral hemorrhage, subarachnoid hemorrhage, trauma, etc.), among other diseases.

The compounds (I) and (II) of the present invention are also effective in palliating cytokine-associated symptoms such as general malaise, pyrexia, sleep, headache, arthralgia, anorexia, etc. and mental symptoms such as depression in the above-mentioned mammalian animals.

Furthermore, the compounds (I) and (II) of the present invention are capable of arresting the abnormal release of nitric oxide due to activation of the immune system in the mammals and, therefore, are of value for palliating septic shock, nephritis, atherosclerosis, asthma, diabetes and bone diseases.

The compounds (I) and (II) of the present invention have only a low toxic potential and can, therefore, be safely administered either as they are or in various dosage forms prepared using pharmacologically acceptable carriers, such as tablets (inclusive of dragees and film-coated tablets), powders, granules, capsules (inclusive of soft capsules), solutions, injections, suppositories, and controlled-release or other drug delivery systems, either orally or by routes other than peroral (e.g. local, rectal, intravenous, etc.). The amount of compound (I) or (II) in the pharmaceutical dosage form of the present invention is 0.1 to 100 parts by weight based on the total composition. The dosage depends on the subject of administration, the route of administration, the disease to be managed, and other factors. For use as a therapeutic drug for neurodegeneration, about 0.1 to 500 mg, preferably about 1–100 mg, more preferably about 5–100 mg, as the active compound, can be orally administered daily for the average human adult (b. wt. 60 kg). The above dosage can be administered in a few divided doses daily.

The pharmacologically acceptable carrier that can be used for the manufacture of the pharmaceutical composition of the present invention includes a variety of organic and inorganic carriers which are conventionally used in pharmaceutical practice. Thus, the excipient, lubricant, binder, disintegrator, etc. can be used for solid dosage forms and the solvent, solubilizer, suspending agent, isotonizing agent, buffer, soothing agent (local anesthetic), etc. can be used for liquid dosage forms. Where necessary, a variety of additives such as the preservative, antioxidant, coloring agent, sweetener, adsorbent, wetting agent, etc. can also be included in the formulations.

The excipient that can be used includes, for example, lactose, sucrose, D-mannitol, starch such as corn starch, crystalline cellulose, and light silicic anhydride.

The lubricant includes, for example, magnesium stearate, calcium stearate, talc, and colloidal silica.

The binder includes, for example, crystalline cellulose, sucrose, D-mannitol, dextrin, hydroxypropylcellulose, hydroxypropylmethylcellulose, polyvinylpyrrolidone, starch, sugar, gelatin, methylcellulose, and carboxymethylcellulose sodium.

The disintegrator that can be used includes, for example, starch, carboxymethylcellulose, carboxymethylcellulose calcium, croscarmellose, carboxymethylstarch sodium, and L-hydroxypropylcellulose.

The solvent includes, for example, water for injection, alcohol, propylene glycol, macrogols, sesame oil and corn oil.

The solubilizer includes, for example, polyethylene glycol, propylene glycol, D-mannitol, benzyl benzoate, ethanol, trisaminomethane, cholesterol, triethanolamine, sodium carbonate, and sodium citrate.

The suspending agent includes, for example, surfactants such as stearyltriethanolamine, sodium lauryl sulfate, laurylaminopropionic acid, lecithin, benzalkonium chloride, benzethonium chloride, glyceryl monostearate, etc. and hydrophilic macromolecular substances such as polyvinyl alcohol, polyvinylpyrrolidone, carboxymethylcellulose sodium, methylcellulose, hydroxymethylcellulose, hydroxyethylcellulose, and hydroxypropylcellulose.

The isotonizing agent includes, for example, glucose, D-sorbitol, sodium chloride, glycerol, and D-mannitol.

The buffer includes phosphate, acetate, carbonate, citrate and other buffers.

The soothing agent includes, for example, benzyl alcohol.

The preservative includes, for example, p-hydroxybenzoic acid esters, chlorobutanol, benzyl alcohol, phenylethyl alcohol, dehydroacetic acid, and sorbic acid.

The antioxidant includes, for example, sulfites and ascorbic acid.

EXAMPLE

The following reference, working, formulation and test examples are further illustrative of the present invention.

In the following reference and working examples, the term "room temperature" is used to mean the temperature range of 0° to 30° C. For drying purposes, anhydrous magnesium sulfate or anhydrous sodium sulfate was employed.

The abbreviations used in the examples have the following meanings.

s: singlet
d: doublet
t: triplet
q: quartet
m: multiplet
br: broad
J: coupling constant
Hz: Hertz
$CDCl_3$: deuterochloroform
THF: tetrahydrofuran
DMF: N,N-dimethylformamide
DMSO: dimethyl sulfoxide
IPE: diisopropyl ether
$^1$H-NMR: proton nuclear magnetic resonance (generally the free compound was used for this spectrometry)
Me: methyl
Et: ethyl
Pr: propyl
Bu: butyl
Ac: acetyl
Ph: phenyl
Ms: mesyl
Ts: tosyl Reference Example 1

Ethyl 7-(1-hydroxy-2-naphthyl)-7-oxo heptanoate

In methylene chloride (100 ml) was dissolved monoethyl heptanedioate (50 g) followed by dropwise addition of thionyl chloride (38 ml). The mixture was stirred at 50° C. for 2 hours and, then, concentrated to dryness. The residue and 1-naphthol (36.6 g) were dissolved in toluene (300 ml) and boron trifluoride-ether complex (43.3 g) was then added dropwise. After 3 hours of stirring, the reaction mixture was poured in cold water and extracted with diisopropyl ether. The organic layer was washed with water, dried, and concentrated to dryness. The residue was mixed with aluminum chloride (53.4 g) and xylene (300 ml) and the mixture was stirred at 130° C. for 1 hour. After spontaneous cooling, the supernatant was decanted off and the residue was diluted with 2N-HCl and extracted with ethyl acetate. The organic layer was washed, dried, and concentrated to dryness. The residue was refluxed with hydrogen chloride (22g) and ethanol (450 ml) for 3 hours. After spontaneous cooling, the precipitated crystals were harvested by filtration and rinsed with hexane-diisopropyl ether (9:1) to provide the title compound (62 g).

m.p. 77°–78° C.; $^1$ H-NMR ($CDCl_3$) δ: 1.26 (3H, t, J=7 Hz), 1.38–1.60 (2H, m), 1.60–1.90 (4H, m), 2.34 (2H, t, J=7 Hz), 3.07 (2H, t, J=7 Hz), 4.13 (2H, q, J=7 Hz), 7.27 (1H, d, J=9 Hz), 7.55 (1H, m), 7.63 (1H, m), 7.67 (1H, d, J=9 Hz), 7.77 (1H, br, d, J=7 Hz), 8.07 (1H, m).

Reference Example 2

Ethyl 7-(1-hydroxy-2-naphthyl)heptanoate

Using ethyl 7-(1-hydroxy-2-naphthyl)-7-oxo heptanoate (15 g), 10% palladium-on-carbon (1.5 g), triethylamine hydrochloride (6.6 g), triethylamine (4.86 g), and ethanol (300 ml), a catalytic hydrogenation reaction was carried out at atmospheric temperature and pressure for 5 days. The catalyst was then filtered off and the filtrate was concentrated under reduced pressure. The residue was diluted with ether, washed with water, 1N HCl, and saturated aqueous sodium chloride solution in that order, dried, and concentrated. The residue was applied to a silica gel column (hexane-ethyl acetate) and then recrystallized from ethyl acetate-hexane to provide the title compound (7.28 g).

m.p. 41°–42° C.; [1] H-NMR (CDCl$_3$) δ: 1.25 (3H, t, J=7 Hz), 1.25–1.50 (4H, m), 1.50–1.80 (4H, m), 2.30 (2H, t, J=7 Hz), 2.74 (2H, t, J=8 Hz), 4.13 (2H, q, J=7 Hz), 7.24 (1H, d, J=9 Hz), 7.35–7.55 (3H, m), 7.78 (1H, m), 8.13 (1H, m).

Reference Example 3

Ethyl 7-(2-hydroxy-1-naphthyl)-7-phenylheptanoate

2-Naphthol (1.152 g) and ethyl 7-hydroxy-7-phenyl-heptanoate (2g) were dissolved in methylene chloride (20 ml) followed by dropwise addition of boron trifluoride-ether complex (0.56 g). After 5 hours of stirring, the reaction mixture was extracted with chloroform and the extract was washed with water, dried, and concentrated. The residue was applied to a silica gel column (hexane-ethyl acetate) to provide the title compound (1.94 g).

[1] H-NMR (CDCl$_3$) δ: 1.22 (3H, t, J=7 Hz), 1.20–1.65 (6H, m), 2.20 (2H, t, J=7 Hz), 2.20–2.50 (2H, m), 4.09 (2H, q, J=7 Hz), 5.03 (1H, dd, J=9 Hz, 6 Hz), 7.01 (1H, d, J=9 Hz), 7.10–7.50 (7H, m), 7.67 (1H, d, J=9 Hz), 7.79 (1H, dd, J=8 Hz, 1 Hz), 8.05 (1H, br, d, J=9 Hz).

Reference Example 4

Ethyl 7-(4-chloro-1-hydroxy-2-naphthyl)-7-phenyl-heptanoate

Using 4-chloro-1-naphthol (3.57 g), the title compound (6.3 g) was synthesized in otherwise the same manner as above.

[1] H-NMR (CDCl$_3$) δ: 1.24 (3H, t, J=7 Hz), 1.25–1.50 (4H, m), 1.50–1.70 (2H, m), 2.12 (2H, q, J=7 Hz), 2.27 (2H, t, J=7 Hz), 4.12 (2H, q, J=7 Hz), 4.28 (1H, t, J=8 Hz), 7.15–7.40 (5H, m), 7.49 (1H, s), 7.43–7.65 (2H, m), 8.07–8.21 (2H, m).

Reference Example 5

Ethyl 7-(1-hydroxy-2-naphthyl)-7-phenylheptanoate

Using ethyl 7-(4-chloro-1-hydroxy-2-naphthyl)-7-phenylheptanoate (4.3 g), 10% palladium-on-carbon (0.4 g), ethanol (90 ml), and triethylamine (10 ml), a catalytic hydrogenation reaction was carried out at 50° C. and atmospheric pressure for 16 hours. The reaction mixture was then filtered and the filtrate was concentrated and applied to a silica gel column (hexane-ethyl acetate) to provide the title compound (3.65 g).

[1] H-NMR (CDCl$_3$) δ: 1.23 (3H, t, J=7 Hz), 1.20–1.45(4H, m), 1.50–1.70 (2H, m), 2.13 (2H, br, q, J=7 Hz), 2.25 (2H, t, J=7 Hz), 4.11 (2H, q, J=7 Hz), 4.32 (1H, t, J=8 Hz), 7.10–7.33 (5H, m), 7.36–7.50 (4H, m), 7.72–7.80 (1H, m), 8.02–8.10 (1H, m).

Reference Example 6

Ethyl 8-(isoquinolin-4-yl)octanoate

A solution of dimsyl sodium (8 ml) prepared from a suspension (40 ml) of sodium hydride (4 g) in DMSO was added dropwise to a suspension (10 ml) of 6-carboxyhexyltriphenylphosphonium bromide (4.7 g) in DMSO and the mixture was stirred for 10 minutes. Then, 4-formylisoquinoline (1.6 g) was added and the mixture was stirred at room temperature for 10 minutes. This reaction mixture was diluted with water (50 ml), washed with toluene (50 ml), adjusted to pH 5 with 2N HCl, and extracted with ethyl acetate. The organic layer was washed with water, dried, and concentrated under reduced pressure. After the residue was dissolved in ethanol (20 ml), thionyl chloride (2 ml) was added and the mixture was allowed to stand overnight. This mixture was concentrated under reduced pressure and the residue was dissolved in ethyl acetate and washed with saturated aqueous sodium hydrogen carbonate solution. The organic layer was washed with water, dried, and concentrated under reduced pressure. The residue was dissolved in ethyl acetate (10 ml) and the solution was stirred in the presence of Raney nickel under hydrogen gas at 1 atm. overnight. The catalyst was then filtered off and the filtrate was concentrated under reduced pressure and the residue was subjected to silica gel column chromatography using ethyl acetate-isopropyl ether (1:1) as eluent to provide the title compound (0.8 g).

Reference Example 7

8-(Isoquinolin-4-yl)octanoic acid

Ethyl 8-(isoquinolin-4-yl)octanoate (0.8 g) was dissolved in a mixture of methanol (10 ml) and water (5 ml) followed by addition of sodium hydroxide (1 g), and the mixture was stirred at room temperature for 1 hour. The reaction mixture was then concentrated under reduced pressure and the residue was adjusted to pH 5 with 2N-HCl and extracted with ethyl acetate. The organic layer was washed with water, dried, and concentrated under reduced pressure, and the resulting crude crystalline crop was recrystallized from ethyl acetate to provide the title compound (0.6 g).

m.p. 99°–100° C.; Elemental analysis for $C_{17}H_{21}NO_2$; Calcd.: C, 75.25; H, 7.80; N, 5.16; Found: C, 75.36; H, 7.84; N, 5.12; $^1$H-NMR (CDCl$_3$) δ: 9.15 (1H, s), 8.37 (1H, s), 8.01 (2H, m), 7.77 (1H, m), 7.61 (1H, m), 3.03 (2H, t, J=8 Hz), 2.37 (2H, t, J=8 Hz), 1.41–1.80 (10H, m)

Reference Example 8

7-(Isoquinolin-4-yl)heptanoic acid

The procedure of Reference Example 7 was substantially repeated to provide 7-(isoquinolin-4-yl)heptanoic acid. m.p. 108°–109° C.; Elemental analysis for $C_{16}H_{19}NO_2$; Calcd.: C, 74.68; H, 7.44; N, 5.44; Found: C, 74.68; H, 7.46; N, 5.46

Reference Example 9

6-(Isoquinolin-4-yl)hexanoic acid

The procedure of reference Example 7 was substantially repeated to provide 6-(isoquinolin-4-yl)hexanoic acid. m.p. 131°–132° C.; Elemental analysis for $C_{15}H_{17}NO_2$ Calcd.: C, 74.05; H, 7.04; N, 5.76 Found: C, 73.75; H, 7.08; N, 5.96

Reference Example 10

Ethyl (Z)-7-(2-quinolyl)-6-heptenoate

2-Quinolinecarbaldehyde (2 g) and (5-ethoxycarbonylpentyl)triphenylphosphonium bromide (12.5 g) were dissolved in dimethyl sulfoxide (50 ml) and a solution of potassium t-butoxide (2.92 g) in DMSO (10 ml) was added dropwise. The mixture was stirred for about 30 minutes, after which it was poured in iced water and extracted with ether. The organic layer was washed, dried, and concentrated, and the residue was applied to a silica gel column (hexane-ethyl acetate) to provide the title Z-isomer (1 g) together with the E-isomer (1.24 g).

Z-isomer:

oil

$^1$H-NMR (CDCl$_3$) δ: 1.23 (3H, t, J=7 Hz), 1.50–1.80 (4H, m), 2.33 (2H, t, J=7 Hz), 2.75 (2H, m), 4.12 (2H, q, J=7 Hz), 6.01 (1H, dt, J=12 Hz, 7 Hz), 6.66 (1H, dt, J=12 Hz, 2 Hz), 7.37 (1H, d, J=8 Hz), 7.49 (1H, m), 7.68 (1H, m), 7.78 (1H, br, J=8 Hz), 8.06 (1H, d, J=8 Hz), 8.10 (1H, d, J=8 Hz).

Reference Example 11

Ethyl (E)-7-(2-quinolinyl)-6-heptanoate

Ethyl (E)-7-(2-quinolinyl)-6-heptanoate was synthesized in the same manner as Reference Example 10.

oil $^1$H-NMR (CDCl$_3$) δ: 1.26 (3H, t, J=7 Hz), 1.50–1.90 (4H, m), 2.30–2.43 (4H, m), 4.13 (2H, q, J=7 Hz), 6.71 (1H, d, J=16 Hz), 6.82 (1H, dt, J=16 Hz, 7 Hz), 7.40–7.50 (1H, m), 7.52 (1H, d, J=8 Hz), 7.61–7.80 (2H, m), 8.00–8.11 (2H, m).

Reference Example 12

Ethyl 7-(2-quinolyl)heptanoate

Using ethyl 7-(2-quinolyl)-6-heptanoate (0.7 g), ethanol (7 ml), and 10% palladium-on-carbon (0.1 g), a catalytic hydrogenation reaction was carried out at atmospheric temperature and pressure for 48 hours. The catalyst was then filtered off and the filtrate was concentrated to dryness to provide the title compound (0.56 g).

oil $^1$H-NMR (CDCl$_3$) δ: 1.24 (3H, t, J=7 Hz), 1.30–1.52 (4H, m), 1.64 (2H, br, q, J=7 Hz), 1.82 (2H, br, q, J=7 Hz), 2.29 (2H, t, J=7 Hz), 2.97 (2H, t, J=8 Hz), 4.11 (2H, q, J=7 Hz), 7.29 (1H, d, J=8 Hz), 7.48 (1H, m), 7.68 (1H, m), 7.78 (1H, br, d, J=8 Hz), 8.03 (1H, br, d, J=8 Hz), 8.07 (1H, d, J=8 Hz).

Reference Example 13

(E)-6-(2-Quinolyl)-5-hexenoate

Potassium tert-butoxide (2.14 g) was added gradually to a solution of 2-quinolinecarbaldehyde (2.0 g) and 1-(4-ethoxycarbonyl)butyltriphenylphosphonium bromide (9.0 g) in DMSO (18 ml), and the mixture was stirred at room temperature for 30 minutes. This reaction mixture was poured into iced water and extracted with ether. The ether layer was washed with saturated aqueous sodium chloride solution twice and dried over anhydrous sodium sulfate. The solvent was then distilled off and the crude residue was purified by silica gel column chromatography (hexane-ethyl acetate=10:1) to provide 0.65 g of ethyl (E)-6-(2-quinolyl)-5-hexenoate and 1.45 g of a mixture of (E) and (Z) compounds, both as oil.

$^1$H-NMR (CDCl$_3$) δ: 1.25 (3H, t, J=7.1 Hz), 1.88–1.98 (2H,m), 2.33–2.44 (4H, m), 4.13 (2H, q, J=7.1 Hz), 6.71 (1H, d, J=15.8 Hz), 6.81 (1H, dt, J=15.8 Hz, 5.8 Hz), 7.43 (2H, m), 7.63–7.78 (2H, m), 8.01–8.09 (2H, m).

To a solution of ethyl (E)-6-(2-quinolyl)-5-hexenoate (2.0 g) in methanol (10 ml) was added 3N aqueous sodium hydroxide solution (5 ml) under ice-cooling and the mixture was then stirred at room temperature for 6 hours. This reaction mixture was neutralized with 3N HCl and the solvent methanol was distilled off under reduced pressure. The resulting crude crystals were collected by filtration, rinsed with water, further rinsed with ether, and dried in vacuo to provide 0.76 g of (E)-6-(2-quinolyl)-5-hexenoic acid as colorless crystals.

m.p. 142°–144° C.;$^1$H-NMR (DMSO-d$_6$) δ: 1.80–1.94 (2H, m), 2.33–2.45 (4H, m), 6.70 (1H, d, J=15.9 Hz), 6.85 (1H, dt, J=15.9 Hz, 6.9 Hz), 7.45–7.72 (3H, m), 7.80 (1H, d, J=7.8 Hz), 7.98 (1H, d, J=8.4 Hz), 8.12 (1H, d, J=8.4 Hz).

Reference Example 14

6-(2-Quinolyl)hexanoic acid

To a solution of 2-quinolinecarbaldehyde (5.0 g) and 1-(4-carboxy)butyltriphenylphosphonium bromide (14.8 g) in DMSO (50 ml) was added 8.34 g of potassium tert-butoxide gradually and the mixture was stirred at room temperature for 30 minutes. This reaction mixture was poured in iced water and washed with toluene. The aqueous layer was neutralized with 3N HCl and extracted with ethyl acetate. The extract was washed with saturated aqueous sodium chloride solution and dried over anhydrous sodium sulfate and the solvent was distilled off. The crude residue and 5% Pd/C were suspended in 100 ml of methanol and stirred under hydrogen gas at room temperature for 2 hours. The catalyst was then filtered off and the filtrate was concentrated to give a crude product. This crude residue was crystallized from methanol-ether to provide 5.18 g of 6-(2-quinolinyl)hexanoic acid as colorless crystals melting at 105°–108° C.

$^1$H-NMR (CDCl$_3$) δ: 1.46–1.58 (2H, m), 1.68–1.95 (4H, m), 2.40 (2H, t, J=7.3 Hz), 3.03 (2H, t, J=7.9 Hz), 6.68 (1H, br s), 7.26–7.35 (1H, m), 7.46–7.54 (1H, m), 7.65–7.74 (1H, m), 7.78 (1H, d, J=7.7 Hz), 8.09–8.17 (2H, m).

The following compounds were synthesized in the like manner.

Reference Example 15

6-(4-Quinolyl)hexanoic acid m.p. 99°–102° C.; $^1$H-NMR (CDCl$_3$) δ: 1.46–1.60 (2H, m), 1.68–1.90 (4H, m), 2.40 (2H, t, J=7.1 Hz), 3.11 (2H, t, J=7.1 Hz), 5.58 (1H, br s), 7.28 (1H, d, J=4.6 Hz), 7.48–7.61 (1H, m), 7.66–7.75 (1H, m), 8.05 (1H, d, J=8.5 Hz), 8.15 (1H, d, J=7.6 Hz), 8.80 (1H, d, J=4.6 Hz).

Reference Example 16

7-(4-Quinolyl)heptanoic acid m.p. 155°–158° C.; $^1$H-NMR (DMSO-d$_6$) δ: 1.38–1.53 (4H, m), 1.54–1.66 (2H, m), 1.66–1.88 (2H, m), 2.27 (2H, t, J=7.2 Hz), 3.04 (1H, br s), 3.09 (2H, t, J=7.7 Hz), 7.27 (1H, d, J=4.5 Hz), 7.48–7.78 (3H, m), 8.07 (2H, d, J=9.7 Hz), 8.79 (1H, d, J=4.5 Hz).

Reference Example 17

Ethyl 6-cyano-6-(1-naphthyl)hexanoate

In 125 ml of DMF was dissolved 12.54 g (75 mmol) of 1-naphthaleneacetonitrile. Then, 3.30 g (82.5 mmol) of 60% sodium hydride was added at room temperature and the mixture was heated to 60° C. and stirred for 30 minutes. After cooling to room temperature, 13.17 ml (82.5 mmol) of ethyl 5-bromovalerate was added. The reaction was further conducted at 60° C. for 30 minutes, after which the reaction mixture was cooled to <10° C. and diluted with 500 ml of pure water. The diluted mixture was extracted with 200 ml of ethyl acetate twice and the organic layer was washed with saturated aqueous sodium chloride solution and dried over anhydrous sodium sulfate. The solvent was then distilled off and the residue was purified by silica gel column chromatography (hexane-CH$_2$Cl$_2$-ethyl acetate=4:2:1) to provide 17.16 g (yield 77.5%) of the title compound as light-yellow oil.

$^1$H-NMR (CDCl$_3$) δ: 1.24 (3H, t, J=7.1 Hz), 1.59–1.78 (4H,m), 2.02–2.14 (2H, m), 2.30–2.37 (2H, m), 4.11 (2H, q, J=7.1 Hz), 4.55 (1H, t, J=7.1 Hz), 7.45–7.63 (3H, m), 7.68 (1H, dd, J=7.2 Hz, 1.2 Hz), 7.83–7.95 (3H, m).

Reference Example 18

6-Cyano-6-(l-naphthyl)hexanoic acid

In 50 ml of methanol was dissolved 7.38 g (25 mmol) of ethyl 6-cyano-6-(1-naphthyl)hexanoate followed by addition of 50 ml of iN aqueous sodium hydroxide solution, and the mixture was stirred at room temperature for 30 minutes. This reaction mixture was diluted with 150 ml of pure water and washed with 150 ml of ethyl acetate. The aqueous layer was acidified with 100 ml of 1 N HCl and extracted with 200 ml of ethyl acetate. The organic layer was washed with saturated aqueous sodium chloride solution, dried over anhydrous sodium sulfate, and purified by silica gel column chromatography (hexane-ethyl acetate=1:4) to provide 6.66 g (yield 99.7%) of the title compound as colorless oil.

$^1$H-NMR (CDCl$_3$) δ: 1.55–1.76 (4H, m), 2.01–2.12 (2H, m), 2.35–2.41 (2H, m), 4.55 (1H, t, J=7.1 Hz), 7.45–7.63 (3H, m), 7.66 (1H, dd, J=7.2, 1.1 Hz), 7.83–7.94 (3H, m).

Reference Example 19

6-(3-Quinolyl)hexanoic acid

The title compound was synthesized in the same manner as Reference Example 14.

m.p. 129°–131° C.; $^1$H-NMR (DMSO-d$_6$) δ: 1.28–1.44 (2H, m), 1.48–1.79 (4H, m), 2.22 (2H, t, J=7.1 Hz), 2.79 (2H, t, J=7.6 Hz), 7.58 (1H, ddd, J=1.3 Hz, 6.8 Hz, 8.1 Hz), 7.70 (1H, ddd, J=1.6 Hz, 6.8 Hz, 8.4 Hz), 7.92 (1H, dd, J=1.6 Hz, 8.1 Hz), 7.98 (1H, dd, J=1.3 Hz, 8.4 Hz), 8.14 (1H, d, J=2.1 Hz), 8.80 (1H, d, J=2.1 Hz), 12.00 (1H, br s).

Reference Example 20

7-(3-Quinolyl)heptanoic acid

The title compound was synthesized in the same manner as Reference Example 14.

m.p. 120°–121° C.; $^1$H-NMR (DMSO-d$_6$) δ: 1.28–1.41 (4H, m), 1.43–1.59 (2H, m), 1.61–1.75 (2H, m), 2.20 (2H, t, J=7.1 Hz), 2.79 (2H, t, J=7.6 Hz), 7.57 (1H, ddd, J=1.3 Hz, 6.8 Hz, 8.2 Hz), 7.70 (1H, ddd, J=1.5 Hz, 6.8 Hz, 8.3 Hz), 7.92 (1H, ddd, J=1.5 Hz, 8.2 Hz), 7.99 (1H, dd, J=1.3 Hz, 8.3 Hz), 8.13 (1H, d, J=2.2 Hz), 8.79 (1H, d, J=2.2 Hz), 12.00 (1H, br s).

Reference Example 21

7-(6-Methoxy-2-quinolyl)heptanoic acid

The title compound was synthesized in the same manner as Reference Example 14.

m.p. 84°–87° C.; $^1$H-NMR (CDCl$_3$) δ: 1.38–1.48 (4H, m), 1.59–1.87 (4H, m), 2.37 (2H, t, J=7.3 Hz), 2.91–3.00 (2H, m), 3.92 (3H, s), 7.05 (1H, d, J=2.8 Hz), 7.27 (1H, d, J=8.6 Hz), 7.35 (1H, dd, J=2.8 Hz, 9.2 Hz), 7.46 (1H, br s), 8.00 (1H, d, J=8.6 Hz), 8.04 (1H, d, J=9.2 Hz).

Reference Example 22

7-Phenyl-7-(2-quinolyl)heptanoic acid

To a solution of 2-benzoylquinoline (4.0 g) and (5-carboxy-l-pentyl)triphenylphosphonium bromide (11.8 g) in DMSO (50 ml) was added potassium t-butoxide (5.8 g) gradually and the mixture was stirred at room temperature for 30 minutes. This reaction mixture was poured in iced water and washed with toluene. The aqueous layer was neutralized with 3N HCl and extracted with ethyl acetate. The extract was washed with saturated aqueous sodium chloride solution and dried and the solvent was distilled off. The crude residue was purified by silica gel column chromatography (hexane-ethyl acetate=2:1) to give 0.90 g of 7-phenyl-7-(2-quinolyl)-6-heptenoic acid as a mixture of its (E) and (Z) forms. This mixture (0.90 g) and 5% palladium-on-carbon (0.90 g) were suspended in methanol (10 ml) and stirred in a hydrogen atmosphere at room temperature for 3 hours. The catalyst was then filtered off and the filtrate was concentrated to provide the title compound (1.0 g).

$^1$H-NMR (CDCl$_3$) δ: 1.26–1.50 (4H, m), 1.54–1.71 (2H, m), 2.14–2.37 (4H, in), 4.30 (1H, t, J=7.9 Hz), 4.96 (1H, br s), 7.17–7.41 (6H, m), 7.48 (1H, dd, J=7.0 Hz, 8.4 Hz), 7.64–7.77 (2H, m), 8.00 (1H, d, J=8.8 Hz), 8.13 (1H, d, J=8.1 Hz).

Reference Example 23

6-Phenyl-6-(2-quinolyl)hexanoic acid

The title compound was synthesized in the same manner as Reference Example 22.

Oil $^1$H-NMR (CDCl$_3$) δ: 1.31–1.46 (2H, m), 1.65–1.81 (2H, m), 2.15–2.48 (4H, m), 4.11 (1H, br s), 4.35 (1H, t, J=7.7 Hz), 7.15–7.52 (7H, m), 7.65–7.77 (2H, m), 8.02 (1H, d, J=8.5 Hz), 8.15 (1H, d, J=8.2 Hz).

Reference Example 24

Ethyl 6-amino-6-(2-naphthyl)hexanoate

1) An ethanolic solution (150 ml) of ethyl 6-oxo-6-(2-naphthyl)hexanoate (15 g) was added to an aqueous solution (42 ml) of hydroxylamine hydrochloride (4.8 g) and sodium acetate (5.7 g) and the mixture was refluxed for 2 hours. The ethanol was then distilled off under reduced pressure and the residue was extracted with ethyl acetate. The extract was washed with saturated aqueous sodium chloride solution and dried and the solvent was distilled off. The crude residue was purified by silica gel column chromatography (hexane-ethyl acetate =10:1) to provide ethyl 6-hydroxyimino-6-(2-naphthyl)hexanoate (19 g).

$^1$H-NMR (CDCl$_3$) δ: 1.22 (3H, t, J=7.1 Hz), 1.57–1.88 (4H,m), 2.36 (2H, t, J=7.2 Hz), 2.96 (2H, t, J=7.5 Hz), 4.11 (2H, q, J=7.1 Hz), 7.46–7.55 (2H, m), 7.81–7.92 (4H, m), 7.91 (1H, br s), 8.01 (1H, s).

2) Ethyl 6-amino-6-(2-naphthyl)hexanoate Ethyl 6-hydroxyimino-6-(2-naphthyl)hexanoate (19.2 g) and platinum oxide (0.96 g) were suspended in acetic acid (160 ml) and the suspension was stirred in a hydrogen atmosphere at room temperature for 10 hours. The catalyst was then filtered off and the filtrate was concentrated. The residue was dispersed in saturated aqueous sodium hydrogen carbonate solution and extracted with ethyl acetate. This extract was dried over anhydrous sodium sulfate and concentrated. The crude residue thus obtained was purified by silica gel column chromatography (ethyl acetate-methanol=10:1) to provide ethyl 6-amino-6-(2-naphthyl)hexanoate (12.1 g).

$^1$H-NMR (CDCl$_3$) δ: 1.21 (3H, t, J=7.1 Hz), 1.26–1.49 (2H,m), 1.55–1.71 (2H, m), 1.73 (2H, br s), 1.74–1.85 (2H, m), 2.26 (2H, t, J=7.4 Hz), 2.69–2.81 (1H, m), 4.08 (2H, q, J=7.1 Hz), 7.41–7.52 (3H, m), 7.73 (1H, s), 7.77–7.87 (3H, m).

Reference Example 25

Ethyl 6-benzoylamino-6-(2-naphthyl)hexanoate

While a solution (5 ml) of ethyl 6-amino-6-(2-naphthyl) hexanoate in acetonitrile (1.0 g) and a 1N aqueous solution of sodium hydroxide (4 ml) were vigorously stirred together under ice-cooling, benzoyl chloride (0.54 g) was added dropwise and the mixture was further stirred at room temperature for 1 hour. The organic layer was separated and the aqueous layer was extracted with ethyl acetate. The extract and the organic layer were combined, dried, and concentrated to provide ethyl 6-benzoylamino-6-(2-naphthyl) hexanoate (1.5 g).

$^1$H-NMR (CDCl$_3$) δ: 1.20 (3H, t, J=i.1 Hz), 1.32–1.56 (2H,m), 1.61–1.82 (2H, m), 1.95–2.11 (2H, m), 2.28 (2H, t, J=7.5 Hz), 4.08 (2H, q, J=7.1 Hz), 5.26–5.41 (1H, m), 6.52 (1H, d, J=7.8 Hz), 7.38–7.52 (6H, m), 7.74–7.88 (6H, m).

Reference Example 26

Ethyl 6-acetylamino-6-(2-naphthyl)hexanoate

The title compound was synthesized in the same manner as Reference Example 25.

$^1$H-NMR (CDCl$_3$) δ: 1.21 (3H, t, t=7.1 Hz), 1.28–1.44 (2H,m), 1.58–1.75 (2H, m), 1.83–1.95 (2H, m), 2.01 (3H, s), 2.27 (2H, t, J=7.4 Hz), 4.09 (2H, q, J=7.1 Hz), 5.07–5.19 (1H, m), 5.81 (1H, d, J=8.1 Hz), 7.40 (1H, dd, J=1.9, 8.5 Hz), 7.45–7.53 (2H, m), 7.73 (1H, s), 7.78–7.85 (3H, m).

Reference Example 27

Ethyl 6-(4-methylbenzenesulfonylamino)-6-(2-naphthyl)hexanoate

To a solution (10 ml) of ethyl 6-amino-6-(2-naphthyl)hexanoate (1.0 g) and 4-methylbenzenesulfonyl chloride (0.73 g) in THF was added triethylamine (0.39 g) dropwise and the mixture was stirred at room temperature for 2 hours. The reaction mixture was then diluted with water and extracted with ethyl acetate. The extract was dried and concentrated and the crude residue was recrystallized from ethyl acetate-hexane to provide the title compound (1.3 g).

m.p. 87°–91° C.; $^1$H-NMR (CDCl$_3$) δ: 1.20 (3H, t, J=7.1 Hz), 1.23–1.43 (2H,m), 1.49–1.66 (2H, m), 1.67–1.93 (2H, m), 2.16 (3H, s), 2.19 (2H, t, J=7.1 Hz), 4.08 (2H, q, J=7.1 Hz), 4.37–4.48 (1H, m), 4.96 (1H, d, J=7.4 Hz), 6.91 (2H, d, J=8.5 Hz), 7.12 (1H, dd, J=1.7, 8.5 Hz), 7.33 (1H, s), 7.40–7.51 (4H, m), 7.63 (2H, d, J=8.5 Hz), 7.70–7.79 (1H, m).

Reference Example 28

Ethyl 6-methanesulfonylamino-6-(2-naphthyl)hexanoate

The title compound was synthesized in the same manner as Reference Example 27.

$^1$H-NMR (CDCl$_3$) δ: 1.21 and 1.28 (3H, t, J=7.1 Hz and t, J=7.1 Hz), 1.32–1.55 (2H, m), 1.62–1.98 (4H, m), 2.26 (2H, t, J=7.4 Hz), 2.52 (3H, s), 4.09 and 4.13 (2H, t, J=7.1 Hz and t, J=7.1 Hz), 4.54–4.71 (1H, m), 4.90 (1H, d, J=7.3 Hz), 7.41 (1H, dd, J=1.8, 8.5 Hz), 7.46–7.58 (2H, m), 7.75 (1H, s), 7.83–7.91 (3H, m).

Reference Example 29

Ethyl 6-benzenesulfonylamino-6-(2-naphthyl)hexanoate

The title compound was synthesized in the same manner as Reference Example 27.

m.p. 81°–84° C.; $^1$H-NMR (CDCl$_3$) δ: 1.20 (3H, t, J=7.1 Hz), 1.22–1.44 (2H,m), 1.50–1.65 (2H, m), 1.68–1.97 (2H, m), 2.19 (2H, t, J=7.3 Hz), 4.07 (2H, q, J=7.1 Hz), 4.41–4.51 (1H, m), 5.10 (1H, d, J=7.7 Hz), 7.07–7.23 (3H, m), 7.23–7.34 (1H, m), 7.38–7.49 (3H, m), 7.57–7.78 (5H, m).

Reference Example 30

Ethyl 6-(4-fluorobenzenesulfonylamino)-6-(2-naphthyl)hexanoate

The title compound was synthesized in the same manner as Reference Example 27.

m.p. 91°–93° C.; $^1$H-NMR (CDCl$_3$) δ: 1.20 (3H, t, J=7.1 Hz), 1.23–1.44 (2H,m), 1.52–1.66 (2H, m), 1.68–1.94 (2H, m), 2.21 (2H, t, J=7.3 Hz), 4.08 (2H, q, J=7.1 Hz), 4.41–4.53 (1H, m), 5.02 (1H, d, J=7.3 Hz), 6.71–6.83 (2H, m), 7.08 (1H, dd, J=1.6, 8.4 Hz), 7.40 (1H, s), 7.43–7.79 (7H, m).

Reference Example 31

Methyl 7-(1-isoquinolyl)heptanoate

Under argon gas at −78° C., 2.0M lithium diisopropylamide/THF (12 ml) was added dropwise to a solution (40 ml) of dimethyl 2-isopropoxycarbonyl-1,2-dihydroisoquinoline-l-phosphonate (7.4 g) in THF and the mixture was stirred under the same conditions for 5 minutes. To this reaction mixture was added a solution (5 ml) of methyl 7-oxo heptanoate (3.9 g) in THF dropwise and the temperature was allowed to return to room temperature. The reaction mixture was further stirred at room temperature for 2 hours. Then, 1N HCl was added and the mixture was extracted with ethyl acetate. The extract was washed with saturated aqueous sodium hydrogen carbonate solution, dried, and concentrated. The residue was purified by silica gel column chromatography (hexane-ethyl acetate=10:1). The oil thus obtained was dissolved in 4N methanolic hydrochloric acid and the solution was stirred at 50° C. for 1 hour. The methanol was then distilled off under reduced pressure and the residue was diluted with water and washed with ether. The aqueous layer was made basic using aqueous sodium hydroxide solution and extracted with ethyl acetate, and the extract was dried and concentrated. The resulting crude residue was purified by silica gel column chromatography (hexane-ethyl acetate=3:1) to provide methyl 7-(1-isoquinolyl)heptanoate (1.7 g).

$^1$H-NMR (CDCl$_3$) δ: 1.35–1.55 (4H, m), 1.56–1.74 (2H, m), 1.78–1.96 (2H, m), 2.31 (2H, t, J=7.1 Hz), 3.25–3.33 (2H, m), 3.66 (3H, s), 7.50 (1H, d, J=5.9 Hz), 7.54–7.71 (2H, m), 7.84 (1H, d, J=7.7 Hz), 8.15 (1H, d, J=8.4 Hz), 8.43 (1H, d, J=5.9 Hz).

Reference Example 32

Methyl 6-(1-isoquinolyl)hexanoate

The title compound was synthesized in the same manner as Reference Example 31.

$^1$H-NMR (CDCl$_3$) δ: 1.42–1.61 (2H, m), 1.64–1.81 (2H, m), 1.81–2.00 (2H, m), 2.34 (2H, t, J=7.4 Hz), 3.30 (2H, dd, J=7.8, 8.0 Hz), 3.66 (2H, s), 7.51 (1H, d, J=5.7 Hz), 7.55–7.71 (2H, m), 7.82 (1H, dd, J=1.3, 7.5 Hz), 8.15 (1H, dd, J=1.2, 8.3 Hz), 8.43 (1H, d, J=5.7 Hz).

Reference Example 33

6-(Benzoxazol-2-yl)hexanoic acid

1) Ethyl 6-(benzoxazol-2-yl)hexanoate

A mixture of monoethyl heptanedioate (9.41 g), o-aminophenol (5.46 g), boric acid (3.09 g), and xylene (100 ml) was refluxed with water being azeotropically removed for 16 hours. After cooling to room temperature, the insoluble matter was filtered off and the filtrate was concentrated under reduced pressure. The residue was purified by silica gel column chromatography (hexane-ethyl acetate= 2:1) to provide ethyl 6-(benzoxazol-2-yl)hexanoate (10.1 g).

$^1$H-NMR (CDCl$_3$) δ: 1.24 (3H, t, J=7.1 Hz), 1.35–1.53 (2H,m), 1.16–1.77 (2H, m), 1.85–1.18 (2H, m), 2.27–2.40 (2H, m), 2.95 (2H, t, J=7.5 Hz), 4.12 (2H, q, J=7.1 Hz), 7.27–7.32 (2H, m), 7.43–7.51 (1H, m), 7.63–7.72 (1H, m).

2) Then, the procedure of Reference Example 18 was followed to provide 6-(benzoxazol-2-yl)hexanoic acid.

m.p. 82°–82° C.; $^1$H-NMR (CDCl$_3$) δ: 1.47–1.57 (2H, m), 1.62–1.80 (2H, m), 1.85–2.01 (2H, m), 2.39 (2H, t, J=7.3

Hz), 2.96 (2H, t, J=7.7 Hz), 7.28–7.35 (2H, m), 7.44–7.56 (1H, m), 7.64–7.73 (1H, m).

Reference Example 34

6-(Thiazolo[5,4-b]pyridin-2-yl)hexanoic acid

1) Ethyl 6-(thiazolo[5,4-b]pyridin-2-yl)hexanoate

Monoethyl heptanedioate (10.35 g) was dissolved in THF (55 ml) followed by addition of DMF (1 drop) and oxalyl chloride (11.73 ml), and the mixture was stirred at room temperature for 15 minutes. The excess oxalyl chloride was distilled off under reduced pressure and the residue was added to a solution (100 ml) of 3-amino-2-chloropyridine (6.43 g) in THF-saturated aqueous sodium hydrogen carbonate solution (1:1). The mixture was stirred at room temperature for 1 hour and, then, extracted with ethyl acetate (50 ml). The organic layer was washed serially with 1N-HCl and 1N-NaOH and dried over anhydrous sodium sulfate. The solvent was then distilled off and the residue was purified by silica gel chromatography (hexane-ethyl acetate=2:1). After this product was dissolved in pyridine (50 ml), Lawesson's reagent (15.04 g) was added and the reaction was conducted at 100° C. for 4 hours. Then, saturated aqueous sodium hydrogen carbonate solution (10 ml) was added slowly at 50° C. and, then, saturated aqueous sodium hydrogen carbonate solution (100 ml) was further added at room temperature. The mixture was extracted with ethyl acetate (200 ml) and the extract was dried and concentrated. The residue was purified by silica gel column chromatography (hexane-ethyl acetate=2:1) to provide ethyl 6-(thiazolo[5,4-b]pyridin-2-yl)hexanoate (4.4 g).

$^1$H-NMR (CDCl$_3$) δ: 1.25 (3H, t, J=7.2 Hz), 1.44–1.58 (2H,m), 1.65–1.80 (2H, m), 1.87–2.02 (2H, m), 2.33 (2H, t, J=7.4 Hz), 3.14 (2H, t, J=7.7 Hz), 4.12 (2H, q, J=7.2 Hz), 7.41 (1H, dd, J=8.2, 4.7 Hz), 8.19 (1H, dd, J=8.2, 1.6 Hz), 8.54 (1H, dd, J=4.7, 1.6 Hz).

2) Then, the title compound was synthesized in the same manner as Reference Example 18.

$^1$H-NMR (CDCl$_3$) δ: 1.46–1.61 (2H, m), 1.65–1.82 (2H, m), 1.88–2.02 (2H, m), 2.40 (2H, t, J=7.3 Hz), 3.15 (2H, t, J=7.6 Hz), 7.41 (1H, dd, J=8.3, 4.7 Hz), 8.21 (1H, dd, J=8.3, 1.6 Hz), 8.55 (1H, dd, J=4.7, 1.6 Hz).

Reference Example 35

6-(l-Phenylbenzimidazol-2-yl)hexanoic acid

1) Ethyl 6-(1-phenylbenzimidazol-2-yl)hexanoate

Monoethyl heptanedioate (10.35 g) was dissolved in THF (55 ml) followed by addition of DMF (1 drop) and oxalyl chloride (11.73 ml), and the mixture was stirred at room temperature for 15 minutes. The excess oxalyl chloride was distilled off under reduced pressure and the residue was added to a solution (100 ml) of N-phenyl-1,2-phenylenediamine (9.21 g) in THF-saturated aqueous sodium hydrogen carbonate solution (1:1). The mixture was stirred at room temperature for 1 hour and, then, extracted with ethyl acetate (50 ml). The organic layer was washed with 1N HCl and 1N NaOH serially and dried. The solvent was then distilled off and the residue was purified by silica gel column chromatography (hexane-ethyl acetate=2:1) to give crystals (14.72 g). After this crystal crop (13.54 g) was dissolved in ethanol (50 ml), sulfuric acid (1 ml) was added and the reaction was conducted under reflux for 3 hours. The solvent was then distilled off under reduced pressure and the residue was diluted with 1N-sodium hydroxide (100 ml) and extracted with ethyl acetate (100 ml). The extract was dried and concentrated and the residue was purified by silica gel column chromatography (hexane-ethyl acetate=1:1) to provide ethyl 6-(1-phenylbenzimidazol-2-yl)hexanoate (6.49 g).

$^1$H-NMR (CDCl$_3$) δ: 1.22 (3H, t, J=7.1 Hz), 1.31–1.42 (2H,m), 1.52–1.68 (2H, m), 1.73–1.90 (2H, m), 2.25 (2H, t, J=7.4 Hz), 2.79 (2H, t, J=7.7 Hz), 4.09 (2H, q, J=7.1 Hz), 7.07–7.39 (5H, m), 7.48–7.64 (3H, m), 7.75–7.81 (1H, m).

2) The above product was hydrolyzed in the same manner as Reference Example 18 to provide 6-(1-phenylbenzimidazol-2-yl)hexanoic acid.

m.p. 132°–133° C.; $^1$H-NMR (CDCl$_3$) δ: 1.35–1.48 (2H, m), 1.63–1.85 (4H, m), 2.36 (2H, t, J=7.4 Hz), 2.85 (2H, t, J=7.6 Hz), 7.09 (1H, d, J=7.6 Hz), 7.17–7.40 (4H, m), 7.55–7.66 (3H, m), 7.84 (1H, d, J=7.8 Hz).

Reference Example 36

7-(Benzothiazol-2-yl)-7-cyanoheptanoic acid

1) Ethyl 7-(benzothiazol-2-yl)-7-cyanoheptanoate

To a solution of malonitrile (6.61 g) and acetic acid (60 ml) in ethanol (100 ml) was added o-amino thio-phenol (7 ml) and the reaction was conducted at room temperature for 16 hours. This reaction mixture was diluted with ethyl acetate (200 ml) and washed with 5% aqueous sodium chloride solution. The organic layer was further washed with 3N NaOH (200 ml) and saturated NaCl solution (200 ml) and dried and the solvent was distilled off under reduced pressure. The residue was crystallized from IPE to give 2-benzothiazoleacetonitrile (13.8 g). This crystalline product (10.45 g) was dissolved in DMF (100 ml), and after addition of 60% sodium hydride (1.44 g) under ice-cooling, the solution was heated to 60° C. and stirred for 30 minutes. After cooling to room temperature, ethyl 6-bromohexanoate (5.31 ml) was added and the reaction was conducted at 60° C. for 30 minutes. After cooling to 10° C. or less, the reaction mixture was diluted with pure water (300 ml) and extracted with ethyl acetate (200 ml) twice. The pooled organic layer was washed with saturated aqueous sodium chloride solution and dried. The solvent was then distilled off under reduced pressure and the residue was purified by silica gel column chromatography (hexane-ethyl acetate= 4:1) to provide ethyl 7-(benzothiazol-2-yl)-7-cyanoheptanoate (3.0 g).

$^1$H-NMR (CDCl$_3$) δ: 1.25 (3H, t, J=7.2 Hz), 1.32–1.73 (6H,m), 2.10–2.35 (4H, m), 4.12 (2H, q, J=7.2 Hz), 4.35 (1H, t, J=7.3 Hz), 7.40–7.57 (2H, m), 7.88–7.94 (1H, m), 8.02–8.04 (1H, m).

2) The above product was then hydrolyzed in the same manner as Reference Example 18 to provide 7-(benzothiazol-2-yl)-7-cyanoheptanoic acid.

$^1$H-NMR (CDCl$_3$) δ: 1.34–1.76 (6H, m), 2.13–2.30 (2H, m), 2.37 (2H, t, J=7.0 Hz), 4.38 (1H, t, J=7.3 Hz), 7.40–7.57 (2H, m), 7.87–7.93 (1H, m), 8.03–8.08 (1H, m).

Reference Example 37

6-(Benzothiazol-2-yl)hexanoic acid

A mixture of monoethyl heptanedioate (9.41 g), o-aminothiophenol (5.35 ml) and polyphosphoric acid (150 g) was heated to 130° C. with stirring and the reaction was conducted at the same temperature for 2 hours. After cooling to 40° C., pure water (300 ml) was added and the mixture was stirred at 50° C. for 30 minutes. After cooling to room temperature, the reaction mixture was extracted with ethyl acetate (500 ml). The organic layer was extracted with 1N NaOH, acidified with concentrated HCl, and reextracted with ethyl acetate. The extract was dried and concentrated under reduced pressure and the residue was purified by silica gel column chromatography (ethyl acetate) to provide the title compound (4.6 g).

m.p. 71°–72° C.; $^1$H-NMR (CDCl$_3$) δ: 1.42–1.61 (2H, m), 1.64–1.81 (2H, m), 1.85–2.00 (2H, m), 2.39 (2H, t, J=7.3 Hz), 3.15 (2H, t, J=7.7 Hz), 7.31–7.50 (2H, m), 7.82–7.87 (1H, m), 7.97–8.01 (1H, m).

Reference Example 38

7-(Benzothiazol-2-yl)heptanoic acid

The title compound was synthesized in the same manner as Reference Example 37.

m.p. 62°–63° C.; $^1$H-NMR (CDCl$_3$) δ: 1.35–1.52 (4H, m), 1.60–1.75 (2H, m), 1.83–1.97 (2H, m), 2.36 (2H, t, J=7.4 Hz), 3.13 (2H, t, J=7.6 Hz), 7.35 (1H, td, J=7.6, 1.3 Hz), 7.46 (1H, td, J=7.6, 1.3 Hz), 7.84 (1H, dd, J=7.6, 1.3 Hz), 7.99 (1H, dd, J=7.6, 1.3 Hz).

Reference Example 39

7-Cyano-7-(2-naphthyl)heptanoic acid

1) Ethyl 7-cyano-7-(2-naphthyl)heptanoate was synthesized in the same manner as Reference Example 17.

$^1$H-NMR (CDCl$_3$) δ: 1.23 (3H, t, J=7.1 Hz), 1.32–1.70 (6H,m), 1.92–2.07 (2H, m), 2.28 (2H, t, J=7.3 Hz), 3.95 (1H, t, J=7.3 Hz), 4.11 (2H, q, J=7.1 Hz), 7.40 (1H, dd, J=8.5, 1.9 Hz), 7.47–7.56 (2H, m), 7.81–7.89 (4H, m).

2) The above product was hydrolyzed in the same manner as Reference Example 18 to provide 7-cyano-7-(2-naphthyl) heptanoic acid.

m.p. 88°–89° C.; $^1$H-NMR (CDCl$_3$) δ: 1.47–1.70 (6H, m), 1.93–2.04 (2H, m), 2.35 (2H, t, J=7.2 Hz), 3.95 (1H, t, J=7.1 Hz), 7.39 (1H, dd, J=8.8, 1.8 Hz), 7.49–7.54 (2H, m), 7.80–7.89 (4H, m).

Reference Example 40

7-Ethoxycarbonyl-7-(1-naphthyl)heptanoic acid

1) Ethyl 7-ethoxycarbonyl-7-(1-naphthyl)heptanoate was synthesized in the same manner as Reference Example 17.

$^1$H-NMR (CDCl$_3$) δ: 1.16 (3H, t, J=7.5 Hz), 1.23 (3H, t, J=7.3 Hz), 1.30–1.47 (4H, m), 1.52–1.66 (2H, m), 1.81–1.98 (1H, m), 2.18–2.35 (3H, m), 4.03–4.20 (4H, m), 4.35 (1H, dd, J=8.4, 6.2 Hz), 7.41–7.58 (4H, m), 7.76 (1H, br d, J=7.6 Hz), 7.84–7.90 (1H, m), 8.13 (1H, br d, J=7.8 Hz).

2) Then, 7-ethoxycarbonyl-7-(1-naphthyl)heptanoic acid was provided in the same manner as Reference Example 18.

$^1$H-NMR (CDCl$_3$) δ: 1.16 (3H, t, J=7.2 Hz), 1.24–1.46 (4H,m), 1.48–1.70 (2H, m), 1.77–2.00 (1H, m), 2.16–2.40 (1H, m), 2.31 (2H, t, J=7.1 Hz), 4.03–4.20 (2H, m), 4.39 (1H, dd, J=8.5, 6.7 Hz), 7.40–7.58 (4H, m), 7.77 (1H, br d, J=7.8 Hz), 7.83–7.89 (1H, m), 8.12 (1H, br d, J=7.8 Hz).

Reference Example 41

1,4-Naphthohydroquinone

To 1,4-naphthoquinone (25 g) suspended in ethanol (100 ml) was added a solution (150 ml) of stannous chloride (368 g) in concentrated hydrochloric acid gradually at room temperature. After the evolution of heat had ceased and a homogeneous state was established, the reaction mixture was brought back to room temperature and the resulting crystals were collected by filtration, rinsed with water, and dried to provide the title compound (18.2 g).

m.p. 210°–213° C.

Reference Example 42

6-(4-Methoxyphenyl)-6-(1,4-naphthoquinon-2-yl) hexanoic acid 1,4-Naphthohydroquinone (8 g) was reacted with 6-hydroxy-6-(4-methoxyphenyl)hexanoic acid (11.9 g) in the presence of p-toluenesulfonic acid (3.8 g) in toluene (200 ml) at 80° C. for 15 hours. Then, the reaction mixture was extracted with ethyl acetate and concentrated. The residue was submitted to an overnight reaction with an aqueous solution (120 ml) of iron (III) chloride hexahydrate (31 g) (0.1 ml) in acetic acid (70 ml) at room temperature. This reaction mixture was extracted with ethyl acetate and concentrated and the residue was purified by silica gel column chromatography. Recrystallization from hexane-ethyl acetate gave 4 g of the title compound.

m.p. 141°–143° C.

Reference Example 43

2-Methyl-1,4-naphthohydroquinone 1,4-diacetate

2-Methyl-1,4-naphthoquinone (50 g), suspended in acetic anhydride (150 ml), was dissolved by adding pyridine (140 ml). While the solution was cooled at 0° C., zinc dust (21 g) was added and the reaction was conducted at 0° C. for 1 hour and then at room temperature for 1 hour. This reaction mixture was poured in iced water (700 ml) and the resulting crystals were recovered by filtration and extracted into ethyl acetate. The extract was washed with water, dried, and concentrated. The residue was crystallized from hexane to provide the title compound (74 g).

m.p. 95°–97° C.

Reference Example 44

2-Methyl-1,4-naphthohydroquinone 1-monoacetate 2-methyl-1,4-naphthohydroquinone 1,4-diacetate (74 g) was suspended in methanol (300 ml) followed by addition of 25% aqueous ammonia (22 ml) at room temperature. The reaction was carried out at 40° C. for 3 hours and this reaction mixture was concentrated under reduced pressure. The residue was extracted with ethyl acetate, washed with water, dried, and concentrated. The residue was purified by silica gel column chromatography. Crystallization from hexane-ethyl acetate gave 56 g of the title compound.

m.p. 124°–126° C.

Reference Example 45

7-(3-Methyl-1,4-naphthoquinon-2-yl)-7-phenyl-heptanoic acid

2-Methyl-1,4-naphthohydroquinone 1-monoacetate (10.8 g) and 7-hydroxy-7-phenylheptanoic acid (11.1 g) were dissolved in toluene (120 ml) at 50° C. and p-toluenesulfonic acid (3.8 g) (20 mmol) was added. The reaction was conducted at 50° C. for 22 hours and this reaction mixture was extracted with ethyl acetate. The extract was washed with water and concentrated under reduced pressure to 100 ml. To the residue was added an aqueous solution (100 ml) of iron (III) chloride hexahydrate (27 g) (0.1 mmol) and the reaction was conducted for 3 days. This reaction mixture was extracted with ethyl acetate and the extract was concentrated. The residue was purified by silica gel column chromatography and crystallized from hexane-ethyl acetate to provide the title compound (8.1 g).

Reference Example 46

The following compounds were synthesized by the procedure described in Example 1 which appears hereinafter.

Reference Example 46-1

7-(1-Hydroxy-2-naphthyl)-7-phenylheptanohydroxamic acid

Reference Example 46-2

6-(1-Hydroxy-2-naphthyl)hexanohydroxamic acid

Reference Example 46-3

7-(2-Hydroxy-1-naphthyl)heptanohydroxamic acid

Reference Example 46-4

7-(2-Methoxy-1-naphthyl)heptanohydroxamic acid

Reference Example 46-5

7-(2-Naphthyl)heptanohydroxamic acid

Reference Example 47

The following compounds were synthesized by the procedure described in Example 2 which appears hereinafter. The starting carboxylic acids are indicated in parentheses.

Reference Example 47-1

6-(Benzothiazol-2-yl)hexanohydroxamic acid (starting material: Reference Example 37)

Reference Example 47-2

6-(Benzoxazol-2-yl)hexanohydroxamic acid (starting material: Reference Example 33)

Reference Example 47-3

7-(Benzothiazol-2-yl)heptanohydroxamic acid (starting material: Reference Example 38)

Reference Example 47-4

6-(1-Phenylbenzimidazol-2-yl)hexanohydroxamic acid (starting material: Reference Example 35)

Reference Example 47-5

6-(Thiazolo[5,4-b]pyridin-2-yl)hexanohydroxamic acid (starting material: Reference Example 34)

Reference Example 48

7-(1-Nitro-2-naphthyl)heptanohydroxamic acid
1) 7-(l-Nitro-2-naphthyl)heptanoic acid Fuming nitric acid (81 ml) was ice-cooled and acetic anhydride (4.5 ml) was added dropwise. The mixture was cooled to −78° C. and a solution of ethyl 7-(2-naphthyl)heptanoate (10 g) in acetic anhydride (20 ml) was added. The temperature was then increased to −20° C. over a period of 2 hours, after which ethanol (10 ml) was added dropwise. The mixture was stirred for 30 minutes. Then, 2N aqueous sodium hydroxide solution (300 ml) was added under ice-cooling and the mixture was further stirred for 2 hours and, then, extracted with ether. The organic layer was washed with water, dried, and concentrated to dryness. The solid residue (11 g) was added to 5N aqueous sodium hydroxide solution (66 ml)-tetrahydrofuran (264 ml) and the mixture was refluxed for 6 hours. The reaction mixture was acidified with HCl and extracted with ethyl acetate. The organic layer was washed with water, dried, and concentrated to dryness and the residue was recrystallized from hexane-ethyl acetate to provide 7-(1-nitro-2-naphthyl)heptanoic acid (3.4 g).

m.p. 84°–89° C.; $^{11}$H-NMR (CDCl$_3$): 1.25–1.50 (4H, m), 1.50–1.80 (4H, m), 2.36 (2H, t, J=7 Hz), 2.74 (2H, t, J=8 Hz), 7.38 (1H, d, J=9 Hz), 7.50–7.75 (3H, m), 7.83–7.95 (2H, m).

2) 7-(1-Nitro-2-naphthyl)heptanoic acid (1 g), thus obtained, was treated in the same manner as Reference Example 47 to provide the title compound (0.78 g).

Reference Example 49

7-(1-Amino-2-naphthyl)heptanohydroxamic acid
1) Methoxymethyl 7-(l-amino-2-naphthyl)heptanoate 7-(1-Nitro-2-naphthyl)heptanoic acid (2 g) and triethylamine (2.02 g) were dissolved in DMF (10 ml) followed by addition of chloromethyl methyl ether (0.802 g), and the mixture was stirred at room temperature for 20 hours. This reaction mixture was diluted with cold saturated aqueous sodium hydrogen carbonate solution and extracted with ethyl acetate. The organic layer was washed with water, dried, and concentrated to dryness. Using the residue, 10% palladium-on-carbon (0.23 g), and ethanol (23 ml), a catalytic hydrogenation reaction was carried out at atmospheric temperature and pressure for 18 hours. The catalyst was then filtered off and the filtrate was concentrated under reduced pressure to provide methoxymethyl 7-(1-amino-2-naphthyl) heptanoate (2.1 g).

Oil $^1$H-NMR (CDCl$_3$) δ: 1.30–1.50 (4H, m), 1.55–1.80 (4H, m), 2.36(2H, t, J=7 Hz), 2.68 (2H, t, J=7 Hz), 3.45 (3H, s), 4.14 (2H, br), 5.23 (2H, s), 7.21 (1H, d, J=8 Hz), 7.29 (1H, d, J=8 Hz), 7.35–7.50 (2H, m), 7.73–7.86 (2H, m).

2) The methoxymethyl 7-(1-amino-2-naphthyl) heptanoate (0.3 g) was added to 1M hydroxylamine/methanol (2.85 ml) and the mixture was stirred at room temperature for 1.5 hours. This reaction mixture was poured in saturated aqueous ammonium chloride solution and extracted with ethyl acetate. The organic layer was washed with water, dried, and concentrated to dryness, and the residue was recrystallized from hexane-ether to provide the title compound (0.116 g).

Reference Example 50

7-(l-Mesylamino-2-naphthyl)heptanohydroxamic acid
1) 7-(1-Mesylamino-2-naphthyl)heptanoic acid In pyridine (3 ml) was dissolved methoxymethyl 7-(1-amino-2-naphthyl)heptanoate (0.3 g) followed by addition of mesyl chloride (0.218 g), and the mixture was stirred at 50° C. for 2 hours. This reaction mixture was poured in 0.5N HCl and extracted with ethyl acetate. The organic layer was washed with water, dried, and concentrated to dryness. The residue was treated with 1N HCl (3 ml) and tetrahydrofuran (6 ml) at the reflux temperature for 1.5 hours and, after cooling, extracted with ethyl acetate. The organic layer was washed with water, dried, and concentrated to dryness, and the residue was recrystallized from hexane-diisopropyl ether to provide 7-(1-mesylamino-2-naphthyl)heptanoic acid (0.281 g).

m.p. 122°–127° C.; $^1$H-NMR (CDCl$_3$) δ: 1.35–1.50 (4H, m), 1.55–1.80 (4H, m), 2.35 (2H, t, J=7 Hz), 3.00 (2H, t, J=8 Hz), 3.08 (3H, s), 6.82 (iH, s), 7.40–7.70 (3H, m), 7.88–7.90 (2H, m), 8.17 (1H, d, J=8 Hz).

The 7-(1-mesylamino-2-naphthyl)heptanoic acid thus obtained (0.15 g) was further treated as in Example 1, which appears hereinafter, to provide the title compound.

Reference Example 51

7-(1-Tosylamino-2-naphthyl)heptanohydroxamic acid
Using methoxymethyl 7-(1-amino-2-naphthyl)heptanoate and tosyl chloride, the procedure of Reference Example 50 was otherwise repeated to provide 7-(1-tosylamino-2-naphthyl)heptanoic acid.

m.p. 128°–133° C.; $^1$H-NMR (CDCl$_3$) δ: 1.20–1.70 (8H, m), 2.35 (2H, t, J=7 Hz), 2.40 (3H, s), 2.57 (2H, t, J=8 Hz), 6.75 (1H, s), 7.13–7.43 (5H, m), 7.54 (2H, d, J=8 Hz), 7.70–7.80 (3H, m).

The 7-(1-tosylamino-2-naphthyl)heptanoic acid thus obtained was treated as in Example 1, which appears hereinafter, to provide the title compound.

Reference Example 52

6-(4-Methoxyphenyl)-6-(3-methyl-1,4-naphthoquinon-2-yl)hexanohydroxamic acid 1) 1,4-Dimethoxy-2-methylnaphthalene A solution of 125 g of 2-methyl-1,4-naphthoquione in 1250 ml of hot ethanol was treated with a solution of 500 g of stannous chloride in 500 ml of concentrated hydrochloric acid at room temperature. Water (2100 ml) was added to the solution and the precipitate was filtered, washed, and dried. 2-Methyl-1,4-naphthohydroquinone was dissolved in 1000 ml of ethanol at room temperature and 145 ml of 12N NaOH was added at 30° C. followed by additional 165 ml of dimethyl sulfate at 30°–40° C. for 2 hours. The mixture was reflux for 3 hours and concentrated. The residue was extracted with ether to give 113 g of 1,4-dimethoxy-2-methylnaphthalene as an oil.

$^1$H-NMR (CDCl$_3$) δ: 2.24 (3H, s), 3.85 (3H, s), 3.95 (3H, s), 6.59 (1H, s), 7.22–7.56 (2H, m), 8.02 (1H, d, J=8 Hz), 8.19 (1H, d, J=8 Hz).

2) 1,4-Dimethoxy-3-methylnaphthalene-2-carbaldehyde

1–4-Dimethoxy-2-methylnaphthalene (113 g) in 330 ml of methylene chloride was added 123 ml of titanium tetrachloride at 0° C. for 30 min. The solution was cooled, and 48 ml of dichloromethyl methyl ether was added dropwise over 30 min at 0° C. After the addition was complete, the mixture was stirred at 0° C. for 1 hour then at room temperature for 3 hours. The reaction mixture was poured into ice-water and the organic layer was separated, washed, dried, and concentrated. The residue was purified with column chromatography over silica gel using n-hexane/ethyl acetate (7/1) as an eluent to obtain 75 g of an aldehyde.

m.p. 89°–91° C.

3) 6-(1,4-Dimethoxy-3-methylnaphthalen-2-yl)-5-hexenoic acid

To a suspension of 1 g of 1,4-dimethoxy-3-methylnaphthalene-2-carbaldehyde and 3.85 g of (4-carboxybutyl)triphenylphosphonium bromide in 2.5% t-BuOH/toluene at 60° C. was added 1.95 g of potassium t-butoxide. The mixture was stirred at 60° C. for 30 min, extracted with 1N NaOH, and washed with toluene. The aqueous layer was neutralized with iN HCl until pH 4–5, then extracted with ethyl acetate. The organic layer was washed, dried, and concentrated, then the trsidue was purified with column chromatography over silica gel using n-hexane/ethyl acetate (2/1) as an eluent to give 0.9 g of the titled compound as an oil.

$^1$H-NMR (CDCl$_3$) δ: 1.80–1.98 (2H, m), 2.24–2.57 (7H, m), 3.77 (s, O-Me of Z isomer), 3.81 (s, O-Me of E isomer), 3.87 (s, O-Me of E isomer), 3.88 (s, O-Me of Z isomer), 5.86 (dt, J=11 Hz, 7 Hz, olefinic H of Z isomer), 6.21 (dt, J=16 Hz, 6.8 Hz, olefinic H of E isomer), 6.43 (d, J=11 Hz, olefinic H of Z isomer), 6.54 (d, J=16 Hz, olefinic H of E isomer), 7.42–7.50 (2H, m), 8.00–8.13 (2H, m).

4) Methyl 6-(1,4-Dimethoxy-3-methylnaphthalen-2-yl)-6-(4-hydroxyphenyl)hexanoate To a solution of 25.6 g of 6-(1,4-dimethoxy-3-methylnaphthalen-2-yl)-5-hexenoic acid and 23 g of phenol in 250 ml of methylene chloride was added 20.6 ml of boron trifluoride diethyl ether complex at 0° C. The solution was stirred at room temperature for 24 hours and poured into ice-water. The organic layer was separated, washed, dried, and evaporated. The residue was dissolved in 400 ml of methanol and 8 ml of c.HCl . The solution was heated at 60° C. for 1 hour, and the solvent was removed by evaporation. The residue was purified with column chromatography over silica gel using n-hexane/ethyl acetate (7/1–2/1) as an eluent to give 20.5 g of the titled compound as an oil.

$^1$H-NMR (CDCl$_3$) δ: 1.64–1.82 (4H, m), 2.05–2.43 (7H, m), 3.46–3.70 (6H, br), 3.84 (3H, s), 4.57–4.84 (1H, br), 5.35 (1H, s), 6.71 (2H, d, J=8.4 Hz), 7.09 (2H, d, J=8.4 Hz), 7.40–7.53 (2H, m), 7.97–8.10 (2H, m).

5) Methyl 6-(1,4-Dimethoxy-3-methylnaphthalen-2-yl)-6-(4-methoxyphenyl)hexanoate To a solution of 20.5 g of methyl 6-(1,4-dimethoxy-3-methylnaphthalen-2-yl)-6-(4-hydroxyphenyl)hexanoate in 200 ml of DMF at 0° C. was added 16 g of potassium carbonate followed 10 ml of methyl iodide. The suspension was stirred at 50° C. for 16 hours.

The reaction mixture was partioned with water and ethyl acetate. The organic layer was washed, dried, and evaporated. The residue was purified with column chromatography over silica gel using n-hexane/ethyl acetate (6/1) as an eluent to obtain 16.7 g of the titled compound as an oil.

$^1$H-NMR (CDCl$_3$) δ: 1.08–1.81 (4H, m), 2.05–2.50 (7H, m), 3.52–3.73 (6H, br), 3.77 (3H, s), 3.84 (3H, s), 4.66–4.87 (1H, br), 6.81 (2H, d, J=8.9 Hz), 7.17 (2H, d, J=8.9 Hz), 7.41–7.52 (2H, m), 7.98–8.11 (2H, m).

6) 6-(1,4-Dimethoxy-3-methylnaphthalen-2-yl)-6-(4-methoxyphenyl)hexanoic acid

To a solution of 17.6 g of the methyl ester in 80 ml of MeOH was added 53 ml of 3N NaOH at 60° C. The solution was stirred at 60° C. for 1 hour, and the solvent was removed by evaporation. The residue was neutralized, and extracted with ethyl acetate. The organic layer was washed, dried, and evaporated to give 17.5 g of the titled compound as a syrup.

$^1$H-NMR (CDCl$_3$) δ: 1.08–1.80 (4H, m), 2.04–2.51 (7H, m), 3.48–3.73 (3H, br), 3.77 (3H, s), 3.84 (3H, s), 4.65–4.88 (1H, br), 6.80 (2H, d, J=8.8 Hz), 7.16 (2H, d, J=8.8 Hz), 7.41–7.54 (2H, m), 7.97–8.11 (2H,m)

7) 6-(4-Methoxyphenyl)-6-(3-methyl-1,4-naphthoquinon-2-yl)hexanoic acid

To a solution of 14.7 g of 6-(1,4-Dimethoxy-3-methylnaphthalen-2-yl)-6-(4-methoxyphenyl)hexanoic acid in 300 ml of acetonitrile at 0C was added an aqueous 147 ml solution of 57.2 g of ceric ammonium nitrate portionwisely over 5 min. After stirring for 16 hours at room temperature, the solution was extracted with ethyl acetate. The organic layer was washed, dried, evaporated, and the residue was purified with column chromatography over silica gel using ethyl acetate as an eluent. Recrystallization from isopropyl ether/ethyl acetate gave 10.8 g of the title compound.

m.p. 68°–71° C.

8) 6-(4-Methoxyphenyl)-6-(3-methyl-1,4-naphthoquinon-2-yl)hexanohydroxamic acid

To a suspension of 10.8 g of 6-(4-methoxyphenyl)-6-(3-methyl-1,4-naphthoquinon-2-yl)hexanoic acid in 250 ml of toluene was added 10.2 ml of oxalyl chloride and stirred at 50° C. for 1 hour. The reaction mixture was concentrated and dissolved in dried THF. To a solution of 5.2 g of hydroxylammonium chloride in 140 ml of saturated NaHCO$_3$aq.in ice-water bath was added a THF solution of acid chloride. The mixture was stirred at 0° C. for 1 hour and extracted with ethyl acetate. The organic layer was washed, dried, evaporated, and the residue was purified with column chromatography over silica gel using n-hexane/ethyl acetate (1/2) or ethyl acetate as an eluent. Recrystallization from n-hexane/ethyl acetate (7/3) obtained 7.9 g of the titled compound.

m.p. 129°–130° C.

Reference Example 53

6-(4-Methoxyphenyl)-6-(3-methyl-1,4-naphthoquinon-2-yl)hexanoic acid 1) 1-Methoxy-3-methyl-2-naphthonitrile The suspension of 1-hydroxy-3-methyl-2-naphthonitrile (47.23 g), potassium carbonate (71.3 g), iodomethane (100 ml), and DMF (250 ml) was-stirred overnight at ambient temperature. The reaction mixture was poured into ice-water and extracted with ethyl acetate. The organic layer was washed with water, dried, and concentrated. The residue was recrystallized from water/methanol to give the titled compound (50 mg).

$^1$H-NMR (CDCl$_3$) δ: 2.63 (3H, s), 4.25 (3H, s), 7.45 (1H, s), 7.45–7.65 (2H, m), 7.77 (1H, dd, J=8.0 Hz, 1 Hz), 8.15 (1H, dd, J=8.0 Hz, 1 Hz). 2) 1-Methoxy-3-methyl-2-naphthaldehyde To a solution of 1-methoxy-3-methyl-2-naphthonitrile (50 g) in toluene (500 ml) was added diisobutyl aluminum hydride (toluene solution; 0.38 mol) at –40° C. and the solution was stirred for 1 hour at ice-cooled temperature. The reaction mixture was poured into cooled water and stirred with conc.HCl (210 ml) for 5 hours at 70° C. and cooled. The organic layer was separated, washed with water, dried, and evaporated to give the titled compound (38.45 g) which was used in the next reaction without purification.

$^1$H-NMR (CDCl$_3$) δ: 2.71 (3H, s), 4.10 (3H, s), 7.42 (1H, s), 7.45–7.65 (2H, m), 7.77 (1H, d, J=7.6 Hz), 8.19 (1H, d, J=8.0 Hz), 10.76 (1H, s). 3) 6-(1-Methoxy-3-methylnaphth-2-yl)-5-hexenoic acid To a suspension of 1-methoxy-3-methyl-2-naphthaldehyde (41.7 g) and 4-carboxybutyltriphenylphosphonium bromide (184.4 g) in 2.5% t-butanol-toluene (1251 ml) was added potassium t-butoxide (103 g) at 60° C. After being stirred for 30 min, the reaction mixture was poured into cooled water, acidified with conc.HCl, and extracted with ethyl acetate. The organic layer was separated, washed with water, dried, and evaporated. The residue was stirred with potassium carbonate (200 g), iodomethane (80 ml), DMF (500 ml) overnight at ambient temperature. The reaction mixture was poured into water and extracted 5 with isopropyl ether (IPE). The organic layer was separated, washed with water, dried, and evaporated. The residue was treated with 20% ether/hexane and the precipitate of triphenylphosphine oxide was filtered off. The filtrate was concentrated and the residue was dissolved in ethanol (482 ml) and refluxed with 2.5N sodium hydroxide (482 ml) for 6 hours. Ethanol was removed and the residue was acidified with c.HCl and extracted with ethyl acetate. The organic layer was washed with water, dried, and evaporated to give the titled compound as crude oil.

4) Ethyl 6-(4-hydroxyphenyl)-6-(1-methoxy-3-methylnaphth-2-yl)hexanoate.

To a solution of 6-(1-methoxy-3-methylnaphth-2-yl)-5-hexenoic acid (70 g) and phenol (70 g) in dichloromethane (500 ml) was added boron trifluoride etherate (95 g) and the reaction mixture was stirred for 3 days at 35° C. and poured into cooled water. The organic layer was washed with water, dried, and evaporated. The residue was purified with silica gel chromatography (eluent; toluene, 20% ethyl acetate/hexane, and ethyl acetate) to give the titled compound (30 g).

$^1$H-NMR (CDCl$_3$) δ: 1.18 (3H, t, J=7.2 Hz), 1.10–1.80 (4H, m), 2.05–2.45 (7H, m), 3.60 (3H, br), 4.06 (2H, q, J=7.2 Hz), 4.60–4.75 (1H, m), 6.73 (2H, d, J=8.0 Hz), 7.11 (2H, d, J=8.0 Hz), 7.35–7.50 (3H, m), 7.68–7.76 (1H, m), 7.93–8.03 (1H, m).

5) 6-(4-Methoxyphenyl)-6-(1-methoxy-3-methylnapth-2-yl)hexanoic acid

Ethyl 6-(4-hydroxyphenyl)-6-(1-methoxy-3-methylnaphth-2-yl)hexanoate (30 g) was stirred with potassium carbonate (90 g), iodomethane (45 ml), and DMF (150 ml) overnight at ambient temperature. The reaction mixture was poured into cooled water and extracted with IPE. The organic layer was washed with water, dried, and evaporated. The residue was dissolved in ethanol (250 ml) and refluxed with 2.5N sodium hydroxide (250 ml) for 5 hours. Ethanol was removed and the residue was acidified with conc.HCl and extracted with ethyl acetate. The organic layer was washed with water, dried, and evaporated to give the titled compound (25 g) as crude oil.

$^1$H-NMR (CDCl$_3$) δ: 1.10–1.85 (4H, m), 2.05–2.50 (7H, m), 3.61 (3H, br), 3.77 (3H, s), 4.65–4.80 (1H, m), 6.80 (2H, d, J=8.8 Hz), 7.17 (2H, d, J=8.8 Hz), 7.38–7.50 (3H, m), 7.69–7.78 (1H, m), 7.95–8.05 (1H, m).

6) 6-(4-Methoxyphenyl)-6-(3-methyl-1,4-naphthoquinon-2-yl)hexanoic acid

To a solution of 6-(4-methoxyphenyl)-6-(1-methoxy-3-methylnaphth-2-yl)hexanoic acid (27 g) in 90% acetic acid (135 ml) was added a aqueous chromic anhydride (34.4 g in 34.4 ml of water) at 0° C. After 30 min, 2-propanol (20 ml) was added and the resulting solution was treated with water and extracted with ethyl acetate. The organic layer was washed with water, dried, and evaporated. The residue was purified with silica gel chromatography (eluent; toluene-and ethyl acetate/hexane). Recrystallization from IPE gave the titled compound.

Example 1

7-(2-Hydroxy-1-naphthyl)-7-phenylheptanohydroxamic acid (Compound 1–1)

Hydroxylamine hydrochloride (1.4 g) was dissolved in water (14 ml) followed by addition of sodium hydroxide (93%, 2 g) and water (7 ml). To this mixture was added a solution of ethyl 7-(2-hydroxy-1-naphthyl)-7-phenylheptanoate (1.08 g) in tetrahydrofuran (3 ml) and the mixture was stirred for 4 hours. This reaction mixture was neutralized with 1N-HCl and extracted with ethyl acetate. The organic layer was washed, dried, and concentrated, and the residue was purified using a silica gel column (chloroform-methanol) to provide the title compound (0.4 g).

The following compounds were obtained in the like manner.

Compound 1-3: 7-(2-quinolyl)heptanohydroxamic acid
Compound 1-4: (Z)-7-(2-quinolyl)-6-heptenohydroxamic acid
Compound 1-5: (E)-7-(2-quinolyl)-6-heptenohydroxamic acid
Compound 1-6: 6-(1-isoquinolyl)hexanohydroxamic acid (starting material: Reference Example 32)

Compound 1-7: 7-(1-isoquinolyl)heptanohydroxamic acid (starting material: Reference Example 31)

Example 2

6-(2-Quinolyl)hexanohydroxamic acid (compound 2-1)

To a solution of the 6-(2-quinolyl)hexanoic acid obtained in Reference Example 14 (1.2 g) and one drop of DMF in dichloromethane (5 ml) was added oxalyl chloride (1.0 ml) dropwise with ice-cooling. The mixture was further stirred at room temperature for 15 minutes. The solvent was then distilled off and the crude crystals were collected by filtration and washed with hexane. The crystals were dissolved in dichloromethane (30 ml) and the solution was added dropwise to a solution (30 ml) of hydroxylamine hydrochloride (1.0 g) in saturated aqueous sodium hydrogen carbonate solution with ice-cooling. The mixture was then stirred at room temperature for 2 hours. This reaction mixture was neutralized with 3N HCl and the resulting crystals were harvested by filtration, rinsed with water and ether, and dried in vacuo. The crude crystals thus obtained were recrystallized from methanol-ether to provide the title compound (0.34 g).

The following compounds were obtained in the like manner. The starting carboxylic acid is indicated in parentheses following each product compound name.
Compound 2-2: (E)-6-(2-Quinolyl)-5-hexenohydroxamic acid (starting material: Reference Example 13)
Compound 2-3: 6-(4-Quinolyl)hexanohydroxamic acid (starting material: Reference Example 15)
Compound 2-4: 7-(4-Quinolyl)heptanohydroxamic acid
Compound 2-5: 8-(4-Isoquinolyl)octanohydroxamic acid (starting material: Reference Example 7)
Compound 2-6: 6-(4-Chlorophenyl)-6-(3-methyl-1,4-naphthoquinon-2-yl)hexanohydroxamic acid
Compound 2-7: 6-(3-Quinolyl)hexanohydroxamic acid (starting material: Reference Example 19)
Compound 2-8: 7-(3-Quinolyl)heptanohydroxamic acid (starting material: Reference Example 20)
Compound 2-9: 7-(6-Methoxy-2-quinolyl)heptanohydroxamic acid (starting material: Reference Example 21)
Compound 2-10: 6-Phenyl-6-(2-quinolyl)hexanohydroxamic acid (starting material: Reference Example 23)
Compound 2-11: 7-Phenyl-7-(2-quinolyl)heptanohydroxamic acid (starting material: Reference Example 22)
Compound 2-12: 7-Cyano-7-(2-naphthyl)heptanohydroxamic acid (starting material: Reference Example 39)
Compound 2-13: 7-Ethoxycarbonyl-7-(1-naphthyl)heptanohydroxamic acid (starting material: Reference Example 40)
Compound 2-14: 7-(Benzothiazol-2-yl)-7-cyanoheptanohydroxamic acid (starting material: Reference Example 36)

Example 3

6-Cyano-6-(1-naphthyl)hexanohydroxamic acid (Compound 3-1)

In THF (8.5 ml)-DMF (0.1 ml) was dissolved 6-cyano-6-(1-naphthyl)hexanoic acid (4.0 g) (15 mmol) followed by dropwise addition of oxalyl chloride (3.2 ml) (37.5 mmol) at room temperature. After 15 minutes of stirring, the excess oxalyl chloride was distilled off under reduced pressure. The residue was dissolved in dichloromethane (63 ml) and the solution was added to a solution (63 ml) of hydroxylamine hydrochloride (3.13 g) (45 mmol) in saturated aqueous sodium hydrogen carbonate solution with ice-cooling. The reaction was carried out at room temperature for 2 hours, at the end of which time the reaction mixture was made weakly acidic with concentrated hydrochloric acid. The organic layer was washed with saturated aqueous sodium chloride solution (50 ml), dried over anhydrous sodium sulfate, and purified by silica gel column chromatography (hexane-ethyl acetate=1:9) to provide the title compound (4.08 g) (yield 96.3%) as colorless oil.

The following compound was obtained in the like manner.
Compound 3-2: 7-Cyano-7-(1-naphthyl)heptanohydroxamic acid Example 4

6-Benzoylamino-6-(2-naphthyl)hexanohydroxamic acid (Compound 4-1)

Ethyl 6-benzoylamino-6-(2-naphthyl)hexanoate (Reference Example 25) (0.8 g) and hydroxylamine hydrochloride (0.71 g) were suspended in methanol. To this suspension (4.2 ml) was added 4.9N sodium methoxide/methanol (4.9 ml) and the mixture was stirred at room temperature for 2 hours. This reaction mixture was diluted with water and the methanol was distilled off under reduced pressure. The residue was acidified with 3N HCl and extracted with ethyl acetate. The extract was dried over anhydrous sodium sulfate and concentrated and the crude residue was purified by silica gel column chromatography (ethyl acetate-hexane=2:1) to provide the title compound (0.32 g).

The following compounds were obtained in the like manner.
Compound 4-2: 6-acetylamino-6-(2-naphthyl)hexanohydroxamic acid (starting material: Reference Example 26)
Compound 4-3: 6-methanesulfonylamino-6-(2-naphthyl)hexanohydroxamic acid (starting material: Reference Example 28)
Compound 4-4: 6-benzenesulfonylamino-6-(2-naphthyl)hexanohydroxamic acid (starting material: Reference Example 29)
Compound 4-5: 6-(4-methylbenzenesulfonylamino)-6-(2-naphthyl)hexanohydroxamic acid (starting material: Reference Example 27)
Compound 4-6: 6-(4-fluorobenzenesulfonylamino)-6-(2-naphthyl)hexanohydroxamic acid (starting material: Reference Example 30)

Example 5

7-(4-Methoxyphenyl)-7-(3-methyl-1,4-naphthoquinon-2-yl)heptanohydroxamic acid (Compound 5)

7-(4-Methoxyphenyl)-7-(3-methyl-1,4-naphthoquinon-2-yl)heptanoic acid (2 g) (5.3 mmol) was treated with oxalyl chloride (3 ml) (35 mmol) in toluene (50 ml) to give the corresponding acid chloride. This acid chloride was dissolved in tetrahydrofuran (30 ml) and the solution was added dropwise to a solution (30 ml) of hydroxylamine hydrochloride (1.14 g) (16 mmol) in saturated aqueous sodium hydrogen carbonate solution. After completion of the reaction, the reaction mixture was extracted with ethyl acetate and the extract was concentrated. The residue was purified by silica gel column chromatography to provide the title compound (15.7 g).

Example 6

7-(3-Methyl-1,4-naphthoquinon-2-yl)-7-phenylheptanohydroxamic acid (Compound 6–1)

7-(3-Methyl-1,4-naphthoquinon-2-yl)-7-phenyl-heptanoic acid (8.1 g) (22 mmol) was treated with oxalyl chloride (12 ml) (0.14 mmol) in toluene (200 ml) to give the corresponding acid chloride. This acid chloride was dissolved in tetrahydrofuran (120 ml) and the solution was added dropwise to a solution (120 ml) of hydroxylamine hydrochloride (4.6 g) (65 mmol) in saturated aqueous sodium hydrogen carbonate solution. After completion of the reaction, the reaction mixture was extracted with ethyl acetate and the extract was concentrated. The residue was purified by silica gel column chromatography to provide the title compound (7.0 g).

The following compound was obtained in the like manner.
Compound 6-2: 6-(4-methoxyphenyl-6-(1,4-naphthoquinon-2-yl)hexanohydroxamic acid (starting material: 6-(4-methoxyphenyl)-6-(1,4-naphthoquinon-2-yl) hexanoic acid)

Example 7

1) O-Acetyl-6-(4-methoxyphenyl)-6-(3-methyl-1,4-naphthoquinon-2-yl)hexanohydroxamic acid (Compound 7-1)

6-(4-Methoxyphenyl)-6-(3-methyl-1,4-naphthoquinon-2-yl)hexanohydroxamic acid (215 mg) and pyridine (125 mg) were dissolved in THF (1 ml) followed by addition of acetic anhydride (56 mg), and the mixture was stirred at room temperature for 2 hours. This reaction mixture was diluted with ether, washed serially with 1N HCl, saturated aqueous NaCl solution, and saturated aqueous $NaHCO_3$ solution, dried, and concentrated under reduced pressure. The residue was applied to a silica gel column and developed with hexane-ethyl acetate (1:1) to provide the title compound (150 mg).

The following compounds were obtained in the like manner.
Compound 7-2: O-acetyl-7-(3,5,6-trimethylbenzoquinon-2-yl)-7-phenylheptanohydroxamic acid
Compound 7-3: O-acetyl-7-(1-hydroxy-2-naphthyl) heptano-hydroxamic acid
Compound 7-4: O-acetyl-6-(2-quinolyl)hexanohydroxamic acid
Compound 7-5: O-propionyl-7-(3,5,6-trimethylbenzoquinon-2-yl)-7-phenylheptanohydroxamic acid
Compound 7-6: O-propionyl-6-(4-methoxyphenyl)-6-(3-methyl-1,4-naphthoquinon-2-yl)hexanohydroxamic acid
Compound 7-7: O-propionyl-6-(2-quinolyl) hexanohydroxamic acid
Compound 7-8: O-propionyl-7-cyano-7-(1-naphthyl) heptanohydroxamic acid
Compound 7-9: O-isovaleryl-7-(3,5,6-trimethylbenzoquinon-2-yl)-7-phenylheptanohydroxamic acid
Compound 7-10: O-isobutyryl-6-(4-methoxyphenyl)-6-(3-methyl-1,4-naphthoquinon-2-yl)hexanohydroxamic acid
Compound 7-11: O-isobutyryl-7-(3,5,6-trimethylbenzoquinon-2-yl)-7-phenylheptanohydroxamic acid
Compound 7-12: O-benzoyl-7-cyano-7-(1-naphthyl) heptano-hydroxamic acid
Compound 7-13: O-benzoyl-6-cyano-6-(1-naphthyl) hexanohyroxamic acid
Compound 7-14: O-benzoyl-6-(4-me-Ehoxyphenyl)-6-(3-methyl-1,4-naphthoquinon-2-yl)hexanohydroxamic acid
Compound 7-15: O-benzoyl-7-(3,5,6-trimethylbenzoquinon-2-yl)-7-phenylheptanohydroxamic acid
Compound 7-16: O-benzoyl-6-(2-quinolyl) hexanohydroxamic acid
Compound 7-17: O-pivaloyl-7-(3,5,6-trimethylbenzoquinon-2-yl)-7-phenylheptanohydroxamic acid
Compound 7-18: O-cyclohexylcarbonyl-7-(3,5,6-trimethylbenzoquinon-2-yl)-7-phenylheptanohydroxamic acid 2) O-Propionyl-6-(4-methoxyphenyl)-6-(3-methyl-1,4-naphthoquinon-2-yl)hexanohydroxamic acid (Compound 7-6)

To a solution of 6-(4-methoxyphenyl)-6-(3-methyl-1,4-naphthoquinon-2-yl)hexanohydroxamic acid (2.8 g) in THF (40 ml) was added triethylamine (1.4 ml) followed by addition of propionyl chloride (669 mg) at 0° C. The reaction mixture was stirred for 1 hour and partitioned between water and ethyl acetate. The organic layer was dried and concentrated. The residue was purified with silica gel chromathography using hexane-ethyl acetate as an eluent to give the titled compound (2.1 g).

Example 8

O-Ethylcarbamoyl-6-(4-methoxyphenyl)-6-(3-methyl-1,4-naphthoquinon-2-yl)hexanohydroxamic acid (Compound 8-1)

To a solution of 6-(4-methoxyphenyl)-6-(3-methyl-1,4-naphthoquinon-2-yl)hexanohydroxamic acid (0.5 g) in THF was added a THF (2 ml) solution of ethyl isocyanate (0.1 g) at room temperature and the mixture was stirred for 2 hours. The solvent was then distilled off under reduced pressure and the residue was purified by silica gel column chromatography (hexane-ethyl acetate=1:1). The resulting oil was crystallized from hexane to provide the title compound (0.29 g).

The following compounds were obtained in the like manner.
Compound 8-2: O-ethylcarbamoyl-6-(2-quinolyl) hexanohyroxamic acid
Compound 11—11: O-carbamoyl-6-(4-methoxyphenyl)-6-(3-methyl-1,4-naphthoquinon-2-yl)hexanohydroxamic acid
Compound 11-16: O-ethylcarbamoyl-7-(3-methyl-1,4-naphthoquinon-2-yl)-7-phenylheptanohydroxamic acid

Example 9

The following compounds were synthesized by the same procedure as Example 7. The starting compound is indicated in parentheses following the product compound name.
Compound 9-1: O-benzoyl-7-(1-isoquinolyl) heptanohydroxamic acid (starting material: Compound 1-7)
Compound 9-2: O-propionyl-7-(1-isoquinolyl)heptano-hydroxamic acid (starting material: Compound 1-7)
Compound 9-3: O-benzoyl-7-(1-naphthyl) heptanohydroxamic acid
Compound 9-4: O-propionyl-7-(1-naphthyl) heptanohydroxamic acid
Compound 9-5: O-acetyl-6-(1-naphthyl)hexanohydroxamic acid
Compound 9-6: o-acetyl-6-(benzothiazol-2-yl) hexanohyroxamic acid (starting material: Reference Example 47-2)
Compound 9-7: o-propionyl-6-(1-naphthyl) hexanohydroxamic acid
Compound 9-8: O-propionyl-6-(benzothiazol-2-yl) hexanohyroxamic acid (starting material: Reference Example 47-3)
Compound 9-9: O-benzoyl-6-(benzothiazol-2-yl) hexanohyroxamic acid (starting material: Reference Example 47-1)
Compound 9-10: O-acetyl-7-cyano-7-(2-naphthyl) heptanohydroxamic acid (starting material: Compound 2-12)
Compound 9-11: O-propionyl-7-cyano-7-(2-naphthyl) heptanohydroxamic acid (starting material: Compound 2-12)

Compound 9-12: O-benzoyl-7-cyano-7-(2-naphthyl)heptanohydroxamic acid (starting material: Compound 2-12)
Compound 9-13: O-benzoyl-6-(benzoxazol-2-yl)hexanohyroxamic acid (starting material: Reference Example 47-2)
Compound 9-14: O-benzoyl-7-(benzothiazol-2-yl)heptanohydroxamic acid (starting material: Reference Example 47-3)
Compound 9-15: O-propionyl-6-(benzoxazol-2-yl)hexanohyroxamic acid (starting material: Reference Example 47-2)
Compound 9-16: O-(2-acetoxybenzoyl)-7-(benzothiazol-2-yl)heptanohydroxamic acid (starting material: Reference Example 47-3)
Compound 9-17: O-(2-acetoxybenzoyl)-6-(benzoxazol-2-yl)hexanohydroxamic acid (starting material: Reference Example 47-1)
Compound 9-18: O-propionyl-7-ethoxycarbonyl-7-(1-naphthyl)heptanohydroxamic acid (starting material: Compound 2-13)
Compound 9-19: O-acetyl-7-(2-quinolyl)heptanohydroxamic acid (starting material: Compound 1-3)
Compound 9-20: O-propionyl-7-(2-quinolyl)heptanohydroxamic acid (starting material: Compound 1-3)
Compound 9-21: O-hexanoyl-7-(2-quinolyl)heptanohydroxamic acid (starting material: Compound 1-3)
Compound 9-22: O-benzoyl-7-(2-quinolyl)heptanohydroxamic acid (starting material: Compound 1-3)
Compound 9-23: O-(4-fluorobenzoyl)-7-(2-quinolyl)heptanohydroxamic acid (starting material: Compound 1-3)
Compound 9-24: O-[2-(4-isobutylphenyl)propionyl]-7-(2-quinolyl)heptanohydroxamic acid (starting material: Compound 1-3)

Example 10

O-Hexanoyl-7-(1-nitro-2-naphthyl)heptanohydroxamic acid (Compound 10)

7-(1-Nitro-2-naphthyl)heptanohydroxamic acid (0.7 g) was treated in the same manner as Example 7 to provide the title compound (0.54 g).

Example 11

O-Propionyl-5-(3-methyl-1,4-naphthoquinon-2-yl)-5-phenylpentanohydroxamic acid (Compound 11-1)

5-(3-Methyl-1,4-naphthoquinon-2-yl)-5-phenylpentanohydroxamic acid was treated in the same manner as Example 7 to provide the title compound.

The following compounds were obtained in the like manner.

Compound 11-2: O-acetyl-6-(3-methyl-1,4-naphthoquinon-2-yl)-6-phenylhexanohydroxamic acid
Compound 11-3: O-propionyl-6-(3-methyl-1,4-naphthoquinon-2-yl)-6-phenylhexanohydroxamic acid
Compound 11-4: O-benzoyl-6-(3-methyl-1,4-naphthoquinon-2-yl)-6-phenylhexanohydroxamic acid
Compound 11-5: O-acetyl-6-(4-fluorophenyl)-6-(3,5,6-trimethyl-1,4-benzoquinon-2-yl)hexanohydroxamic acid
Compound 11-6: O-propionyl-6-(4-fluorophenyl)-6-(3,5,6-trimethyl-1,4-benzoquinon-2-yl)hexanohydroxamic acid
Compound 11-7: O-hexanoyl-6-(4-methoxyphenyl)-6-(3-methyl-1,4-naphthoquinon-2-yl)hexanohydroxamic acid
Compound 11-8: O-cyclohexanecarbonyl-6-(4-methoxyphenyl)-6-(3-methyl-1,4-naphthoquinon-2-yl)hexanohydroxamic acid
Compound 11-9: O-diphenylacetyl-6-(4-methoxyphenyl)-6-(3-methyl-1,4-naphthoquinon-2-yl)hexanohydroxamic acid
Compound 11-10: O-(3,3-diphenylpropionyl)-6-(4-methoxy-phenyl)-6-(3-methyl-1,4-naphthoquinon-2-yl)hexanohyroxamic acid
Compound 11-12: O-propionyl-7-(4-methoxyphenyl)-7-(3-methyl-1,4-naphthoquinon-2-yl)heptanohydroxamic acid
Compound 11-13: o-benzoyl-7-(4-methoxyphenyl)- 7-(3-methyl-1,4-naphthoquinon-2-yl)heptanohydroxamic acid
Compound 11-14: O-propionyl-7-(3-methyl-1,4-naphthoquinon-2-yl)-7-phenylheptanohydroxamic acid
Compound 11-15: O-benzoyl-7-(3-methyl-1,4-naphthoquinon-2-yl)-7-phenylheptanohydroxamic acid
Compound 11-17: O-propionyl-7-(4-fluorophenyl)-7-(3-methyl-1,4-naphthoquinon-2-yl)heptanohydroxamic acid
Compound 11-18: O-benzoyl-7-(4-fluorophenyl)-7-(3-methyl-1,4-naphthoquinon-2-yl)heptanohydroxamic acid
Compound 11-19: O-propionyl-6-(4-methoxyphenyl)-6-(1,4-naphthoquinon-2-yl)hexanohydroxamic acid
Compound 11-20: O-benzoyl-6-(4-methoxyphenyl)-6-(1,4-naphthoquinon-2-yl)hexanohydroxamic acid The structural formulas and NMR spectra of the compounds obtained in the above Reference Examples and Examples are presented in the following tables.

TABLE 1

$$\underset{R^1}{\overset{Ar\ (H)_m}{>}}=C(H)_{m+1}-(CH_2)_n-CO-NH-OR^2$$

| Ref. Ex. No. | Ar | $R^1$ | $R^2$ | m | n | m.p. (°C.) | NMR (δ; CDCl$_3$) |
|---|---|---|---|---|---|---|---|
| 46-1 | 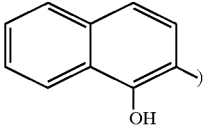 | Ph | H | 1 | 4 | 94–96 | (DMSO-d$_6$): 1.20–1.70(8H, m), 1.95 (2H, t, J=7.4Hz), 2.74(2H, t, J=7Hz), 7.20–7.50(4H, m), 7.72–7.82(1H, m), 8.13–8.25(1H, m) |
| 46-2 | 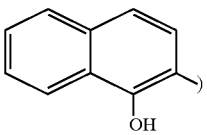 | H | H | 1 | 3 | 118–120 | (DMSO-d$_6$): 1.20–1.70(6H, m), 1.95 (2H, t, J=7Hz), 2.74(2H, t, J=7Hz), 7.26 (1H, d, J=8Hz), 7.36(1H, d, J=8Hz), 7.36–7.50(2H, m), 7.72–7.84(1H, m), 8.13–8.27(1H, m) |

TABLE 2

$$\text{Ar} \diagdown_{R^1} \text{(H)}_m \diagup \!\!\!=\!\! C(H)_{m+1}\!-\!(CH_2)_n\!-\!CO\!-\!NH\!-\!OR^2$$

| Ref. Ex. No. | Ar | R¹ | R² | m | n | m.p. (°C.) | NMR (δ; CDCl₃) |
|---|---|---|---|---|---|---|---|
| 46-3 | 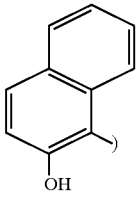 (naphthyl-OH) | H | H | 1 | 4 | 131–133 | (DMSO-d₆); 1.20–1.60(8H, m), 1.95 (2H, t, J=7Hz), 2.89–3.02(2H, m), 7.17 (1H, d, J=9Hz), 7.20–7.30(1H, m), 7.28–7.50(1H, m), 7.61(1H, d, J=9Hz), 7.77 (1H, d, J=7Hz), 7.87(1H, d, J=9Hz), 8.66 (1H, brs), 9.44(1H, s), 10.34(1H, brs) |
| 46-4 | 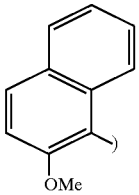 (naphthyl-OMe) | H | H | 1 | 4 | oily substance | 1.30–1.80(8H, m), 2.12(2H, m), 3.05 (2H, m), 3.93(3H, s), 7.20–7.52(3H, m), 7.66–7.80(2H, m), 7.87–7.97(1H, m) |
| 46-5 | 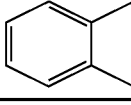 (2-naphthyl) | H | H | 1 | 4 | 112–113 | (DMSO-d₆); 1.20–1.75(8H, m), 1.94 (2H, t, J=7Hz), 2.73(2H, t, J=7Hz), 7.33–7.52(3H, m), 7.68(1H, s), 7.78–7.90 (3H, m) |

TABLE 3

$$\text{Ar} \diagdown_{R^1} \text{(H)}_m \diagup \!\!\!=\!\! C(H)_{m+1}\!-\!(CH_2)_n\!-\!CO\!-\!NH\!-\!OR^2$$

| Ref. Ex. No. | Ar | R¹ | R² | m | n | m.p. (°C.) | NMR (δ; CDCl₃) |
|---|---|---|---|---|---|---|---|
| 47-1 | 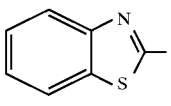 (benzothiazol-2-yl) | H | H | 1 | 3 | 146–148 | 1.40–1.58(2H, m), 1.62–1.99(4H, m), 2.14(2H, t, J=7.3Hz), 3.11(2H, t, J=7.7Hz), 7.31–7.50(2H, m), 7.85(1H, dd, J=7.5, 1.5Hz), 7.96(1H, dd, J=7.7, 1.5Hz), 8.33(1H, brs), 10.02(1H, brs.) |
| 47-2 | 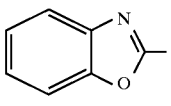 (benzoxazol-2-yl) | H | H | 1 | 3 | 107–109 | 1.40–1.57(2H, m), 1.64–1.97(4H, m), 2.17(2H, t, J=7.2Hz), 2.93(2H, t, J=7.5Hz), 7.27–7.34(2H, m), 7.44–7.50(1H, m), 7.63–7.70(1H, m), 8.18(1H, brs), 9.94(1H, brs.) |
| 47-3 | 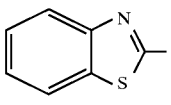 (benzothiazol-2-yl) | H | H | 1 | 4 | 120–122 | 1.34–1.55(4H, m), 1.57–1.73(2H, m), 1.77–1.94(2H, m), 2.12(2H, t, J=7.5Hz), 3.11(2H, t, J=7.7Hz), 7.31–7.50(2H, m), 7.82–7.87(1H, m), 7.93–7.98(1H, m) 8.41(1H, s), 10.03(1H, brs.) |
| 47-4 | 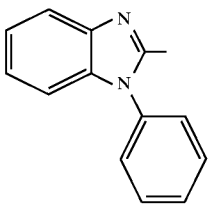 (1-phenylbenzimidazol-2-yl) | H | H | 1 | 3 | 163–165 | 1.32–1.46(2H, m), 1.67–1.84(4H, m), 2.14(2H, t, J=7.0Hz), 2.77(2H, t, J=7.3Hz), 7.06–7.38(7H, m), 7.50–7.63(4H, m), 7.82(1H, d, J=7.8Hz). |

TABLE 4

$$\begin{array}{c}\text{Ar} \quad (H)_m \\ \phantom{xxxx}\diagdown \\ \phantom{xxxxxx}C=C(H)_{m+1}-(CH_2)_n-CO-NH-OR^2 \\ \phantom{xxxx}\diagup \\ R^1 \end{array}$$

| Ref. Ex. No. | Ar | R¹ | R² | m | n | m.p. (°C.) | NMR (δ; CDCl₃) |
|---|---|---|---|---|---|---|---|
| 47-5 | 2-methyl-thiazolo[5,4-b]pyridin-yl | H | H | 1 | 3 | 110–112 | 1.41–1.57(2H, m), 1.65–1.71(2H, m), 1.73–1.97(2H, m), 2.16(2H, t, J=7.3Hz), 3.13(2H, t, J=7.6Hz), 7.41(1H, dd, J=8.2, 4.7Hz), 8.19(1H, dd, J=8.2, 1.5Hz), 8.40(1H, br), 8.54(1H, dd, J=4.7, 1.5Hz), 9.98(1H, brs). |
| 48 | 1-NO₂-naphthalen-2-yl | H | H | 1 | 4 | 69–72 | 1.20–1.45(4H, m), 1.50–1.80(4H, m), 2.14(2H, t, J=7Hz), 2.72(2H, t, J=7Hz), 7.37(1H, d, J=9Hz), 7.40–7.73(3H, m), 7.83–7.93(2H, m). |
| 49 | 1-NH₂-naphthalen-2-yl | H | H | 1 | 4 | 105–108 | (DMSO-d₆); 1.25–1.80(8H, m), 2.06(2H, t, J=7Hz), 2.66(2H, t, J=7Hz), 7.17(2H, s), m 7.30–7.45(2H, m), 7.70(1H, m), 7.96(1H, m). |
| 50 | 1-NHMs-naphthalen-2-yl | H | H | 1 | 4 | 133–136 | (DMSO-d₆); 1.20–1.70(8H, m), 1.94(2H, t, J=7Hz), 2.90(2H, t, J=7Hz), 3.06(3H, s); 7.40–7.65(3H, m), 7.85(1H, t, J=8Hz), 7.91(1H, t, J=8Hz), 8.20(1H, t, J=8Hz). |
| 51 | 1-NHTs-naphthalen-2-yl | H | H | 1 | 4 | 78–81 | (DMSO-d₆); 1.00–1.55(8H, m), 1.92(2H, t, J=7Hz), 2.38(3H, s), 2.50(2H, t, J=7Hz), 7.25–7.50(5H, m), 7.53(2H, d, J=8Hz), 7.70–7.90(3H, m). |

TABLE 5

$$\begin{array}{c}\text{Ar} \quad (H)_m \\ \phantom{xxxx}\diagdown \\ \phantom{xxxxxx}C=C(H)_{m+1}-(CH_2)_n-CO-NH-OR^2 \\ \phantom{xxxx}\diagup \\ R^1 \end{array}$$

| Cpd. No. | Ar | R¹ | R² | m | n | m.p. (°C.) | NMR (δ; CDCl₃) |
|---|---|---|---|---|---|---|---|
| 1-1 | 2-OH-naphthalen-1-yl | Ph | H | 1 | 4 | oily substance | 1.05–1.60(6H, m), 1.82–1.97(2H, m) 2.15–2.45(2H, m), 9.42–5.05(1H, m), 7.00–7.45(8H, m), 7.52–7.75(2H, m), 7.83–7.95(1H, m) |
| 1-2 | 1-OH-naphthalen-2-yl | Ph | H | 1 | 4 | oily substance | 1.15–1.60(6H, m), 1.90–2.15(4H, m), 4.28–4.41(1H, m), 7.10–7.48(9H, m), 7.68–7.79(1H, m), 8.00–8.12(1H, m) |
| 1-3 | quinolin-2-yl | H | H | 1 | 4 | 139–141 | (DMSO-d₆); 1.20–1.60(6H, m), 1.65–1.85(2H, m), 1.94(2H, t, J=7Hz), 2.90(2H, t, J=7Hz), 7.43(1H, d, J=8Hz), 7.48–7.60(1H, m), 7.65–7.78(1H, m), 8.25(1H, d, J=8Hz) |

TABLE 6

$$\underset{R^1}{\overset{Ar\ (H)_m}{\diagup}}\!\!=\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ; CDCl₃) |
|---|---|---|---|---|---|---|---|
| 1-4 | 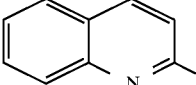 | H | H | 0(Z) | 4 | 117–120 | (DMSO-d₆); 1.35–1.70(4H, m), 2.00 (2H, t, J=7Hz), 2.70–2.90(2H, m), 6.01 (1H, dt, J=12Hz), 7Hz), 6.62(1H, d, J=12 Hz), 7.48(1H, d, J=8Hz), 7.50–7.63(1H, m), 7.68–7.70(1H, m), 7.88–8.02(2H, m). |
| 1-5 | 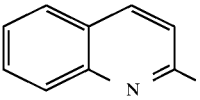 | H | H | 0(E) | 4 | 152–154 | (DMSO-d₆); 1.40–1.70(4H, m), 2.01(2H, t, J=7Hz), 2.23–2.40(2H, m), 6.68(1H, d, J=16Hz), 6.92(1H, dt, J=16Hz, 7Hz), 7.48–7.58(1H, m), 7.65–7.78(1H, m), 7.70(1H, d, J=8Hz), 7.87–7.98(2H, m), 8.28(1H, d, J=8Hz) |

TABLE 7

$$\underset{R^1}{\overset{Ar\ (H)_m}{\diagup}}\!\!=\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ; CDCl₃) |
|---|---|---|---|---|---|---|---|
| 1-6 | 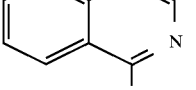 | H | H | 1 | 3 | 142–144 | (DMSO-d₆); 1.33–1.48(2H, m), 1.48–1.66 (2H, m), 1.71–1.88(2H, m), 1.96(2H, t, J= 7.1Hz), 3.24(2H, t, J=7.6Hz), 7.63–7.78 (3H, m), 7.94(1H, d, J=7.7Hz), 8.24(1H, d, J=8.1Hz), 8.38(1H, d, J=5.5Hz), 8.66 (1H, brs), 10.33(1H, brs) |
| 1-7 | 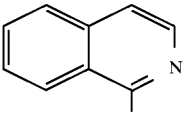 | H | H | 1 | 4 | 146–148 | (DMSO-d₆); 1.23–1.59(6H, m), 1.69–1.88 (2H, m), 1.95(2H, t, J=7.1Hz), 3.25(2H, t, J=7.7Hz), 7.62–7.79(3H, m), 7.94(1H, dd, J=1.5, 8.8Hz), 8.25(1H, d, J=8.4Hz), 8.38 (1H, d, J=5.9Hz), 8.66(1H, brs), 10.33 (1H, brs) |

TABLE 8

$$\underset{R^1}{\overset{Ar\ (H)_m}{\diagup}}\!\!=\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ; CDCl₃) |
|---|---|---|---|---|---|---|---|
| 2-1 | 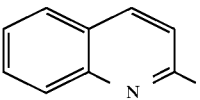 | H | H | 1 | 3 | 153–155 | 1.28–1.40(2H, m), 1.48–1.64(2H, m), 1.69–1.84(2H, m), 1.95(2H, t, J=7.3Hz), 2.91(2H, t, J=7.7Hz), 7.44(1H, d, J= 8.4Hz), 7.49–7.57(1H, m), 7.67– 7.76(1H, m), 7.90–7.96(2H, m), 8.26(1H, d, J=8.4Hz), 8.66(1H, brs) |
| 2-2 | 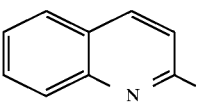 | H | H | 0(E) | 3 | 109–112 | 1.68–1.82(2H, m), 2.06(2H, t, J=7.2Hz), 2.24–2.35(2H, m), 6.66(1H, d, J=16.1Hz), 6.93(1H, dt, J=16.1, 6.9Hz), 7.49– 7.57(1H, m), 7.67–7.76(1H, m), 7.89– 7.95(2H, m), 8.28(1H, d, J=8.4Hz), 8.71(1H, brs), 10.40(1H, brs) |

TABLE 9

$$\text{Ar}\diagdown\text{C(H)}_{m+1}-(CH_2)_n-CO-NH-OR^2 \text{ with } (H)_m, R^1$$

| Cpd. No. | Ar | $R^1$ | $R^2$ | m | n | m.p. (°C.) | NMR (δ; CDCl$_3$) |
|---|---|---|---|---|---|---|---|
| 2-3 | 4-quinolyl | H | H | 1 | 3 | 154–156 | 1.33–1.47(2H, m), 1.48–1.68(2H, m), 1.63–1.74(2H, m), 1.96(2H, t, J=6.8Hz), 3.07(2H, t, J=7.5Hz), 7.38(1H, d, J=4.4Hz), 7.59–7.69(1H, m), 7.71–7.79(1H, m), 8.02(1H, dd, J=1.4, 8.3Hz), 8.14(1H, dd, J=1.2, 8.6Hz), 8.66(1H, brs) |
| 2-4 | 4-quinolyl | H | H | 1 | 4 | 114–116 | 1.22–1.44(4H, m), 1.44–1.58(2H, m), 1.58–1.76(2H, m), 1.95(2H, t, J=7.3Hz), 3.07(2H, t, J=7.5Hz), 7.35(1H, d, J=4.4Hz), 7.55–7.67(1H, m), 7.67–7.78(1H, m), 8.02(1H, d, J=8.4Hz), 8.13(1H, d, J=8.4Hz), 8.66(1H, brs), 8.77(1H, d, J=4.4Hz), 10.36(1H, brs) |

TABLE 10

$$\text{Ar}\diagdown\text{C(H)}_{m+1}-(CH_2)_n-CO-NH-OR^2 \text{ with } (H)_m, R^1$$

| Cpd. No. | Ar | $R^1$ | $R^2$ | m | n | m.p. (°C.) | NMR (δ; CDCl$_3$) |
|---|---|---|---|---|---|---|---|
| 2-5 | 4-isoquinolyl | H | H | 1 | 5 | 107–110 | (DMSO-d$_6$); 1.15–1.75(10H, m), 1.93(2H, t, J=7Hz), 3.01(2H, t, J=7Hz), 7.62–7.73(1H, m), 7.77–7.89(1H, m), 8.04–8.16(2H, m), 8.36(1H, s), 9.17(1H, s) |
| 2-6 | 2-methyl-1,4-naphthoquinon-3-yl | 4-chlorophenyl | H | 1 | 3 | amorphous | 1.18–1.42(2H, m), 1.61–1.80(2H, m), 2.06–2.31(2H, m), 2.22(3H, s), 4.39(1H, t, J=7.9Hz), 7.25(4H, s), 7.67–7.71(2H, m), 7.98–8.07(2H, m) |

TABLE 11

$$\text{Ar}\diagdown\text{C(H)}_{m+1}-(CH_2)_n-CO-NH-OR^2 \text{ with } (H)_m, R^1$$

| Cpd. No. | Ar | $R^1$ | $R^2$ | m | n | m.p. (°C.) | NMR (δ; CDCl$_3$) |
|---|---|---|---|---|---|---|---|
| 2-7 | 3-quinolyl | H | H | 1 | 3 | 181–183 | (DMSO-d$_6$); 1.22–1.41(2H, m), 1.48–1.61(2H, m), 1.61–1.77(2H, m), 1.96(2H, t, J=7.3Hz), 2.78(2H, t, J=7.5Hz), 7.57(1H, dd, J=7.0, 8.1Hz), 7.70(1H, ddd, J=1.5, 7.0, 8.0Hz), 7.92(1H, dd, J=1.5, 8.1Hz), 7.99(1H, d, J=8.0Hz), 8.13(1H, d, J=1.6Hz), 8.68(1H, brs), 8.79(1H, d, J=1.6Hz), 10.35(1H, brs) |

TABLE 11-continued $$\text{Ar} \diagdown_{R^1} C(H)_m =C(H)_{m+1}-(CH_2)_n-CO-NH-OR^2$$

| Cpd. No. | Ar | R¹ | R² | m | n | m.p. (°C.) | NMR (δ; CDCl₃) |
|---|---|---|---|---|---|---|---|
| 2-8 | 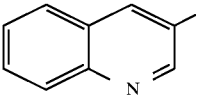 | H | H | 1 | 4 | 155–158 | (DMSO-d₆); 1.25–1.40(4H, m), 1.42–1.60(2H, m), 1.60–1.75(2H, m), 1.94(2H, t, J=7.0Hz), 2.78(2H, t, J=7.5Hz), 7.57(1H, dd, J=6.6, 8.1Hz), 7.70(1H, ddd, J=1.5, 6.6, 8.4Hz), 7.92(1H, dd, J=1.5, 8.1Hz), 8.07(1H, d, J=8.4Hz), 8.13(1H, d, J=1.8Hz), 8.68(1H, brs), 8.79(1H, d, J=1.8Hz), 10.35(1H, brs) |
| 2-9 | 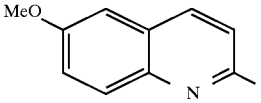 | H | H | 1 | 4 | 177–179 | (DMSO-d₆); 1.25–1.39(4H, m), 1.41–1.56(2H, m), 1.64–1.81(2H, m), 1.93(2H, t, J=7.1Hz), 2.85(2H, t, J=7.5Hz), 3.88(3H, s), 7.30–7.39(3H, m), 7.83(1H, d, J=9.2Hz), 8.14(1H, d, J=8.4Hz), 8.65(1H, brs), 10.32(1H, brs) |
| 2-10 | 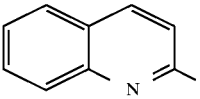 | Ph | H | 1 | 3 | 143–145 | (DMSO-d₆); 1.15–1.58(4H, m), 2.08–2.31(4H, m), 4.71(1H, t, J=7.7Hz), 7.12–7.43(6H, m), 7.52(1H, dd, J=7.0, 8.6Hz), 7.68(1H, dd, J=7.0, 8.4Hz), 8.08–8.17(3H, m), 8.90(1H, brs), 10.30(1H, brs) |

TABLE 12

$$\text{Ar} \diagdown_{R^1} C(H)_m =C(H)_{m+1}-(CH_2)_n-CO-NH-OR^2$$

| Cpd. No. | Ar | R¹ | R² | m | n | m.p. (°C.) | NMR (δ; CDCl₃) |
|---|---|---|---|---|---|---|---|
| 2-11 | 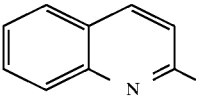 | Ph | H | 1 | 4 | non-crystal powder | (DMSO-d₆); 1.13–1.36(4H, m), 1.36–1.56(2H, m), 1.90(2H, t, J=7.0Hz), 2.01–2.20(1H, m), 2.20–2.44(1H, m) 4.25(1H, t, J=7.7Hz), 7.12–7.34(3H, m), 7.36–7.49(3H, m), 7.54(1H, dd, J=7.0, 8.4Hz), 7.73(1H, dd, J=7.0, 8.4Hz), 7.90(1H, d, J=8.1Hz), 8.00(1H, d, J=1.8Hz), 8.23(1H, d, J=8.4Hz), 8.66(1H, brs), 10.31(1H, brs) |
| 2-12 | 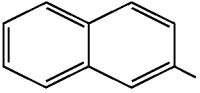 | CN | H | 1 | 4 | non-crystal powder | 1.35–1.73(6H, m), 1.92–2.03(2H, m), 2.05–2.18(2H, m), 3.95(1H, t, J=7.3Hz), 7.35–7.41(1H, m), 7.49–7.57(2H, m), 7.80–7.89(4H, m), 8.41(1H, brs) |
| 2-13 | 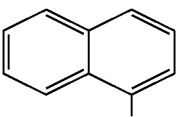 | CO₂Et | H | 1 | 4 | oily substance | 1.14(3H, t, J=7.1Hz), 1.22–1.38(4H, m), 1.46–1.65(2H, m), 1.73–1.93(1H, m), 2.00–2.29(3H, m), 4.03–4.17(2H, m), 4.32(1H, dd, J=7.8, 3.8Hz), 7.38–7.56(4H, m), 7.74(1H, brd, J=7.8Hz), 8.90(1H, brs) |
| 2-14 | 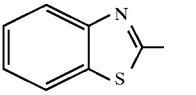 | CN | H | 1 | 4 | oily substance | 1.28–1.46(4H, m), 1.52–1.73(2H, m), 2.06 . 2.27(4H, m), 4.38(1H, t, J=7.3Hz), 7.40–7.55(2H, m), 7.83–7.90(1H, m), 8.00–8.06(1H, m) 9.02(1H, brs) |

TABLE 13

$$\text{Ar}\overset{(H)_m}{\underset{R^1}{\diagdown}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ: CDCl₃) |
|---|---|---|---|---|---|---|---|
| 3-1 | 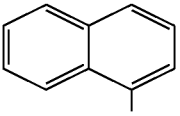 | CN | H | 1 | 3 | oily substance | 1.52–1.77(4H, m), 1.93–2.06(2H, m), 2.08–2.16(2H, m), 4.51(1H, t, J=7.1Hz), 7.40–7.64(4H, m), 7.77–7.91(3H, m), 9.12(1H, br) |
| 3-2 | 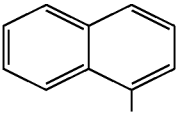 | CN | H | 1 | 4 | oily substance | 1.22–1.73(6H, m), 1.93–2.15(4H, m), 4.51(1H, t, J=7.0Hz), 7.42–7.66(4H, m), 7.79–7.91(3H, m), 8.83(1H, br) |

TABLE 14

$$\text{Ar}\overset{(H)_m}{\underset{R^1}{\diagdown}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ: CDCl₃) |
|---|---|---|---|---|---|---|---|
| 4-1 | 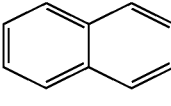 | PhCONH | H | 1 | 3 | 158–161 | (DMSO-d₆); 1.16–1.46(2H, m), 1.47–1.64(2H, m), 1.84–2.01(4H, m), 5.10–5.23(1H, m), 7.41–7.64(6H, m), 7.83–7.95(6H, m), 8.67(1H, brs), 8.87(1H, d, J=8.7Hz), 10.33(1H, brs). |
| 4-2 | 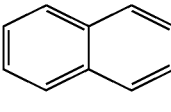 | MeCONH | H | 1 | 3 | non-crystal powder | (DMSO-d₆); 1.13–1.41(2H, m), 1.42–1.61(2H, m), 1.67–1.81(2H, m), 1.86(3H, s), 1.86–2.01(2H, m), 4.83–4.95(1H, m), 7.43–7.55(3H, m), 7.76(1H, s), 7.84–7.91(3H, m), 8.36(1H, d, J=7.9Hz), 8.67(1H, brs), 10.32(1H, brs). |
| 4-3 | 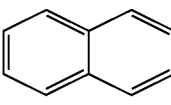 | MeSO₂NH | H | 1 | 3 | non-crystal powder | (DMSO-d₆); 1.14–1.38(2H, m), 1.42–1.59(2H, m), 1.64–1.82(2H, m), 1.91(2H, t, J=7.0Hz), 2.50(3H, s), 4.35–4.48(1H, m), 7.46–7.64(3H, m), 7.78–7.96(5H, m), 8.66(1H, brs), 10.31(1H, brs). |
| 4-4 | 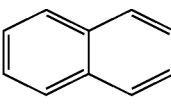 | PhSO₂NH | H | 1 | 3 | non-crystal powder | (DMSO-d₆); 0.93–1.25(2H, m), (1.28–1.48(2H, m), 1.56–1.73(2H, m), 1.82(2H, t, J=7.1Hz), 4.26–4.39(1H, m), 7.21–7.38(4H, m), 7.41–7.52(2H, m), 7.54–7.85(6H, m), 8.31(1H, d, J=8.4Hz), 8.65(1H, brs), 10.29(1H, brs). |
| 4-5 | 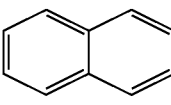 | 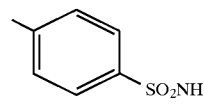 | H | 1 | 3 | non-crystal powder | (DMSO-d₆); 0.95–1.29(2H, m), 1.31–1.48(2H, m), 1.57–1.74(2H, m), 1.82(2H, t, J=7.3Hz), 2.10(3H, s), 4,27(1H, m), 6.99(2H, d, J=8.1Hz), 7.25–7.37(1H, m), 7.38–7.52(5H, m), 7.65–7.85(3H, m), 8.18(1H, d, J=8.8Hz), 8.64(1H, brs), 10.27(1H, brs). |

TABLE 15

$$\text{Ar} \diagdown_{R^1} \!\!\!\!{}^{(H)_m}\!\!\! = C(H)_{m+1} - (CH_2)_n - CO - NH - OR^2$$

| Cpd. No. | Ar | R¹ | R² | m | n | m.p. (°C.) | NMR (δ: CDCl₃) |
|---|---|---|---|---|---|---|---|
| 4-6 | 2-naphthyl | F | 4-(H₂NSO₂)-phenyl | H | 1 | 3 | non-crystal powder | (DMSO-d₆); 0.93–1.23(2H, m), 1.33–1.52(2H, m), 1.58–1.76(2H, m), 1.85(2H, t, J=7.1Hz), 4.26–4.38(1H, m), 6.93–7.07(2H, m), 7.28(1H, dd, J=1.6, 8.6Hz), 7.43–7.62(5H, m), 7.68(1H, d, J=8.9Hz), 7.72–7.82(2H, m), 8.35(1H, d, J=8.7Hz), 8.65(1H, brs), 10.30(1H, brs). |
| 5 | 2,3-dimethyl-1,4-naphthoquinon-2-yl | Me | 4-MeO-phenyl | H | 1 | 4 | non-crystal powder | 1.20–1.44(4H, m), 1.50–1.69(2H, m), 2.02–2.27 (7H, m), 3.76(3H, s), 4.38(1H, t, J=7.8Hz), 6.82 (2H, d, J=8.5Hz), 7.24(2H, d, J=8.5Hz), 7.62–7.72(2H, m), 7.96–8.09(2H, m), 8.59(1H, br., NH) |
| 6-1 | 2,3-dimethyl-1,4-naphthoquinon-2-yl | Me | phenyl | H | 1 | 4 | non-crystal powder | 1.21–1.40(4H, m), 1.49–1.68(2H, m), 2.04–2.31 (7H, m), 4.45(1H, t, J=7.6Hz), 7.11–7.35(5H, m), 7.60–7.70(2H, m), 7.92–8.09(2H, m), 8.74 (1H, br., NH) |
| 6-2 | 2-methyl-1,4-naphthoquinon-3-yl | H | 4-MeO-phenyl | H | 1 | 3 | non-crystal powder | 1.22–1.38(2H, m), 1.57–1.76(2H, m), 1.78–1.94 (2H, m), 2.01–2.16(2H, m), 3.75(3H, s), 4.21(1H, t, J=8.7Hz), 6.79(1H, s), 6.82(2H, d, J=8.7Hz), 7.17(2H, d, J=7Hz), 7.63–7.72(2H, m), 7.96–8.05(2H, m), 8.92(1H, br, NH) |

TABLE 16

$$\text{Ar} \diagdown_{R^1} \!\!\!\!{}^{(H)_m}\!\!\! = C(H)_{m+1} - (CH_2)_n - CO - NH - OR^2$$

| Cpd. No. | Ar | R¹ | R² | m | n | m.p. (°C.) | NMR (δ: CDCl₃) |
|---|---|---|---|---|---|---|---|
| 7-1 | 2,3-dimethyl-1,4-naphthoquinon-2-yl | MeO-phenyl | Ac | 1 | 3 | oily substance | 1.25–1.55(2H, m), 1.67–1.87(2H, m), 2.15–2.35(4H, m), 2.17(3H, s), 2.23 (3H, s), 3.77(3H, s), 4.39(1H, t, J=7Hz), 6.82(2H, d, J=8Hz), 7.26(2H, d, J=8Hz), 7.62–7.72(2H, m), 7.98–8.10(2H, m) |
| 7-2 | 2,3,5,6-tetramethyl-1,4-benzoquinon-2-yl | phenyl | Ac | 1 | 4 | oily substance | 1.10–1.50(4H, m), 1.55–1.80(2H, m), 1.97(3H, s), 1.99(3H, s), 2.00–2.40(4H, m), 2.05(3H, s), 2.22(3H, s), 4.29(1H, t, J=7Hz), 7.10–7.30(5H, m) |
| 7-3 | 1-hydroxy-2-naphthyl | H | Ac | 1 | 4 | 94–96 | 1.35–1.50(4H, m), 1.55–1.80(4H, m), 2.22(3H, s), 2.24(2H, t, J=7Hz), 2.74 (2H, t, J=7Hz), 7.23(1H, d, J=8Hz), 7.34–7.53(3H, m), 7.73–7.82(1H, m), 8.09–8.19(1H, m) |

TABLE 17

$$\underset{R^1}{\overset{Ar\;(H)_m}{\diagdown}}\!\!=\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ: CDCl₃) |
|---|---|---|---|---|---|---|---|
| 7-4 | 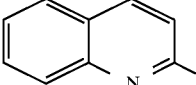 | H | Ac | 1 | 3 | 81–83 | 1.39–1.56(2H, m), 1.68–1.92(4H, m), 2.19(3H, s), 2.27(2H, t, J=7.3Hz), 2.98(2H, t, J=7.7Hz), 7.29(1H, d, J=8.8Hz), 7.49(1H, m), 7.64–7.81(2H, m), 8.08–8.10(2H, m) |
| 7-5 |  | 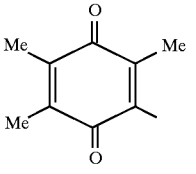 | EtCO | 1 | 4 | 94–85 | 1.23(3H, t, J=7.5Hz), 1.26–1.48(4H, m), 1.62–1.78(2H, m), 1.97(3H, s), 2.00 (3H, s), 2.01(3H, s), 2.08–2.26(4H, m), 2.52(2H, q, J=7.5Hz), 4.29(1H, t, J=7.7 Hz), 7.12–7.29(5H, m), 8.80(1H, brs) |
| 7-6 | 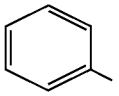 |  | EtCO | 1 | 3 | amorphous | 1.17(3H, t, J=7.5Hz), 1.25–1.51(2H, m), 1.63–1.82(2H, m), 2.18–2.34(4H, m), 2.24(3H, s), 2.46(2H, q, J=7.5Hz), 3.77 (3H, s), 4.39)1H, t, J=7.7Hz), 6.83(2H, d, J=8.4Hz), 7.26(4H, m), 7.65–7.70 (2H, m), 8.68(1H, brs) |

TABLE 18

$$\underset{R^1}{\overset{Ar\;(H)_m}{\diagdown}}\!\!=\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ: CDCl₃) |
|---|---|---|---|---|---|---|---|
| 7-7 | 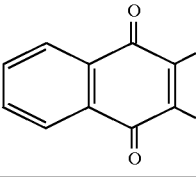 | H | EtCO | 1 | 3 | 63–65 | 1.20(3H, t, J=7.2Hz), 1.44–1.58(2H, m), 1.31–1.96(4H, m), 2.28(2H, t, J=7.3Hz), 2.49(2H, q, J=7.2Hz), 2.99(2H, t, J=7.7 Hz), 7.27(1H, d, J=8.4Hz), 7.45–7.53(1H, m), 7.65–7.72(1H, m), 7.79(1H, dd, J=1.1, 8.1Hz), 8.06(2H, m), 9.02–9.24 (1H, brs) |
| 7-8 | 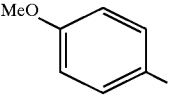 | CN | EtCH | 1 | 4 | oily substance | 1.22(3H, t, J=7.5Hz), 1.35–1.50(2H, m), 1.52–1.77(4H, m), 1.97–2.11(2H, m), 2.25(2H, t, J=7.2Hz), 2.51(2H, q, J=7.5Hz), 4.56(1H, t, J=7.1Hz), 7.45–7.72 (4H, m), 7.82–7.94(3H, m), 8.85(1H, brs) |
| 7-9 |  | 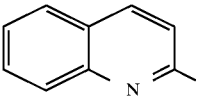 | iPrCH₂CO | 1 | 4 | 108–111 | 1.01(6H, d, J=8.3Hz), 1.44–1.58(4H, m), 1.63–1.78(2H, m), 1.97(3H, s), 2.00 (3H, s), 2.05(3H, s), 2.09–2.28(5H, m), 2.36(2H, d, J=6.8Hz), 4.29(1H, t, J=6.9 Hz), 7.12–7.33(5H, m), 8.79(1H, brs) |

TABLE 19

$$\underset{R^1}{\overset{Ar\quad (H)_m}{>}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ: CDCl₃) |
|---|---|---|---|---|---|---|---|
| 7-10 | 2,3-dimethyl-1,4-naphthoquinon-(yl) | MeO-C₆H₄- | iPrCO | 1 | 3 | amorphous | 1.20(3H, d, J=7.3Hz), 1.22(3H, d, J=7.0 Hz), 1.24–1.58(2H, m), 1.62–1.86(2H, m), 2.15–2.46(4H, m), 2.23(3H, s), 2.61–2.81(1H, m), 3.77(3H, s), 4.39(1H, t, J=7.0Hz), 6.82(2H, d, J=8.6Hz), 7.26 (2H, d, J=8.6Hz), 7.64–7.70(2H, m), 7.98–8.08(2H, m), 8.69(1H, brs) |
| 7-11 | MeO-C₆H₄- | C₆H₅- | iPrCO | 1 | 4 | 83–85 | 1.27(6H, d, J=7.0Hz), 1.29–1.48(4H, m), 1.60–1.74(2H, m), 1.97(3H, s), 2.00 (3H, s), 2.05(3H, s), 2.09–2.27(4H, m), 2.70–2.84(1H, m), 4.29(1H, t, J=7.7Hz), 7.12–7.29(5H, m), 8.71(1H, brs) |
| 7-12 | 1-naphthyl | CN | PhCO | 1 | 4 | 92–93 | 1.38–1.80(6H, m), 1.98–2.12(2H, m), 2.32(2H, t, J=7.1Hz), 4.56(1H, t, J=7.1 Hz), 7.44–7.70(7H, m), 7.82–7.93(3H, m), 8.07–8.12(2H, m), 9.16(1H, s) |

TABLE 20

$$\underset{R^1}{\overset{Ar\quad (H)_m}{>}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR (δ: CDCl₃) |
|---|---|---|---|---|---|---|---|
| 7-13 | 1-naphthyl | CN | PhCO | 1 | 3 | oily substance | 1.60–1.87(4H, m), 2.03–2,12(2H, m), 2.30–2.38(2H, m), 4.55(1H, t, J=7.2Hz), 7.42–7.70(7H, m), 7.82–7.92(3H, m), 8,08(2H, d, J=7.2Hz), 9.23(1H, brs) |
| 7-14 | 2,3-dimethyl-1,4-naphthoquinon-(yl) | MeO-C₆H₄- | PhCO | 1 | 3 | 110–112 | 1.35–1.54(2H, m), 1.71–1.91(2H, m), 2.25(3H, s), 2.26–2.37(4H, m), 3.77 (3H, s), 4.41(1H, t, J=7.7Hz), 6.82(2H, d, J=8.8Hz), 7.27(2H, d, J=8.8Hz), 7.42–7.50(2H, m), 7.59–7.67(3H, m), 7.97–8.05(4H, m), 8.93(1H, brs) |
| 7-15 | 2,3,5,6-tetramethyl-1,4-benzoquinon-(yl) | C₆H₅- | PhCO | 1 | 4 | 108–110 | 1.21–1.58(4H, m), 1.63–1.78(2H, m), 1.96(3H, s), 1.99(3H, s), 2.05(3H, s), 2.08–2.25(2H, m), 2.30(2H, t, J=7.3Hz), 4.29(1H, t, J=8.4Hz), 7.15–7.24(1H, m), 7.26–7.28(4H, m), 7.42–7.50(2H, m), 7.55–7.66(1H, m), 8.08(2H, dd, J=1.6, 7.0Hz), 9.15–9.61(1H, brs) |

TABLE 21

$$\underset{R^1}{\overset{Ar\ (H)_m}{\diagdown}}C(H)_{m+1}-(CH_2)_n-CO-NH-OR^2$$

| Cpd. No. | Ar | R¹ | R² | m | n | m.p. (°C.) | NMR (δ: CDCl₃) |
|---|---|---|---|---|---|---|---|
| 7-16 | quinoline | H | PhCO | 1 | 3 | 108–109 | 1.47–1.60(2H, m), 1.74–1.95(4H, m), 2.36(2H, t, J=7.3Hz), 3.00(2H, t, J=7.7 Hz), 7.30(1H, d, J=8.4Hz), 7.44–7.47 (3H, m), 7.59–7.80(3H, m), 8.03–8.10 (4H, m) |
| 7-17 | trimethylbenzoquinone | phenyl | tBuCO | 1 | 4 | 115–117 | 1.20–1.45(4H, m), 1.31(9H, s), 1.63–1.71(2H, m), 1.96(3H, s), 1.97(3H, s), 2.05(3H, s), 2.06–2.26(4H, m), 4.92 (1H, t, J=7.9Hz), 7.12–7.29(5H, m), 8.65(1H, brs) |
| 7-18 | trimethylbenzoquinone | phenyl | cyclohexylcarbonyl | 1 | 4 | 72–75 | 1.18–1.85(16H, m), 1.97(3H, s), 2.00 (3H, s), 2.05(3H, s), 2.07–2.36(4H, m), 2.41–2.62(1H, m), 4.28(1H, t, J=7.9Hz), 7.13–7.29(5H, m), 8.78(1H, brs) |

TABLE 22

$$\underset{R^1}{\overset{Ar\ (H)_m}{\diagdown}}C(H)_{m+1}-(CH_2)_n-CO-NH-OR^2$$

| Cpd. No. | Ar | R¹ | R² | m | n | m.p. (°C.) | NMR (δ: CDCl₃) |
|---|---|---|---|---|---|---|---|
| 8-1 | 2-methyl-naphthoquinone | MeO | EtNHCO-(4-methylphenyl) | 1 | 3 | 61–64 | 1.15(3H, t, J=7.3Hz), 1.26–1.48(2H, m), 1.63–1.82(2H, m), 2.18–2.31(4H, m), 2.23(3H, s), 3.15–3.29(2H, m), 3.77 (3H, s), 4.39(1H, t, J=7.9Hz), 5.08 (1H, brs), 6.82(2H, d, J=8.6Hz), 7.26 (2H, d, J=8.6Hz), 7.64–7.69(2H, m), 7.98–8.07(2H, m), 8.59(1H, brs) |
| 8-2 | quinoline | H | EtNHCO | 1 | 3 | 97–102 | 1.19(3H, t, J=7.3Hz), 1.42–1.60(2H, m), 1.67–1.94(4H, m), 2.72(2H, t, J=7.3Hz), 2.99(2H, t, J=7.9Hz), 3.35(2H, q, J=7.3 Hz), 7.30(1H, d, J=8.4Hz), 7.45–7.53 (1H, m), 7.65–7.81(2H, m), 8.03–8.10 (2H, m), 8.28(1H, brs), 8.81(1H, brs) |

TABLE 23

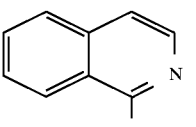

| Cpd. No. | Ar | R¹ | R² | m | n | m.p. (°C.) | NMR(δ; CDCl₃) |
|---|---|---|---|---|---|---|---|
| 9-1 | isoquinoline | H | PhCO | 1 | 4 | oily substance | 1.34–1.49(2H, m), 1.52–1.68(2H, m), 1.69–1.83(2H, m), 1.83–1.99(2H, m), 2.36(2H, t, J=7.0Hz), 3.39(2H, t, J=7.1Hz), 7.41–7.52 (2H, m), 7.53–7.73(4H, m), 7.83(1H, d, J=7.3Hz), 8.08–8.23(3H, m), 8.43(1H, d, J=5.9Hz), 10.62(1H, brs). |

TABLE 23-continued $$\underset{R^1}{\overset{Ar\ (H)_m}{\diagdown}}{=}C(H)_{m+1}{-}(CH_2)_n{-}CO{-}NH{-}OR^2$$

| Cpd. No. | Ar | R¹ | R² | m | n | m.p. (°C.) | NMR(δ; CDCl₃) |
|---|---|---|---|---|---|---|---|
| 9-2 | 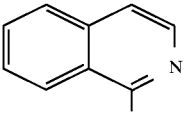 | H | EtCO | 1 | 4 | oily substance | 1.22(3H, t, J=7.5Hz), 1.32–1.46(2H, m), 1.47–1.64(2H, m), 1.65–1.80(2H, m), 1.80–1.97(2H, m), 2.28(2H, t, J=6.8Hz), 2.52 (2H, q, J=7.5Hz), 3.37(2H, t, J=7.3Hz), 7.55(1H, d, J=5.9Hz), 7.60–7.74(2H, m), 7.83(1H, d, J=7.3Hz), 8.18(1H, d, J=8.8Hz). |
| 9-3 | 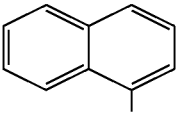 | H | PhCO | 1 | 4 | 92–93 | 1.40–1.81(6H, m), 1.97–2.10(2H, m), 2.32 (2H, t, J=7.1Hz), 4.56(1H, t, J=7.1Hz), 7.43–7.70(7H, m), 7.82–7.93(3H, m), 8.06–8.12 (2H, m), 9.16(1H, s). |
| 9-4 | 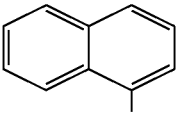 | H | EtCO | 1 | 4 | oily substance | 1.22(3H, t, J=7.5Hz), 1.35–1.50(2H, m), 1.52–1.77(4H, m), 1.97–2.11(2H, m), 2.25 (2H, t, J=7.2Hz), 2.51(2H, q, J=7.5Hz), 4.56(1H, t, J=7.1Hz), 7.45–7.72(4H, m), 7.82–7.94(3H, m), 8.85(1H, brs). |
| 9-5 | 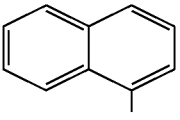 | H | Ac | 1 | 3 | oily substance | 1.62–1.81(4H, m), 2.02–2.15(2H, m), 2.20–2.36(2H, m), 2.33(3H, s), 4.56(1H, t, J=7.0Hz), 7.46–7.70(4H, m), 7.83–7.94(3H, m), 8.91(1H, brs). |

TABLE 24

$$\underset{R^1}{\overset{Ar\ (H)_m}{\diagdown}}{=}C(H)_{m+1}{-}(CH_2)_n{-}CO{-}NH{-}OR^2$$

| Cpd. No. | Ar | R¹ | R² | m | n | m.p. (°C.) | NMR(δ; CDCl₃) |
|---|---|---|---|---|---|---|---|
| 9-6 | 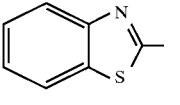 | H | Ac | 1 | 3 | 118–120 | 1.43–1.62(2H, m), 1.71–1.99(4H, m), 2.21 (3H, s), 2.29(2H, t, J=7.3Hz), 3.13(2H, t, J=7.5Hz), 7.30–7.50(2H, m), 7.81–7.87(1H, m), 7.93–7.98(1H, m). |
| 9-7 | 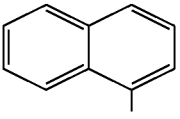 | H | EtCO | 1 | 3 | oily substance | 1.23(3H, t, J=7.5Hz), 1.58–1.83(4H, m), 2.00–2.10(2H, m), 2.21–2.29(2H, m), 2.50 (2H, q, J=7.5Hz), 4.55(1H, t, J=7.1Hz), 7.44–7.69(4H, m), 7.81–7.93(3H, m), 9.16 (1H, brs). |
| 9-8 | 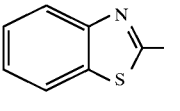 | H | EtCO | 1 | 3 | 97.5–98.0 | 1.21(3H, t, J=7.5Hz), 1.43–1.60(2H, m), 1.73–1.97(4H, m), 2.29(2H, t, J=7.4Hz), 2.49(2H, q, J=7.5Hz), 3.13(2H, t, J=7.5Hz), 7.30–7.49(2H, m), 7.82–7.86(1H, m), 7.96(1H, d, J=8.0Hz), 9.05(1H, brs). |
| 9-9 | 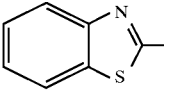 | H | PhCO | 1 | 3 | 120–121 | 1.52–1.64(2H, m), 1.76–2.01(4H, m), 2.37 (2H, t, J=7.3Hz), 3.15(2H, t, J=7.7Hz), 7.30–7.52(4H, m), 7.64(1H, t, J=7.5Hz), 7.81–7.86(1H, m), 7.94–7.98(1H, m), 8.08(2H, d, J=7.6Hz), 9.23(1H, brs). |
| 9-10 | 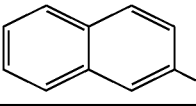 | CN | Ac | 1 | 4 | oily substance | 1.36–1.78(6H, m), 1.91–2.03(2H, m), 2.22 (3H, s), 3.96(1H, t, J=7.1Hz), 7.39(1H, dd, J=8.4, 1.8Hz), 7.49–7.55(2H, m), 7.80–7.89 (4H, m), 8.87(1H, brs). |

TABLE 25

$$\underset{R^1}{\overset{Ar\ (H)_m}{\diagdown}}C=C(H)_{m+1}-(CH_2)_n-CO-NH-OR^2$$

| Cpd. No. | Ar | R¹ | R² | m | n | m.p. (°C.) | NMR(δ; CDCl₃) |
|---|---|---|---|---|---|---|---|
| 9-11 | 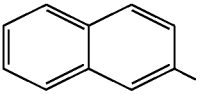 | CN | EtCO | 1 | 4 | oily substance | 1.22(3H, t, J=7.6Hz), 1.36–1.77(6H, m), 1.93–2.04(2H, m), 2.34(2H, t, J=7.3Hz), 2.50(2H, t, J=7.6Hz), 3.96(1H, t, J=7.3Hz), 7.39(1H, dd, J=8.4, 2.0Hz), 7.48–7.54(2H, m), 7.80–7.88(4H, m), 8.90(1H, brs). |
| 9-12 | 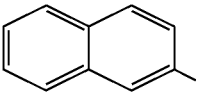 | CN | PhCO | 1 | 4 | 102–104 | 1.40–1.61(4H, m), 1.66–1.81(2H, m), 1.94–2.07(2H, m), 2.32(2H, t, J=7.2Hz), 3.97(1H, t, J=7.1Hz), 7.38–7.54(5H, m), 7.64(1H, t, J=7.6Hz), 7.81–7.89(4H, m), 8.10(2H, d, J=8.0Hz), 9.02(1H, brs). |
| 9-13 | 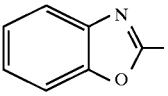 | H | PhCO | 1 | 3 | 100–102 | 1.50–1.66(2H, m), 1.73–2.02(4H, m), 2.39(2H, t, J=7.1Hz), 2.97(2H, t, J=7.3Hz), 7.25–7.32(2H, m), 7.43–7.52(3H, m), 7.58–7.67(2H, m), 8.05–8.10(2H, m), 9.37(1H, brs). |
| 9-14 | 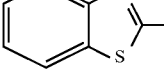 | H | PhCO | 1 | 4 | 112–113 | 1.39–1.63(4H, m), 1.65–1.98(4H, m), 2.33(2H, t, J=7.1Hz), 3.17(2H, t, J=7.3Hz), 7.31–7.52(4H, m), 7.63(1H, t, J=7.3Hz), 7.84(1H, dd, J=7.3, 1.2Hz), 7.99(1H, d, J=7.3Hz), 8.11(2H, d, J=7.4Hz), 9.96(1H, brd). |
| 9-15 | 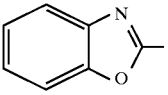 | H | EtCO | 1 | 3 | 74–75 | 1.19(3H, t, J=7.5Hz), 1.45–1.99(6H, m), 2.31(2H, t, J=7.1Hz), 2.49(2H, q, J=7.5Hz), 2.96(2H, t, J=7.3Hz), 7.27–7.34(2H, m), 7.46–7.51(1H, m), 7.63–7,68(1H, m), 9.18(1H, br). |

TABLE 26

$$\underset{R^1}{\overset{Ar\ (H)_m}{\diagdown}}C=C(H)_{m+1}-(CH_2)_n-CO-NH-OR^2$$

| Cpd. No. | Ar | R¹ | R² | m | n | m.p. (°C.) | NMR(δ; CDCl₃) |
|---|---|---|---|---|---|---|---|
| 9-16 | 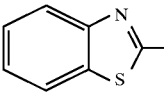 | H | 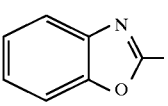 | 1 | 4 | 97–98 | 1.41–1.57(4H, m), 1.67–1.96(4H, m), 2.31(2H, t, J=7.2Hz), 2.36(3H, s), 3.16(2H, 7.6Hz), 7.16(1H, dd, J=8.0, 1.1Hz), 7.31–7.51(3H, m), 7.64(1H, td, J=8.0, 1.7Hz), 7.83–7.87(1H, m), 7.98–8.02(1H, m), 8.12(1H, dd, J=7.9, 1.7Hz), 9.68(1H, brs). |
| 9-17 | 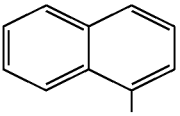 | H | 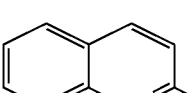 | 1 | 3 | 102–105 | 1.47–2.02(6H, m), 2.35(3H, s), 2.35(2H, t, J=7.3Hz), 2.96(2H, t, J=7.4Hz), 7.16(1H, dd, J=8.1, 1.1Hz), 7.28–7.40(3H, m), 7.46–7.52(1H, m), 7.60–7.69(2H, m), 8.19(1H, dd, J=7.9, 1.7Hz), 9.42(1H, br). |
| 9-18 |  | CO₂Et | EtCO | 1 | 4 | oily substance | 1.15(3H, t, J=7.1Hz), 1.22(3H, t, J=7.7Hz), 1.25–1.47(4H, m), 1.54–1.79(2H, m), 1.81–2.00(1H, m), 2.07–2.30(1H, m), 2.20(2H, t, J=7.3Hz), 2.50(2H, q, J=7.7Hz), 4.02(2H, m), 4.35(1H, dd, J=8.6, 6.4Hz), 7.40–7.58(4H, m), 7.76(1H, brd, J=7.8Hz), |
| 9-19 |  | H | MeCO | 1 | 4 | 107–110 | 1.20–1.90(8H, m), 2.23(3H, s), 2.26(2H, t, J=7Hz), 3.02(2H, t, J=7Hz), 7.31(1H, d, J=8Hz), 7.50(1H, m), 7.71(1H, m). 7.80(1H, d, J=8Hz), 8.10(2H, d, J=8Hz) |

TABLE 26-continued $$\underset{R^1}{\overset{Ar\ (H)_m}{>}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR(δ; CDCl₃) |
|---|---|---|---|---|---|---|---|
| 9-20 | 2-quinolinyl | H | EtCO | 1 | 4 | 97–99 | 1.22(3H, t, J=7Hz), 1.25–1.60(4H, m), 1.60 1.90(4H, m), 2.26(2H, t, J=7Hz), 2.53(2H, q, J=7Hz), 3.02(2H, t, J=7Hz), 7.32(1H, d, J=8Hz), 7.51(1H, m), 7.71(1H, m), 7.80 (1H, d, J=8Hz), 8.11(2H, d, J=9Hz), |

TABLE 27

$$\underset{R^1}{\overset{Ar\ (H)_m}{>}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR(δ; CDCl₃) |
|---|---|---|---|---|---|---|---|
| 9-21 | 2-quinolinyl | H | n-pentyl-CO | 1 | 4 | 94–95 | 0.87(3H, t, J=7Hz), 1.20–1.60(8H, m), 1.60–1.90(8H, m), 2.26(2H, t, J=7Hz), 2.48(2H, t, J=7Hz), 3.02(2H, t, J=7Hz), 7.32(1H, d, J=8Hz), 7.51(1H, m), 7.71(1H, m), 7.80(1H, d, J=8Hz), 8.11(2H, d, J=8Hz), |
| 9-22 | 2-quinolinyl | H | PhCO | 1 | 4 | 65–70 | 1.30–1.95(8H, m), 2.35(2H, t, J=7Hz), 3.05(2H, t, J=7Hz), 7.33(1H, t, J=8Hz), 7.40–7.85(6H, m), 8.00–8.20(4H, m), |
| 9-23 | 2-quinolinyl | H | 4-F-C₆H₄-CO | 1 | 4 | 104–106 | 1.30–1.95(8H, m), 2.34(2H, t, J=7Hz), 3.06(2H, t, J=7Hz), 7.15(2H, m), 7.33(1H, d, J=8Hz), 7.51(1H, m), 7.72(1H, m), 7.80 (1H, d, J=8Hz), 8.07–8.20(4H, m), |
| 9-24 | 2-quinolinyl | H | 4-(iBu)-C₆H₄-CH(Me)-CO | 1 | 4 | oily substance | 0.89(6H, d, J=7Hz), 1.10–2.30(11H, m), 1.58(3H, d, J=7Hz), 1.96(3H, s), 1.99(3H, s), 2.04(3H, s), 2.04(2H, d, J=7Hz), 3.90 (1H, q, J=7Hz), 4.28(1H, t, J=8Hz), 7.05–7.30(9H, m), 8.67(1H, br) |
| 10 | 1-NO₂-isoquinolin-2-yl | H | n-pentyl-CO | 1 | 4 | 59–60 | 0.90(3H, t, J=7Hz), 1.20–1.50(8H, m), 1.55–1.85(6H, m), 2.25(2H, t, J=7Hz), 2.48(2H, t, J=7Hz), 2.74(2H, t, J=7Hz), 7.39(1H, d, J=9Hz), 7.50–7.75(3H, m), 7.85–7.95(2H, m), 8.77(1H, s). |
| 11-1 | 2,3-dimethyl-1,4-naphthoquinonyl | Me | COEt | 1 | 2 | oily substance | 1.20(3H, t, J=7.6Hz), 1.64–1.88(2H, m), 2.19(3H, s), 2.23–2.39(4H, m), 2.49(2H, q, J=7.6Hz), 4.54(1H, t, J=7.8Hz), 7.15–7.36(5H, m), 7.65–7.73(2H, m), 8.00–8.09(2H, m), 8.89(1H, br., NH) |

TABLE 28

$$\underset{R^1}{\overset{Ar\ (H)_m}{>}}C(H)_{m+1}-(CH_2)_n-CO-NH-OR^2$$

| Cpd. No. | Ar | R¹ | R² | m | n | m.p. (°C.) | NMR(δ; CDCl₃) |
|---|---|---|---|---|---|---|---|
| 11-2 | 2-methyl-1,4-naphthoquinone | Me | COMe | 1 | 3 | oily substance | 1.20–1.54(2H, m), 1.60–1.84(2H, m), 2.09–2.34(10H, m), 4.47(1H, t, J=7.6Hz), 7.13–7.35(5H, m), 7.62–7.69(2H, m), 7.95–8.07(2H, m), 9.22(1H, br., NH) |
| 11-3 | 2-methyl-1,4-naphthoquinone | Me | COEt | 1 | 3 | oily substance | 1.14(3H, t, J=7.4Hz), 1.28–1.56(2H, m), 1.60–1.84(2H, m), 2.18–2.34(7H, m), 2.43(2H, q, J=7.4Hz), 4.47(1H, t, J=7.9Hz), 7.12–7.36(5H, m), 7.61–7.68(2H, m), 7.96–8.06(2H, m), 9.20(1H, br., NH) |
| 11-4 | 2-methyl-1,4-naphthoquinone | Me | COPh | 1 | 3 | oily substance | 1.30–1.66(2H, m), 1.68–1.96(2H, m), 2.20–2.37(7H, m), 4.48(1H, t, J=7.8Hz), 7.17–7.65(10H, m), 7.96–8.13(4H, m), 9.45(1H, br., NH) |
| 11-5 | trimethyl-1,4-benzoquinone | Me | COMe | 1 | 3 | oily substance | 1.20–1.40(2H, m), 1.64–1.82(2H, m), 1.95(3H, s), 1.99(3H, s), 2.07(3H, s), 2.12–2.28(7H, m), 4.22(1H, t, J=7.9Hz), 6.96(2H, dd, J=5.4Hz, 8.6Hz), 7.24(2H, dd, J=5.4Hz, 8.6Hz), 9.00(1H, br., NH) |
| 11-6 | trimethyl-1,4-benzoquinone | Me | COEt | 1 | 3 | oily substance | 1.20(3H, t, J=7.6Hz), 1.24–1.39(2H, m), 1.64–1.80(2H, m), 1.95(3H, s), 1.99(3H, s), 2.07(3H, s), 2.12–2.28(4H, m), 2.49(2H, q, J=7.6Hz), 4.22(1H, t, J=7.7Hz), 6.95(2H, dd, J=5.4Hz, 8.8Hz), 7.24(2H, dd, J=5.4Hz, 8.8Hz), 9.15(1H, br., NH) |

TABLE 29

$$\underset{R^1}{\overset{Ar\ (H)_m}{>}}C(H)_{m+1}-(CH_2)_n-CO-NH-OR^2$$

| Cpd. No. | Ar | R¹ | R² | m | n | m.p. (°C.) | NMR(δ; CDCl₃) |
|---|---|---|---|---|---|---|---|
| 11-7 | 2-methyl-1,4-naphthoquinone | Me | CO(CH₂)₄CH₃ | 1 | 3 | oily substance | 0.89(3H, t, J=6.2Hz), 1.22–1.46(6H, m), 1.56–1.77(4H, m), 2.17–2.35(7H, m), 2.42(2H, t, J=7.5Hz), 3.77(3H, s), 4.39(1H, t, J=7.8Hz), 6.83(2H, d, J=8.8Hz), 7.22–7.29(2H, m), 7.64–7.71(2H, m), 7.97–8.09(2H, m), 8.78(1H, br., NH) |

TABLE 29-continued $$\underset{R^1}{\overset{Ar\ (H)_m}{>}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR(δ; CDCl₃) |
|---|---|---|---|---|---|---|---|
| 11-8 | 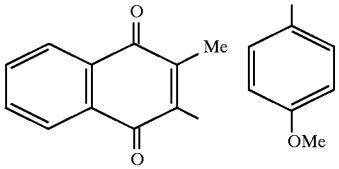 | Me | COcyclohexyl 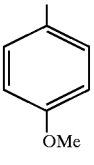 | 1 | 3 | non-crystal powder | 1.21–2.06(14H, m), 2.19–2.50(8H, m), 3.77 (3H, s), 4.39(1H, t, J=7.7Hz), 6.83(2H, d, J=8.6Hz), 7.23–7.30(2H, m), 7.64–7.74(2H, m), 8.00–8.10(2H, m), 8.70(1H, br., NH) |
| 11-9 | 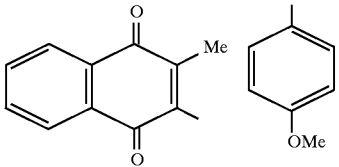 | Me | COCH(Ph)₂ 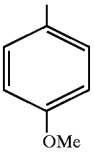 | 1 | 3 | non-crystal powder | 1.22–1.51(2H, m), 1.64–1.83(2H, m), 2.14–2.30(7H, m), 3.76(3H, s), 4.37(1H, t, J=7.7Hz), 5.18(1H, s), 6.81(2H, d, J=8.8Hz), 7.20–7.36(2H, m), 7.61–7.70(2H, m), 7.95–8.07(2H, m), 8.68(1H, br., NH) |
| 11-10 | 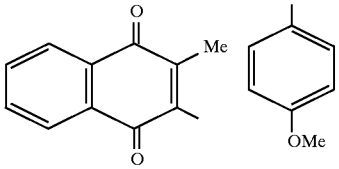 | Me | COCH₂CH(Ph)₂ 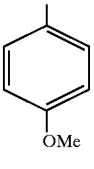 | 1 | 3 | non-crystal powder | 1.22–1.47(2H, m), 1.53–1.77(2H, m), 2.05–2.35(7H, m), 3.21(2H, d, J=8Hz), 3.77 (3H, s), 4.37(1H, t, J=8Hz), 4.55(1H, t, J=8Hz), 6.83(2H, d, J=8Hz), 7.15–7.41 (12H, m), 7.63–7.78(2H, m), 7.97–8.13(2H, m), 8.61(1H, br., NH) |
| 11-11 | 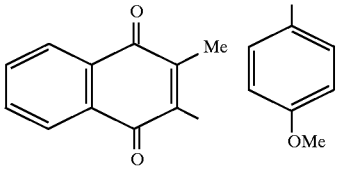 | Me | CONH₂ 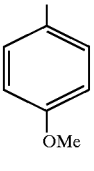 | 1 | 3 | non-crystal powder | 1.29–1.49(2H, m), 1.63–1.83(2H, m), 2.14–2.33(7H, m), 3.77(3H, s), 4.39(1H, t, J=8.1Hz), 5.17(2H, br., NH2), 6.82(2H, d, J=8.2Hz), 7.25(2H, d, J=8.2Hz), 7.63–7.71 (2H, m), 7.97–8.09(2H, m), 8.90(1H, br., NH) |

TABLE 30

$$\underset{R^1}{\overset{Ar\ (H)_m}{>}}\!\!=\!\!C(H)_{m+1}\!-\!(CH_2)_n\!-\!CO\!-\!NH\!-\!OR^2$$

| Cpd. No. | Ar | R¹ | R² | m | n | m.p. (°C.) | NMR(δ; CDCl₃) |
|---|---|---|---|---|---|---|---|
| 11-12 | 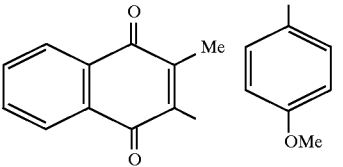 | Me | COEt 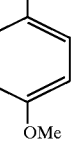 | 1 | 4 | oily substance | 1.22(3H, t, J=7.6Hz), 1.28–1.47(4H, m), 1.54–1.75(2H, m), 2.15–2.30(7H, m), 2.51 (2H, q, J=7.6Hz), 3.77(3H, s), 4.40(1H, t, J=7.6Hz), 6.83(2H, d, J=8.6Hz), 7.26(2H, d, J=8.6Hz), 7.63–7.73(2H, m), 8.00–8.08 (2H, m), 8.77(1H, br., NH) |
| 11-13 | 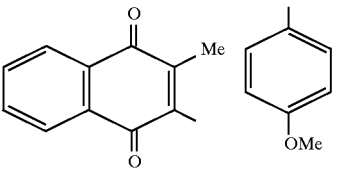 | Me | COPh 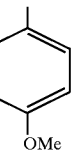 | 1 | 4 | non-crystal powder | 1.21–1.51(4H, m), 1.55–1.82(2H, m), 2.15–2.35(7H, m), 3.77(3H, s), 4.41(1H, t, J=7.7Hz), 6.82(2H, d, J=8.8Hz), 7.26(2H, d, J=8.8Hz), 7.48(2H, t, J=7.5Hz), 7.57–7.71(3H, m), 7.97–8.13(4H, m), 9.11(1H, br., NH) |

TABLE 30-continued $$\underset{R^1}{\overset{Ar\quad (H)_m}{\diagdown}}C = C(H)_{m+1} - (CH_2)_n - CO - NH - OR^2$$

| Cpd. No. | Ar | R¹ | R² | m | n | m.p. (°C.) | NMR(δ; CDCl₃) |
|---|---|---|---|---|---|---|---|
| 11-14 | 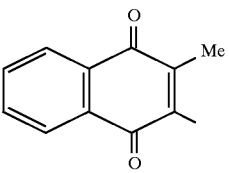 | Me | COEt | 1 | 4 | oily substance | 1.21(3H, t, J=7.4Hz), 1.32–1.51(4H, m), 1.58–1.76(2H, m), 2.16–2.34(7H, m), 2.50 (2H, q, J=7.4Hz), 4.49(1H, t, J=7.9Hz), 7.13–7.38(5H, m), 7.63–7.73(2H, m), 7.99–8.09(2H, m), 8.86(1H, br., NH) |
| 11-15 | 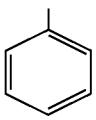 | Me | COPh | 1 | 4 | non-crystal powder | 1.23–1.52(4H, m), 1.63–1.80(2H, m), 2.17–2.35(7H, m), 4.50(1H, t, J=7.9Hz), 7.13–7.37(5H, m), 7.48(2H, t, J=7.6Hz), 7.58–7.72(3H, m), 7.98–8.13(4H, m), 9.06(1H, br., NH) |
| 11-16 | 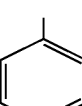 | Me | CONHEt | 1 | 4 | 138–140 | 1.17(3H, t, J=7.2Hz), 1.26–1.50(4H, m), 1.56–1.75(2H, m), 2.12–2.33(7H, m), 3.19–3.35(2H, m), 4.49(1H, t, J=7.2Hz), 5.34 (1H, br., NH), 7.14–7.36(5H, m), 7.63–7.74 (2H, m), 7.99–8.10(2H, m), 8.86(1H, br., NH) |

TABLE 31

$$\underset{R^1}{\overset{Ar\quad (H)_m}{\diagdown}}C = C(H)_{m+1} - (CH_2)_n - CO - NH - OR^2$$

| Cpd. No. | Ar | R¹ | R² | m | n | m.p. (°C.) | NMR(δ; CDCl₃) |
|---|---|---|---|---|---|---|---|
| 11-17 | 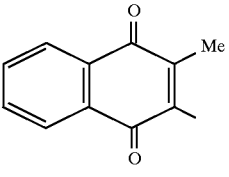 | Me | COEt | 1 | 4 | 107–110 | 1.22(3H, t, J=7.8Hz), 1.30–1.48(4H, m), 1.54–1.73(2H, m), 2.13–2.27(7H, m), 2.51 (2H, q, J=7.8Hz), 4.42(1H, t, J=7.5Hz), 6.97(2H, t, J=8.6Hz), 7.23–7.35(2H, m), 7.62–7.73(2H, m), 7.98–8.10(2H, m), 8.78 (1H, br., NH) |
| 11-18 | 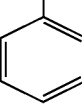 | Me | COPh | 1 | 4 | oily substance | 1.22–1.52(4H, m), 1.64–1.80(2H, m), 2.17–2.35(7H, m), 4.43(1H, t, J=7.7Hz), 6.97 (2H, t, J=8.7Hz), 7.24–7.34(2H, m), 7.48 (2H, t, J=7.6Hz), 7.59–7.73(3H, m), 7.98–8.13(4H, m), 9.04(1H, br., NH) |
| 11-19 | 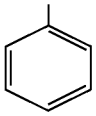 | OMe | COEt | 1 | 3 | oily substance | 1.21(3H, t, J=7.6Hz), 1.28–1.46(2H, m), 1.65–1.79(2H, m), 1.83–1.98(2H, m), 2.23 (2H, t, J=7.4Hz), 2.50(2H, q, J=7.6Hz), 3.77(3H, s), 4.25(1H, t, J=7.7Hz), 6.79 (1H, s), 6.84(2H, d, J=8.7Hz), 7.20(2H, d, J=8.7Hz), 7.66–7.76(2H, m), 8.00–8.09(2H, m), 8.85(1H, br., NH) |

TABLE 31-continued $$\text{Ar}(H)_m \underset{R^1}{\overset{}{\diagdown}}=C(H)_{m+1}-(CH_2)_n-CO-NH-OR^2$$

| Cpd. No. | Ar | R¹ | R² | m | n | m.p. (°C.) | NMR(δ; CDCl₃) |
|---|---|---|---|---|---|---|---|
| 11-20 | 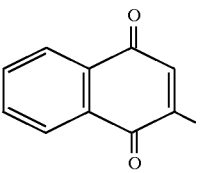 | | 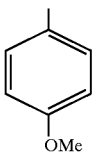COPh, OMe | 1 | 3 | oily substance | 1.33–1.49(2H, m), 1.68–1.83(2H, m), 1.83–1.98(2H, m), 2.32(2H, t, J=7.4Hz), 3.77 (3H, s), 4.27(1H, t, J=7.4Hz), 6.81(1H, s), 6.84(2H, d, J=8.5Hz), 7.21(2H, d, J=8.5Hz), 7.48(2H, t, J=7.7Hz), 7.58–7.75 (3H, m), 8.00–8.15(4H, m), 9.15(1H, br., NH) |

Formulation Example 1

A) Capsule

| | |
|---|---|
| (1) Compound 7-9 | 50 mg |
| (2) Finely divided cellulose powder | 30 mg |
| (3) Lactose | 37 mg |
| (4) Magnesium stearate | 3 mg |
| Total | 120 mg |

The above components (1), (2), (3), and (4) were mixed and filled in a gelatin capsule shell.

B) Soft capsule

| | |
|---|---|
| (1) Compound 7-10 | 50 mg |
| (2) Corn Oil | 100 mg |
| Total | 150 mg |

The above components were mixed and filled in a soft capsule shell in the conventional manner.

C) Tablet

| | |
|---|---|
| (1) Compound 7-8 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose Ca | 20 mg |
| Total | 120 mg |

The above components were mixed and compressed using a tablet machine in the conventional manner.

Formulation Example 2

| | |
|---|---|
| (1) Compound 7-6 | 10.0 g |
| (2) Lactose | 60.0 g |
| (3) Corn starch | 35.0 g |
| (4) Gelatin | 3.0 g |
| (5) Magnesium stearate | 2.0 g |

Using a 10 weight % aqueous solution of gelatin (3.0 g), a mixture of the compound obtained in Example 7 (10.0 g), lactose (60.0 g) and corn starch (35.0 g) was granulated through a 1 mm-mesh sieve, dried at 40° C., and resieved. This granulation was mixed with 2.0 g of magnesium stearate and the mixture was compressed. The core tablets thus obtained were coated with a sugar-coating composition comprising an aqueous suspension of sucrose, titanium dioxide, talc, and gum arabic. The coated tablets were glazed with beeswax to provide 1000 finished tablets.

Experimental Example 1

Neutralizing effect on lipopolysaccharide (LPS)—induced cytotoxicity in a rat mixed cerebral cell culture system (LIC assay)

LPS, a substance known to activate glial cells (astrocytes, microglia), was added to a rat mixed cerebral cell culture system and the compounds which would neutralize the cytotoxicity induced by LPS were screened by the following method.

[Method]
(1) Neonatal rat mixed cerebral cell culture

From neonatal Crj:CD (SD) rats (1–3 days old, Charles-River Japan, Ltd.), the brains were isolated and placed in ice-cold D-MEM/10% FCS (Dulbecco's cell culture minimal essential medium supplemented with 10% of fetal calf serum, 100 units/ml of penicillin and 100 μg/ml of streptomycin). Then, mixed cerebral cell cultures were carried out in the following steps.

1. The cerebrums were separated from the enucleated brains and the meninges was removed under the stereoscopic microscope.
2. The cerebrums were placed in a nylon-mesh (100–200 μm) bag to filter with the aid of a rubber policeman.
3. Using ice-cold D-MEM/10% FCS, the cells were washed 3 times (1000 rpm, 8 min.). Then, this cell suspension was filtered through a cell strainer (40 μm mesh, Falcon 2340) and the number of viable cells was counted by the trypan blue method.
4. The cells, were seeded in wells of a 96-well microtiter plate (Nunc) at a cell density of 1×10⁵ cells/100 μl/well, and started a cell culture at 37° C.
5. One week later, 100 μl/well of D-MEM/10% FCS was added.
6. The plate was further incubated for about 1–2 weeks and the neutralizing activity of the test compound was evaluated by the following method.

(2) Evaluation of neutralizing activity in LPS-induced cytotoxicity

1. Following the rat mixed cerebral cell culture described in (1) (after 2–3 weeks of incubation), the medium was discarded from the respective wells of the 96-well microtiter plate, and 50 μl/well of fresh D-MEM/2% FCS was added.

2. A test sample and LPS (Difco, *E. coli* 011: B4, Bacto) of a suitable concentration, 25 μl each per well, were respectively added. D-MEM/2% FCS was used as the medium.

As the test sample, each of the compounds shown in Table 32 was dissolved in DMSO at a concentration of $10^{-2}$M and the solution was diluted with D-MEM/2% FCS and submitted for assay.

3. After a suitable period (usually 4–5 days) of incubation, the degree of cytotoxic effect was assessed by the microscopic observation, and MTT method.

(3) MTT [3-(4,5-dimethylthiazol-2-yl)-2,5-diphenyltetrazolium bromide] method

Ten μl of MTT solution (5 mg/ml, Sigma) dissolved in phosphate-buffered saline was added to each well. After 4–6 hours of incubation (37° C., under 10% $CO_2$), 100 μl/well of 0.01N-hydrochloric acid containing 10% SDS was added, whereby the formed formazan was dissolved. After complete dissolution, the absorbance (540–590 nm) was measured for each well.

The $ED_{50}$ values were determined by calculating the recovery rates by means of the following equation and plotting the concentrations of compounds giving a recovery rate of 50% on graph paper.

Recovery rate (%)=(C−B)×100/(A−B)

[A: the absorbance at 550 nm of the control well to which only the medium had been added B: the absorbance at 550 nm of the well to which LPS had been added C: the absorbance at 550 nm of the well to which both LPS and the test compound had been added]

[Results]

The results are presented below in Table 32.

TABLE 32

| Compound No. | $ED_{50}$ (μM) |
|---|---|
| Compound A | 0.02 |
| Compound B | 0.5 |
| Compound C | 0.3 |
| Compound D | 0.1 |
| Compound E | 0.6 |
| Reference Example 46-1 | 0.05 |
| Reference Example 46-2 | 0.5 |
| Compound 1-3 | 0.02 |
| Compound 1-4 | 0.04 |
| Compound 7-1 | 0.05 |
| Compound 7-2 | 0.05 |
| Compound 7-3 | 0.4 |
| Compound 7-4 | 0.4 |
| Compound 7-5 | 0.05 |
| Compound 7-6 | 0.05 |
| Compound 7-7 | 0.5 |
| Compound 7-8 | 0.03 |
| Compound 7-9 | 0.2 |
| Compound 7-10 | 0.3 |
| Compound 7-11 | 0.2 |
| Compound 7-12 | 0.03 |
| Compound 7-13 | 0.05 |
| Compound 7-14 | 0.2 |
| Compound 7-15 | 0.5 |
| Compound 7-16 | 0.3 |
| Compound 7-17 | 0.2 |
| Compound 3-2 | 0.03 |

Compound A: 6-(3-Methyl-1,4-naphthoquinon-2-yl)-6-(4-methoxyphenyl)hexanohydroxamic acid
Compound B: 6-(4-Fluorophenyl)-6-(3-methyl-1,4-naphtho-quinon-2-yl)hexanohydroxamic acid
Compound C: 7-(3,5,6-Trimethyl-1,4-benzoquinon-2-yl)-7-phenylheptanohydroxamic acid
Compound D: 7-(3,5,6-Trimethyl-1,4-benzoquinon-2-yl)-7-(4-methylphenyl)heptanohydroxamic acid
Compound E: 7-(4-Fluorophenyl)-7-(3,5,6-trimethyl-1,4-benzoquinon-2-yl)heptanohydroxamic acid It is apparent from the above data that the Compounds (I) and (II) of the present invention neutralized the LPS-induced cytotoxicity and death of nerve cells at low concentrations, attesting to their remarkably high anti-neurodegeneration activity.

Experimental Example 2

[Method]

Rat mixed cerebral cell cultures on day 15 after starting cell cultures were used. After removal of the medium, LPS (*E. coli* 011: B4, Bacto) (Difco Laboratories), 10 μg/ml, and Compound A, $10^{-6}$ or $10^{-7}$M, were simultaneously added and the final volume was adjusted to 100 μl. After 24 hours of incubation at 37° C., the culture supernatant was collected as a sample for ELISA. The assay for determining TNFα amount was made using Mouse TNFα ELISA Kit (Genzyme) in accordance with its assay protocol.

[Results]

The effect of Compound A on LPS-induced TNFO production in the rat mixed cerebral cell culture system is shown below in Table 33.

TABLE 33

| LPS (μg/ml) | Compound A (M) | TNFα (pg/ml) |
|---|---|---|
| 0 | 0 | 48 |
| 10 | 0 | 1500 |
| 10 | $10^{-7}$ | 790 |
| 10 | $10^{-6}$ | 230 |

Experimental Example 3

Inhibitory effect on the apomorphine-induced circling in rats pretreated with LPS infused into the unilateral striatum

[Method]

Male Wistar rats (8–9 weeks old) weighing 250–280 g at the operation for LPS infusion were submitted to the experiment. Throughout the experimental period, the animals were group-fed in a vivarium controlled at 24±1° C. and 55±1% R.H., with a light-dark cycle of 12 hr (7:00–19:00 ON) and free access to food (Clea Japan, Inc., CE-2 pellets) and water (tap water).

Under pentobarbital (50 mg/kg, i.p.) anesthesia, the rat's head was immobilized in David Kopf's brain stereotaxic apparatus for small animal use and with reference to Pellegrino & Cushman's brain atlas, a 30 G stainless steel needle was indwelled in the unilateral striate body (A8.2, L2.8, H4.3). The infusion amount of LPS was set at 5 μg. LPS was dissolved in 1 μl of phosphate-buffered saline (PBS, pH 7.2) and the solution was infused gradually at a speed of 0.2 μl/min. The infusion needle was kept in position till 3 minutes following infusion and withdrawn only after sufficient diffusion of the drug solution had taken place.

After 7–8 days postoperatively, 1 mg/kg of apomorphine was administered subcutaneously and the number of induced circling behavior during a 30-minute period immediately following administration were determined with an automatic counter.

Compound A was suspended in 5% aqueous gum arabic solution and the suspension was administered either orally or intraperitoneally at a dose rate of 0.2 ml per 100 g rat body weight. This administration was carried out 3 times, namely 30 minutes before infusion of 5 μg LPS and 3 and 24 hours after the infusion. As a control, physiological saline solution alone was administered intraperitoneally.

[Results]

Table 34 shows the effect of administration of Compound A on the apomorphine-induced circling behavior in rats given an infusion of LPS (5 μg) into the unilateral striatum.

TABLE 34

| Experimental group | Number of ipsilateral circlings (mean ± S.E.) |
|---|---|
| Physiological saline | 114 ± 29 |
| Compound A p.o. (30 mg/kg) | 65 ± 21 |
| Compound A i.p. (3 mg/kg) | 44 ± 15 |

(Each group consisted of 4 animals)

It is apparent from the above data that Compound A significantly attenuated LPS-induced injury of the unilateral striatum, attesting to its remarkably high anti-neurodegenerative activity.

Experimental Example 4

Inhibitory effect on LSP-induced NO (nitric oxide) production in a rat mixed cerebral cell culture system

[Method]

(1) Rat mixed cerebral cell culture

Rat mixed cerebral cell cultures were prepared by the procedure described in Experimental Example 1.

(2) NO production

1. Twenty (20) days after initiation of rat mixed cerebral cell culture, the medium was removed from each well of the 96-well microtiter plate and, instead, 125 μl/well of D-MEM/2% FCS containing 5 μg/ml (final concentration) of LSP (Difco, *E. coli* 011: B4, Bacto) and a suitable dilution of the test compound was added. As the test sample, a stock DMSO solution of $10^{-2}$M concentration was prepared and diluted with D-MEM/2% FCS.

2. After a further 5 days of cell culture, the combined amount of $NO_3^-$ and $NO_2^-$ in the culture supernatant was determined with the $NO_3^-NO_2^-$ Assay Kit (Cayman Chemical, Catalog No. 780001, U.S.A.). The assays were carried out in accordance with the accompanying protocol.

(3) Calculation of $IC_{50}$

The $IC_{50}$ values were determined from a plot of the concentrations of the test compound which caused a 50% decrease in the combined amount of $N_2^-$ and $NO_3^-$ in the culture supernatant as compared with the well to which LSP alone had been added in a final concentration of 5 μg/ml without addition of compound A.

[Results]

The inhibition concentration ($IC_{50}$) of compound A against LSP-induced NO production in a mixed rat cerebral cell culture system was 0.08 μM.

It is, therefore, apparent that the compound of the present invention strongly inhibits NO (nitric oxide) production.

Industrial Applicability

The compound (I) of the present invention and the compound (II) have excellent anti-neurodegenerative activity with a low toxic potential and, therefore, are useful for the prophylaxis, therapy or improved prognosis of neurodegenerative diseases such as Alzheimer's disease, Parkinson's disease, Down's syndrome, Pick's disease, multiple sclerosis, bacterial or viral meningitis such as Borna disease, postvaccination encephalitis, AIDS-associated encephalopathy, etc., and brain dysfunctions such as cerebral infarction, cerebral hemorrhage, subarachinoid hemorrhage, trauma, etc. These compounds are also effective in cytokine-associated general malaise, fever, sleep, headache, arthralgia, anorexia, depression, and other symptoms. Furthermore, compounds (I) and (II) inclusive of their salts inhibit abnormal release of nitric oxide typically due to activation of the immune system and are, therefore, effective for palliation of septic shock, nephritis, atherosclerosis, asthma, diabetes, and bone diseases, among other morbidities.

We claim:

1. A compound of the formula:

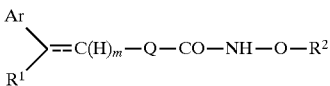

wherein

Ar represents i) a $C_{6-14}$aryl, ii) a 5- to 11-membered heteroaromatic group containing, besides carbon atoms, 1 to 4 hetero atoms selected from the group consisting of nitrogen, oxygen and sulfur, or iii) a quinone group, wherein Ar may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, hydroxyl, amino, mono-$C_{1-6}$alkylamino, di-$C_{1-6}$alkylamino, $C_{1-6}$alkylcarbonyl, carboxyl, $C_{1-6}$alkoxycarbonyl, carbamoyl, mono-$C_{1-6}$alkylcarbamoyl, di-$C_{1-6}$alkylcarbamoyl, $C_{6-10}$arylcarbamoyl, sulfo, $C_{1-6}$alkylsulfonyl, $C_{6-10}$aryl, $C_{6-10}$aryloxy, optionally halogenated $C_{1-6}$alkylsulfonylamino and optionally substituted $C_{6-10}$arylsulfonylamino;

Q represents a divalent $C_{2-8}$aliphatic hydrocarbon group;

$R^1$ represents i) hydrogen, ii) a cyano group, iii) a $C_{1-6}$alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group, iv) a group of the formula:

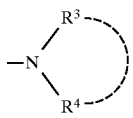

wherein $R^3$ and $R^4$ are independently a) hydrogen, b) an acyl group represented by the formula: —CO—R, —SO$_2$—R, —SO—R, —CONH—R, —CO—O—R, —CS—NH—R or —CS—O—R wherein R is (1) hydrogen, (2) a $C_{1-6}$alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group or (3) 5- to 10-membered heterocyclic group containing, besides carbon atoms, 1 to 3 hetero atoms selected from the group consisting of nitrogen, oxygen and sulfur, which heterocyclic group may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$ cycloalkyl, optionally halogenated $C_{1-6}$alkoxy, optionally halogenated $C_{1-6}$alkylthio, amino, mono-$C_{1-6}$ alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group, or c) a $C_{1-6}$alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{13}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group, or $R^3$ and $R^4$, taken together with the adjacent nitrogen atom, form a 5- to 7-membered nitrogen-containing ring having, besides carbon atoms and one nitrogen atom, 1 to 3 hetero atoms selected from the group consisting of nitrogen, oxygen and sulfur, or v) an acyl group represented by the formula: —CO—R, —SO$_2$—R, —SO—R, —CONH—R, —CO—O—R, —CS—NH—R or —CS—O—R wherein R is (1) hydrogen, (2) a $C_{1-6}$alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group or (3) 5-to 10-membered heterocyclic group containing, besides carbon atoms, 1 to 3 hetero atoms selected from the group consisting of nitrogen, oxygen and sulfur, which heterocyclic group may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group;

$R^2$ represents an acyl group represented by the formula: —CO—R, —SO$_2$—R, —SO—R, —CONH—R, —CO—O—R, —CS—NH—R or —CS—O—R wherein R is i) hydrogen, ii) a $C_{1-6}$alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$ alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group or iii) a 5- to 10-membered heterocyclic group containing, besides carbon atoms, 1 to 3 hetero atoms selected from the group consisting of nitrogen, oxygen and sulfur, which heterocyclic group may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group;

......... represents a single bond or a double bond; and m represents 1 or 2, or a salt thereof.

2. A compound of claim 1 wherein $R^1$ is i) hydrogen, ii) a cyano group, iii) $C_{1-6}$ alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$ alkylamino, di-$C_{1-6}$alkylamino, hydroxyl, $C_{1-6}$ alkylcarbonyl, carboxyl, $C_{1-6}$alkoxycarbonyl, $C_{1-6}$ alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group, or iv) a group of the formula:

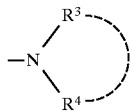

3. A compound of claim 1 wherein Ar is a i) p-benzoquinon-2-yl, ii) 1,4-naphthoquinon-2-yl, iii) anthraquinonyl, iv) 5,6-chrysenequinonyl or v) 5,8-dioxo-5,8-dihydroquinolin-6-yl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, hydroxyl, amino, mono-$C_{1-6}$alkylamino, di-$C_{1-6}$alkylamino, $C_{1-6}$alkylcarbonyl, carboxyl, $C_{1-6}$alkoxycarbonyl, carbamoyl, mono-$C_{1-6}$alkylcarbamoyl, di-$C_{1-6}$alkylcarbamoyl, $C_{6-10}$arylcarbamoyl, sulfo, $C_{1-6}$alkylsulfonyl, $C_{6-10}$aryl, $C_{6-10}$aryloxy, optionally halogenated $C_{1-6}$alkylsulfonylamino and optionally substituted $C_{6-10}$-arylsulfonylamino, $R^1$ is a phenyl or naphthyl group which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group, and $R^2$ is an acyl group of the formula: —CO—R or —CO—NH—R.

4. A compound of claim 1 wherein $R^1$ is a cyano group and $R^2$ is an acyl group of the formula: —CO—R or —CO—NH—R.

5. A compound of claim 1 wherein Ar is a phenyl, 1-naphthyl, 2-naphthyl, 2-quinolyl, 3-quinolyl, 4-quinolyl, 1-isoquinolyl, 4-isoquinolyl, 2-benzothiazolyl, 2-benzoxazolyl, 2-benzimidazolyl, 2-pyridothiazolyl, p-benzoquinon-2-yl, 1,4-naphthoquinon-2-yl or 5,8-dioxo-5,8-dihydroquinolin-6-yl group, each of which may be substituted by 1 to 4 substituents selected from the group consisting of i) a halogen, ii) a nitro, iii) an optionally halogenated $C_{1-6}$alkyl, iv) an optionally halogenated $C_{1-6}$alkoxy, v) a hydroxyl, vi) an amino, vii) a mono-$C_{1-6}$alkylamino, viii) a di-$C_{1-6}$alkylamino, ix) an optionally halogenated $C_{1-6}$alkylsulfonylamino and x) a $C_{6-10}$arylsulfonylamino optionally substituted by 1 to 3 halogen atoms or optionally halogenated $C_{1-6}$alkyl groups, Q is a divalent $C_{2-5}$alkylene, $R^1$ is i) hydrogen, ii) a cyano group, iii) a phenyl group which may be substituted by 1 to 3 substituents selected from the group consisting of halogen, optionally halogenated $C_{1-6}$alkyl and optionally halogenated $C_{1-6}$alkoxy, iv) a group of the formula:

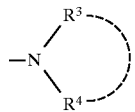

wherein $R^3$ is hydrogen and $R^4$ is an acyl group of the formula: —CO—R' or —SO$_2$—R' wherein R' is a $C_{1-6}$alkyl or $C_{6-14}$ aryl group which may be substituted by 1 to 3 substituents selected from the group consisting of a halogen and $C_{1-6}$alkyl, or v) an acyl group of the formula: —CO—O—R" wherein R" is a $C_{1-6}$alkyl group, $R^2$ is an acyl group of the formula: —CO—R''' or —CONH—R''' wherein R''' is i) hydrogen or ii) a $C_{1-6}$alkyl, $C_{3-6}$cycloalkyl or $C_{6-14}$aryl group which may be substituted by 1 to 3 substituents selected from the group consisting of a) a halogen, b) an optionally halogenated $C_{1-6}$alkyl, c) an optionally halogenated $C_{1-6}$alkoxy, d) a $C_{1-6}$alkylcarbonyloxy and e) a $C_{6-14}$aryl optionally substituted by 1 to 3 substituents selected from the group consisting of a $C_{1-6}$alkyl and $C_{1-6}$alkoxy, ......... is a single bond, and m is 2.

6. A compound of claim 5 wherein Ar is a p-benzoquinon-2-yl or 1,4-naphthoquinon-2-yl group which may be substituted by 1 to 4 substituents selected from the group consisting of i) a halogen, ii) an optionally halogenated $C_{1-6}$alkyl and iii) an optionally halogenated $C_{1-6}$alkoxy, $R^1$ is a phenyl group which may be substituted by 1 to 3 substituents selected from the group consisting of a halogen, optionally halogenated $C_{1-6}$alkyl and optionally halogenated $C_{1-6}$alkoxy, and $R^2$ is an acyl group of the formula: —CO—R'''' wherein R'''' is a $C_{1-6}$alkyl, $C_{3-6}$cycloalkyl or phenyl group which may be substituted by 1 to 3 halogens.

7. A compound of claim 1 wherein Q is trimethylene or tetramethylene.

8. A compound of claim 1 which is
O-acetyl-6-(4-methoxyphenyl)-6-(3-methyl-1,4-naphthoquinon-2-yl)hexanohydroxamic acid,
O-propionyl-6-(4-methoxyphenyl)-6-(3-methyl-1,4-naphthoquinon-2-yl)hexanohydroxamic acid,
O-isobutyryl-6-(4-methoxyphenyl)-6-(3-methyl-1,4-naphthoquinon-2-yl)hexanohydroxamic acid,
O-benzoyl-6-(4-methoxyphenyl)-6-(3-methyl-1,4-naphthoquinon-2-yl)hexanohydroxamic acid,
O-propionyl-7-(4-methoxyphenyl)-7-(3-methyl-1,4-naphthoquinon-2-yl)heptanohydroxamic acid,
O-propionyl-7-(4-fluorophenyl)-7-(3-methyl-1,4-naphthoquinon-2-yl)heptanohydroxamic acid, or a salt thereof.

9. A process for producing the compound of claim 1, which comprises reacting a compound of the formula:

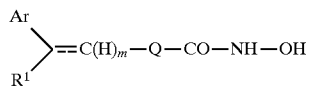

or a salt thereof, with a compound of the formula:

wherein Y represents a leaving group, or a salt thereof.

10. An anti-neurodegenerative composition which comprises a compound of the formula:

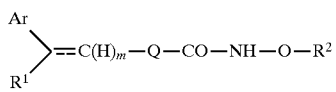

according to claim 1, wherein
  $R^2$ represents 1) hydrogen or 2) an acyl group represented by the formula: —CO—R, —SO$_2$—R, —SO—R, —CONH—R, —CO—O—R, —CS—NH—R or —CS—O—R wherein R is i) hydrogen, ii) a $C_{1-6}$alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group or iii) a 5- to 10-membered heterocyclic group containing, besides carbon atoms, 1 to 3 hetero atoms selected from the group consisting of nitrogen, oxygen and sulfur, which heterocyclic group may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group;
  or a salt thereof, with a pharmaceutically acceptable carrier.

11. An anti-neurodegenerative composition which comprises a compound of claim 1, or a salt thereof, with a pharmaceutically acceptable carrier.

12. A composition of claim 10 which comprises
  O-propionyl-6-(4-methoxyphenyl)-6-(3-methyl-1,4-naphthoquinon-2-yl)hexanohydroxamic acid,
  O-propionyl-7-(4-methoxyphenyl)-7-(3-methyl-1,4-naphthoquinon-2-yl)heptanohydroxamic acid,
  7-(4-methoxyphenyl)-7-(3-methyl-1,4-naphthoquinon-2-yl)heptanohydroxamic acid, 6-(4-methoxyphenyl)-6-(3-methyl-1,4-naphthoquinon-2-yl)hexanohydroxamic acid, or a salt thereof.

13. A composition of claim 10 which is for treating neurodegenerative diseases.

14. A composition of claim 13 which is for treating Alzheimer's disease or multiple sclerosis.

15. A pharmaceutical composition which comprises a compound of claim 1 with a pharmaceutically acceptable carrier.

16. Method for treating neurodegenerative diseases in mammals which comprises administrating to a subject in need a therapeutically effective amount of a compound of the formula:

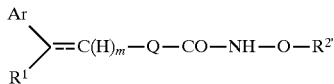

according to claim 1, wherein
  $R^{2'}$ represents 1) hydrogen or 2) an acyl group represented by the formula: —CO—R, —SO$_2$—R, —SO—R, —CONH—R, —CO—O—R, —CS—NH—R or —CS—O—R wherein R is i) hydrogen, ii) a $C_{1-6}$alkyl, $C_{2-6}$alkenyl, $C_{2-6}$alkynyl, $C_{3-6}$cycloalkyl or $C_{6-14}$aryl group, each of which may be substituted by 1 to 5 substituents selected from the group consisting of a halogen, $C_{1-3}$alkylenedioxy, nitro, cyano, optionally halogenated $C_{1-6}$alkyl, optionally halogenated $C_{1-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_{6-10}$aryloxy and 5- or 6-membered heterocyclic group or iii) a 5- to 10-membered heterocyclic group containing, besides carbon atoms, 1 to 3 hetero atoms selected from the group consisting nitrogen, oxygen and sulfur, which heterocyclic group may be substituted by 1 to 5 substituents selected from the group consisting of a halogen, $C_{1-3}$alkylenedioxy, nitro, cyano, optionally halogenated $C_{1-6}$alkyl, optionally halogenated $C_{3-6}$cycloalkyl, optionally halogenated $C_{1-6}$alkoxy, optionally halogenated $C_{1-6}$alkylthio, amino, mono-$C_{1-6}$alkylamino, di-$C_{1-6}$alkylamino, hydroxyl, $C_{1-6}$alkylcarbonyl, carboxyl, $C_{1-6}$alkoxycarbonyl, $C_{1-6}$alkylcarbonyloxy, carbamoyl, mono-$C_{1-6}$alkylcarbamoyl, di-$C_{1-6}$alkylcarbamoyl, sulfo, $C_{1-6}$alkylsulfonyl, $C_{6-10}$aryl, $C_6$-aryloxy and 5- or 6-membered heterocyclic group
  or a salt thereof, with a pharmaceutically acceptable carrier.

* * * * *

UNITED STATES PATENT AND TRADEMARK OFFICE
CERTIFICATE OF CORRECTION

PATENT NO. : 5,804,601
DATED : September 8, 1998
INVENTOR(S) : Kaneyoshi Kato et al.

It is certified that error appears in the above-identified patent and that said Letters Patent is hereby corrected as shown below:

Title page,
Item [56] References Cited, OTHER PUBLICATIONS
"Orgsinc" should read -- Organic --.

Column 1,
Line 25, "privilege" should read -- privileged --;
Line 48, "become" should read -- becomes --;
Line 60, "has," should read -- has --;
Line 61, "thus," should read -- thus --.

Column 2,
Line 7, "cells;" should read -- cells, --;
Line 8, "system;" should read -- system, --;
Line 15, "V.H, Perry, P-B. Anderson," should read -- V.H. Perry, P.B. Anderson --;
Line 16, "etc). should read -- etc. ). --.

Column 4,

Line 57, " 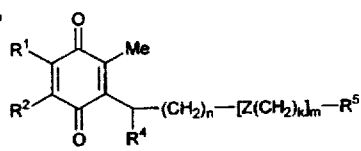 " should read

-- 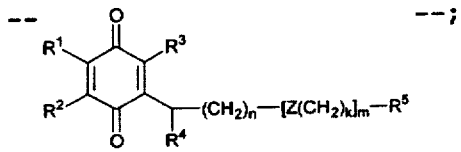 --;

Line 66, "wherein" should read -- [wherein --.

Column 6,
Line 15, "the" should read -- of the --.

UNITED STATES PATENT AND TRADEMARK OFFICE
CERTIFICATE OF CORRECTION

PATENT NO. : 5,804,601
DATED : September 8, 1998
INVENTOR(S) : Kaneyoshi Kato et al.

It is certified that error appears in the above-identified patent and that said Letters Patent is hereby corrected as shown below:

Column 7,
Line 29, "$C_6$–loaryll" should read -- $C_{6-10}$aryl --;
Line 30, "$C_6$–loaryloxy" should read -- $C_{6-10}$aryloxy --;
Line 59, "$C_{1-6}$aikoxy" should read -- $C_{1-6}$alkoxy --.

Column 8,
Line 43, "di–$C_1l_6$alkylcarbamoyl," should read -- di–$C_{1-6}$alkylcarbamoyl, --.

Column 9,
Line 12, "R2" should read -- $R_2$ --.

Column 13,
Line 34, "1,4–benzoquino' n–2–yl," should read -- 1,4–benzoquinon–2–yl, --;
Line 64, "$C_{26}$alkynylene" should read -- $C_{2-6}$alkynylene --.

Column 16,
Line 5, "$C_{6-1\wedge}$aryl" should read -- $C_{6-14}$aryl --;
Line 30, "$R^2$" should read -- $R^{2'}$ --;
Line 45, "2-benz-imidazolyl," should read -- 2-benzimidazolyl, --;
Line 64, "R" should read -- $R^4$ --;

Column 17,
Line 26, "2-benz-imidazolyl," should read -- 2-benzimidazolyl, --;

Column 23,
Line 60, "herein-before" should read -- hereinbefore --.

Column 24,
Line 30, "Der" should read -- Per --.

Column 26,
Line 12, "etc)" should read -- etc.) --.

Column 29,
Line 19, "(7II," should read -- (7H, -- and "(1II," should read -- (1H, -- and "IIz), should read -- (Hz), --; and "(1II," should read -- (1H, --.

UNITED STATES PATENT AND TRADEMARK OFFICE
CERTIFICATE OF CORRECTION

PATENT NO. : 5,804,601
DATED : September 8, 1998
INVENTOR(S) : Kaneyoshi Kato et al.

It is certified that error appears in the above-identified patent and that said Letters Patent is hereby corrected as shown below:

Column 30,
Line 46, "5.76Found:" should read -- 5.76; Found: --.

Column 33,
Line 1, "iN" should read -- 1N --;
Line 5, "1 N" should read -- 1N --.

Column 34,
Line 4, "(4H, in)" should read -- (4H, m), --;
Line 5, "(6II," should read -- (6H, -- and "(1II," should read -- 1H, -- and "IIz), should read -- Hz), -- and "IIz, should read -- Hz, --.

Column 35,
Line 41, "¹II-NMR" should read -- $^1$H-NMR --; and "(3II," should read -- (3H, --; and "IIz" should read -- Hz --.

Column 38,
Line 5, "(2II,m)," should read -- (2H, m), -- (3 occurrences) and (2II," should read -- (2H, --;
Line 21, "thio-phenol" should read -- thiophennnol --.

Column 42,
Line 1, "¹¹H-NMR" should read -- $^1$H-NMR --;
Line 57, "¹II-NMR" should read -- $^1$H-NMR --; and "(4II," should read -- (4H, --.

Column 43,
Line 52, "iN" should read -- 1N --;
Line 54, "trsidue" should read -- residue --.

Column 44,
Line 50, "OC" should read -- O°C --;
Line 67, "NaHCO$_3$aq.in" should read -- NaHCO$_3$aq in --.

Column 45,
Line 18, "was-stirred" should read -- was stirred --;
Line 39, "(1H,s). 3)" should read -- (1H,s). ¶3) --.

UNITED STATES PATENT AND TRADEMARK OFFICE
CERTIFICATE OF CORRECTION

PATENT NO.   : 5,804,601
DATED        : September 8, 1998
INVENTOR(S)  : Kaneyoshi Kato et al.

It is certified that error appears in the above-identified patent and that said Letters Patent is hereby corrected as shown below:

Column 46,
Line 35, "added a" should read -- added an --;
Line 40, "toluene-and" should read -- toluene and --;
Line 60, "manner." should read -- manner. ¶
Compound 1-2: 7-(1-hydroxy-2-naphthyl)-7-phenylheptanohydroxamic acid --;
Line 62, "heptenohydroxamic" should read -- heptanohydroxamic --;
Line 64, "heptenohydroxamic" should read -- heptanohydroxamic --.

Column 49,
Line 57, "hexanohyroxamic" should read -- hexanohydroxamic --;
Line 58, "(4-me-Ehoxyphenyl)" should read -- (4-methoxyphenyl --.

Column 50,
Line 31, "hexanohyroxamic" should read -- hexanohydroxamic --;
Line 52, "hexanohyroxamic" should read -- hexanohydroxamic --;
Line 57, "hexanohyroxamic" should read -- hexanohydroxamic --;
Line 60, "hexanohyroxamic" should read -- hexanohydroxamic --.

Column 51,
Line 4, "hexanohyroxamic" should read -- hexanohydroxamic --;
Line 10, "hexanohyroxamic" should read -- hexanohydroxamic --.

Column 52,
Line 25, "hexanohyroxamic" should read -- hexanohydroxamic --;

Column 57,
Table 6, "(1H, dt, J=12Hz), 7Hz)," should read -- (1H, dt, J=12Hz, 7Hz), --;
Table 7, "d, J=8.1Hz), 8.38(1H,d,J=5.5Hz), 8.66" should read -- d,J=8.1Hz), 8.38 (1H,d,J=5.5Hz), 8.66 --.

Column 60,
Table 10, "7.73(1H, m), 7.77-7.89(1H, m), 8.04-" should read -- 7.73(1H, m), 7.77-7.89(1H, m), 8.04- --.

UNITED STATES PATENT AND TRADEMARK OFFICE
CERTIFICATE OF CORRECTION

PATENT NO. : 5,804,601
DATED : September 8, 1998
INVENTOR(S) : Kaneyoshi Kato et al.

It is certified that error appears in the above-identified patent and that said Letters Patent is hereby corrected as shown below:

Column 64,
Table 14, "(1.28-1.48(2H," should read -- 1.28-1.48(2H, --.

Column 68,
Table 17, "94-85" should read -- 94-95 --;
Table 17, "4.39)1H," should read -- 4.39(1H, --.

Column 69,
Table 19,

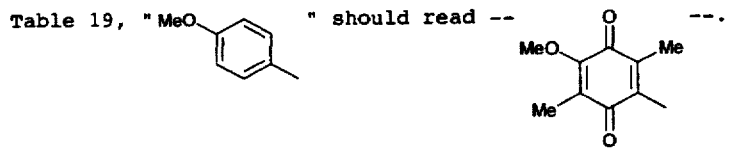

Column 70,
Table 20, "substabce" should read -- substance --.

Column 72,
Table 22, "2.99(2II,t, J=7.9IIz), 3.35(2II, q, J=7.3" should read -- 2.99 (2H,t, J=7.9Hz), 3.335(2H,q, J=7.3 --.

Column 86,
Line 56, "cells," should read -- cells --.

Column 87,
Line 67, "naphtho-quinon-2-yl)" should read -- naphthoquinon-2-yl) --.

Column 88,
Line 25, "TNFO" should read -- TNFα --.

UNITED STATES PATENT AND TRADEMARK OFFICE
CERTIFICATE OF CORRECTION

PATENT NO. : 5,804,601
DATED : September 8, 1998
INVENTOR(S) : Kaneyoshi Kato et al.

It is certified that error appears in the above-identified patent and that said Letters Patent is hereby corrected as shown below:

Column 89,
Line 48, "$NO_3$-$NO_2$-" should read -- $NO_3$-/$NO_2$- --;
Line 54, "$N_2$-" should read -- $NO_2$- --.

Column 93,
Line 45, "–CO–NII–R." should read -- –CO–NH–R, --;
Line 47, "2-quinolyl, 3-quinolyl," should read -- 2-quinolyl, 3-quinolyl, --.

Column 96,
Line 27, "$C_{1-6}$cycloalkyl," should read -- $C_{3-6}$cycloalkyl, --;
Line 37, "consisting" should read -- consisting of --;
Line 48, "$C_6$–aryloxy" should read -- $C_{6-10}$aryloxy --.

Signed and Sealed this

Nineteenth Day of February, 2002

*Attest:*

JAMES E. ROGAN
*Attesting Officer*     Director of the United States Patent and Trademark Office